United States Patent
Yellin et al.

(10) Patent No.: US 6,340,459 B1
(45) Date of Patent: *Jan. 22, 2002

(54) THERAPEUTIC APPLICATIONS FOR THE ANTI-T-BAM (CD40-L) MONOCLONAL ANTIBODY 5C8 IN THE TREATMENT OF REPERFUSION INJURY IN NON-TRANSPLANT RECIPIENTS

(75) Inventors: Michael J. Yellin, Riverdale; Seth Lederman, New York; Leonard Chess, Scarsdale, all of NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/637,323

(22) Filed: Apr. 22, 1996

Related U.S. Application Data

(63) Continuation-in-part of application No. 08/567,391, filed on Dec. 1, 1995, now abandoned, and a continuation-in-part of application No. 08/566,258, filed on Dec. 1, 1995, now abandoned.

(51) Int. Cl.$^7$ ................... A61K 39/395; C07K 16/28; G01N 33/53

(52) U.S. Cl. ................... 424/154.1; 424/130.1; 424/133.1; 424/135.1; 424/141.1; 424/143.1; 424/144.1; 424/153.1; 424/173.1; 530/387.1; 530/387.3; 530/388.1; 530/388.22; 530/388.7; 530/388.73; 530/388.75; 530/388.2; 435/7.1; 435/7.2; 435/7.21; 435/7.24

(58) Field of Search .................... 424/130.1, 133.1, 424/135.1, 141.1, 143.1, 144.1, 152.1, 153.1, 154.1, 172.1, 173.1; 530/387.1, 387.3, 388.1, 388.15, 388.2, 388.22, 388.7, 388.73; 435/7.1, 7.2

(56) References Cited

U.S. PATENT DOCUMENTS

| | | | |
|---|---|---|---|
| 5,474,771 A | * 12/1995 | Lederman et al. | |
| 5,540,926 A | 7/1996 | Aruffo et al. | 424/153.1 |
| 5,652,224 A | 7/1997 | Wilson et al. | 514/44 |
| 5,674,492 A | 10/1997 | Armitage et al. | 424/144.1 |
| 5,677,165 A | 10/1997 | de Boer et al. | 435/240.27 |
| 5,683,693 A | 11/1997 | Noelle et al. | 424/144.1 |
| 5,747,037 A | 5/1998 | Noelle et al. | 424/154.1 |
| 5,804,177 A | * 9/1998 | Humphries | |
| 5,833,987 A | 11/1998 | Noelle et al. | 424/154.1 |
| 5,869,049 A | 2/1999 | Noelle et al. | 424/154.1 |
| 5,876,718 A | 3/1999 | Noelle et al. | 424/154.1 |
| 5,876,950 A | 3/1999 | Siadak et al. | 435/7.23 |
| 5,902,585 A | 5/1999 | Noelle et al. | 424/144.1 |
| 5,916,560 A | 6/1999 | Larsen et al. | 424/154.1 |
| 5,942,229 A | 8/1999 | Noelle et al. | 424/154.1 |
| 5,945,513 A | 8/1999 | Aruffo et al. | 530/387.3 |
| 5,961,974 A | 10/1999 | Armitage et al. | 424/154.1 |
| 5,962,406 A | 10/1999 | Armitage et al. | 514/8 |
| 5,981,724 A | 11/1999 | Armitage et al. | 536/23.5 |
| 5,993,816 A | 11/1999 | Lederman et al. | 424/154.1 |
| 6,001,358 A | 12/1999 | Black et al. | 424/154.1 |

FOREIGN PATENT DOCUMENTS

| | | | |
|---|---|---|---|
| WO | WO 93/08207 | 4/1993 | C07H/21/00 |
| WO | 93/09812 | * 5/1993 | |
| WO | WO 94/04570 | 3/1994 | C07K/15/06 |
| WO | WO 95/06481 | 3/1995 | A61K/39/395 |
| WO | WO 95/06666 | 3/1995 | C07K/16/28 |
| WO | WO 95/09653 | 4/1995 | A61K/39/395 |
| WO | WO 96/23071 | 8/1996 | C12N/15/13 |
| WO | WO 96/28568 | 9/1996 | C12P/21/02 |
| WO | WO 96/40246 | 12/1996 | A61K/39/395 |
| WO | WO 97/17446 | 5/1997 | C12N/15/13 |
| WO | WO 98/30240 | 7/1998 | A61K/39/395 |
| WO | WO 98/30241 | 7/1998 | A61K/39/395 |

OTHER PUBLICATIONS

Press Release from IDEC Pharmaceuticals, Inc. (Apr. 20, 2000).

Press Release from IDEC Pharmaceuticals, Inc. (Jan. 29, 2001).

Press Release from Biogen website (www.prnewswire.com), "Biogen Says it Has Halted Several Trials of Anti–CD40 Ligand Monoclonal Antibody", Oct. 21, 1999.

Press Release from Biogen website (www.prnewswire.com), "Biogen Says it Has Stopped Ongoing Trials of Anti–CD40 Ligand Monoclonal Antibody", Nov. 2, 1999.

Bajorath J. et al. "Identification of Residues on CD40 and Its Ligand Which Are Critical for the Receptor–Ligand Interaction", *Biochemistry* 34:1833–1844 (1995).

Banchereau J. et al. "The CD40 Antigen and its Ligand", *Annual Rev. Immunol.* 12:881–922 (1994).

Cleary, A. M. et al. "Opposing roles of CD95 (Fas/APO–1) and CD40 in the Death and Rescue of Human Low Density Tonsillar B Cells", *J. Immunol.* 155:3329–3337 (1995).

(List continued on next page.)

*Primary Examiner*—Phillip Gambel
(74) *Attorney, Agent, or Firm*—John P. White; Cooper & Dunham LLP

(57) ABSTRACT

Activation of cells bearing CD40 on their cell surface by CD40 ligand is inhibited by contacting the cells with an agent capable of inhibiting interaction between CD40 ligand and the cells, in an amount effective to inhibit activation of the cells. Activation of cells bearing CD40 on their surface by CD40 ligand in a subject is inhibited by administering to the subject an agent capable of inhibiting interaction between CD40 ligand and the cells, in an amount effective to inhibit activation of the cells. Reperfusion injury, in an non-transplant recipient, is a condition associated with CD40 ligand-induced activation of CD40-bearing cells. Therefore, reperfusion injury can be treated by the administration of anti-human CD40L monoclonal antibodies, such as those described herein (e.g. 5c8 mAb).

23 Claims, 46 Drawing Sheets

OTHER PUBLICATIONS

Fanslow W. C. et al. "Soluble Forms of CD40 Inhibit Biologic Responses of Human B Cells", *J. Immunol.* 149:655–660 (1992).

Yellin M. J. et al. "In situ Characterization of CD40L and CD40 Expression in Glomerulonephritis (GN)", Abstract—ASBMB/ASIP/AAI Joint Meeting (1996).

Yellin M. J. et al. "Function of CD40 Molecules Expressed on Cultured Synovial Membrane Fibroblasts", *FASEB J.* 9:A774—Abstract No. 4483 (1995).

Alderson, M.R. et al. (1993). J. Exp. Med. 178: 669–674.
Carbone, A et al., (1995) Blood 85(3): 780–789.
Clark, E A et al., (1986) Proc. Natl. Acad. Sci. USA 83: 4494–4498.
Freudenthal, PS et al., (1990) Proc. Natl. Acad. Sci. USA 87: 7698–7702.
Galy, AHM et al., (1992) J. Immunol. 149: 775–782.
Hasbold, J et al., (1994) Eur. J. Immunol. 24: 1835–1842.
Hollenbaugh, D et al., (1995) J. Exp. Med. 182: 33–40.
Karmann, K et al., (1995) Proc. Natl. Acad. Sci. USA 92: 4342–4346.
Karpusas, M et al., (1995) Structure 3(10): 1031–1039.
Law, CL et al., (1990) Leukemia 4(11): 732–738.
O'Grady, J T et al., (1994) Am. J. Pathology 144(1): 2126.
Paulie, S et al., (1985) Cancer Immunol. Immunother. 20: 23–28.
Potocnik, AJ et al., (1990) Scand. J. Immunol. 31: 213–224.
Uckun, FM et al., (1990) Blood 76(12); 2449–2456.
Urashima, M et al., (1995) Blood 85: 1903–1912.
Valent, P et al., (1990) Int. Arch. Allergy Appl. Immunol. 91: 198–203.
Westendorf, JJ et al., (1995) Curr. Top. Microbiol. Immunol. 194: 63–72.
Westendorf JJ et al., (1994) J. Immunol. 152: 117–128.
Yellin, M.J. et al., (1995) Oral Presentation at FASEB Meeting in Atlanta, GA, Apr. 12, 1995.
Yellin, M.J. et al., (1995) Poster session at 9th International Congress of Immunology Meeting in San Francisco, CA.
Yellin, M.J. et al., (1995) J. Leukocyte Biology 58: 209–216.
Yellin, M.J. et al., (1995) J. Exp. Med. 182: 1857–1864.
Young L.S. et al., (1989) Int. J. Cancer 43: 786–794.
Kuntz Science 257: 1078–1082 (1992.*
Buhlmann et al. J Clin Immunol. 16:83–89 (1996).*
Larsen et al. Transplantation 61:4–9(1996).*
Gray et al. J Exp Med. 180: 141–155(1994).*
Stuber et al. J Exp Med. 183:693–698(1996).*
Merck Manual 16th Ed. Merck Research Laboratories Rathway NJ 1992 p. 718.*
Mohan et al. J. Immunol. J. Immunol 154:1470–1480(1995).*
Laman et al. J. Neuroimmunol. 54:175 (1994).*
Biacone et al. Kidney Intl. 48:458–468 (1995).*
Durie et al. Res. Immunol. 145: 200–205 (1994).*
Durie et al. Immunol. Today 15:406–411 (1994).*
Lederman et al. Res. Immunol. 145:215–222(1994).*
Durie et al. Science 261:1328–1330 (1993).*
Kuwana et al. J. Immunol. 155: 2703–2714 (1995).*
Haug et al. Transplantation 55:766–773 (1993).*
Morgan et al. Transplantation 55:919–923 (1993).*
Bancherean et al. Annu. Rev. Immunol. 12:881–922 (1994).*

* cited by examiner

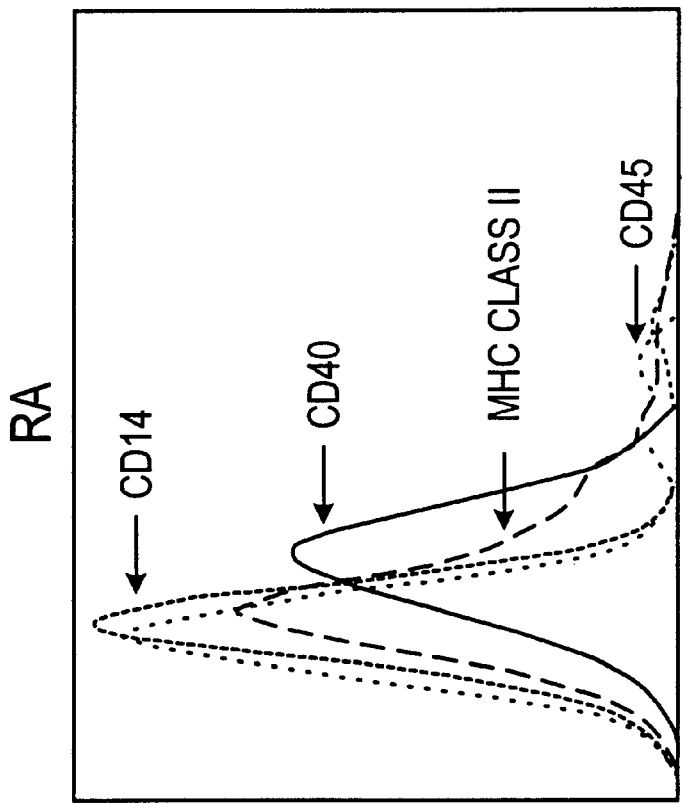
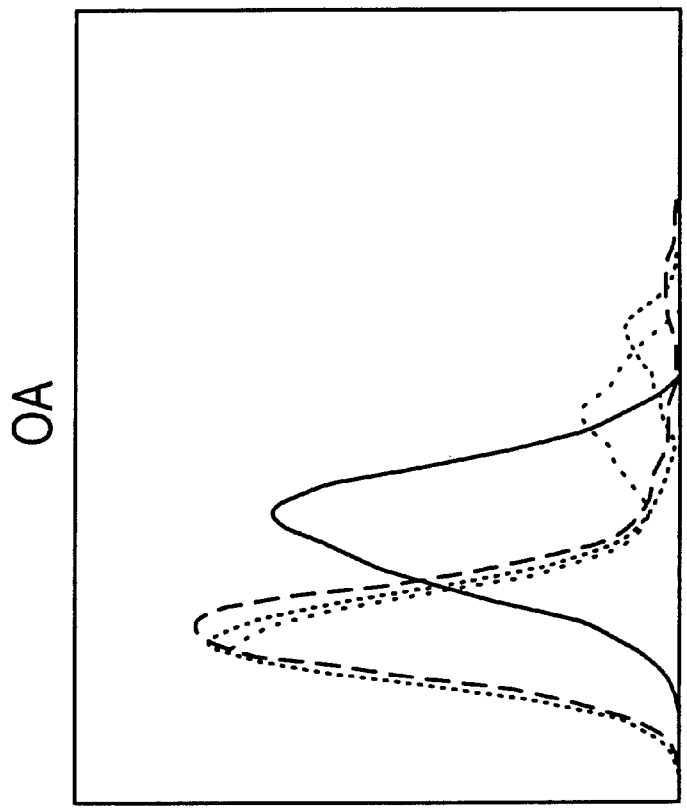
FIG.1A
RA
CD14
CD40
MHC CLASS II
CD45
FIG.1B
OA

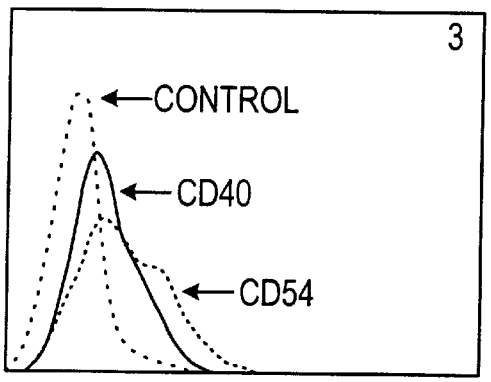
FIG.2A RESTING
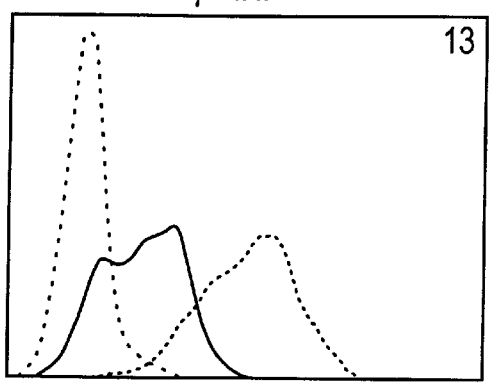
FIG.2B γ-INF
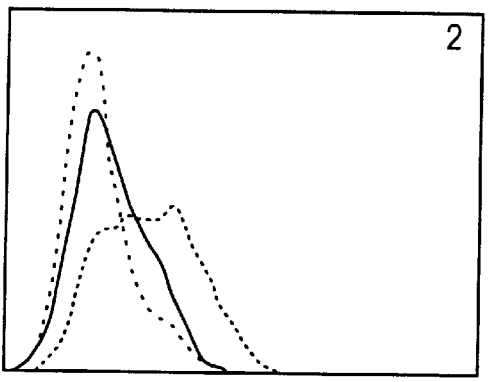
FIG.2C
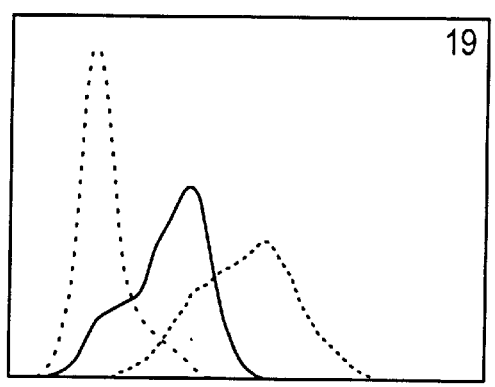
FIG.2D
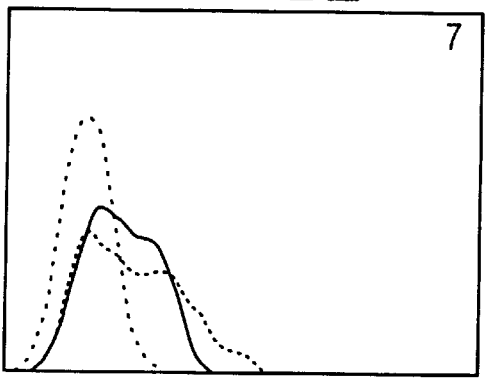
FIG.2E
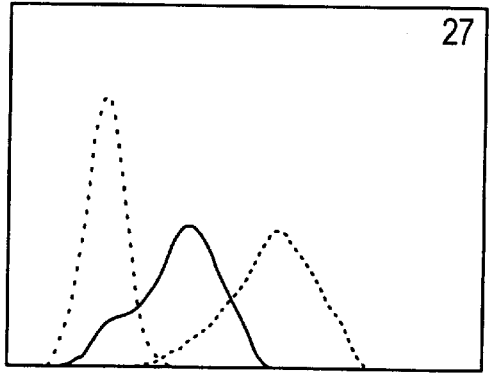
FIG.2F IA.1 cells plus:

Media

D1.1

D1.1
+
Anti-CD40L mAb

D1.1
+
Isotype Control mAb

B2.7

INF-γ

CD13 Fluorescence

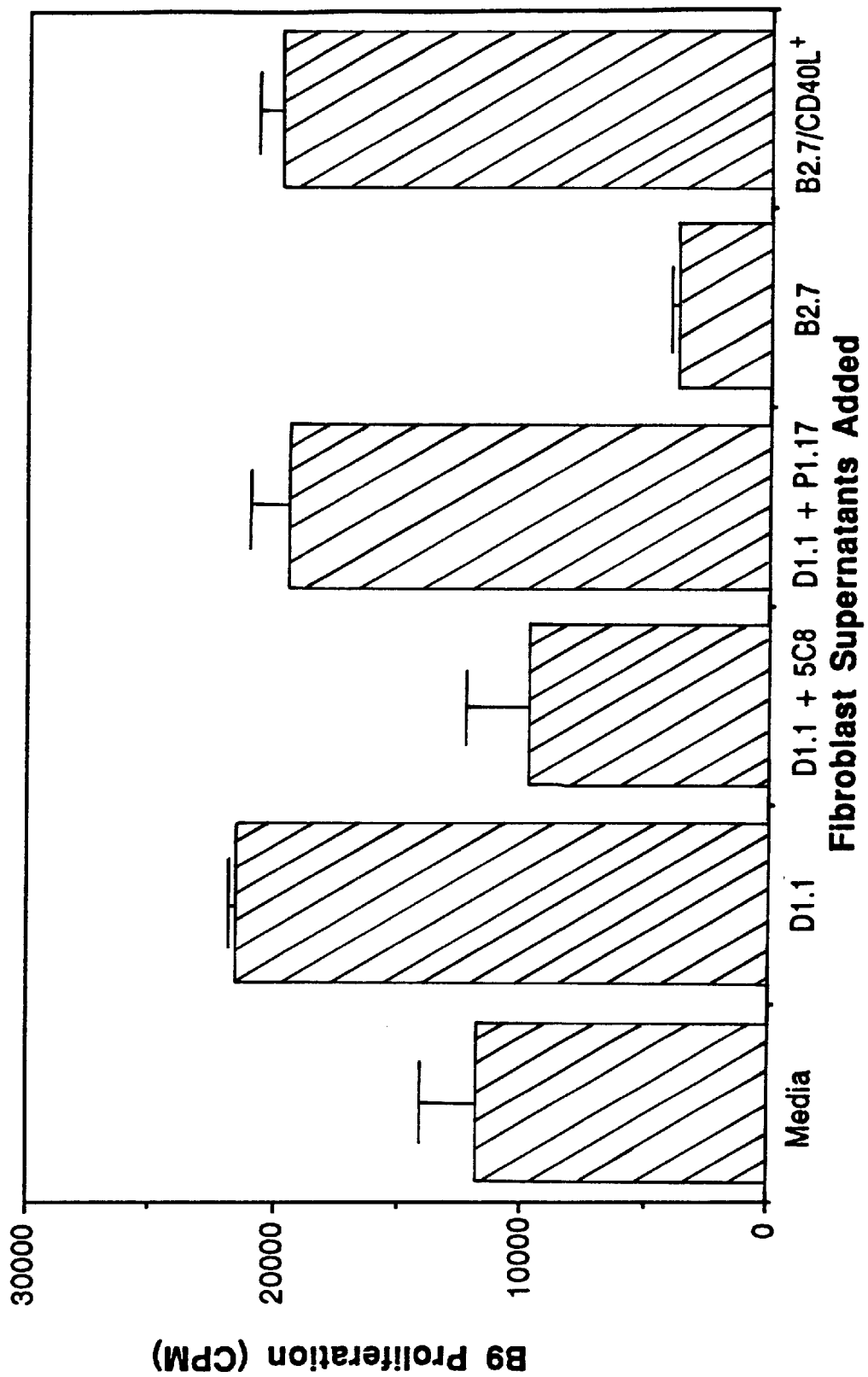

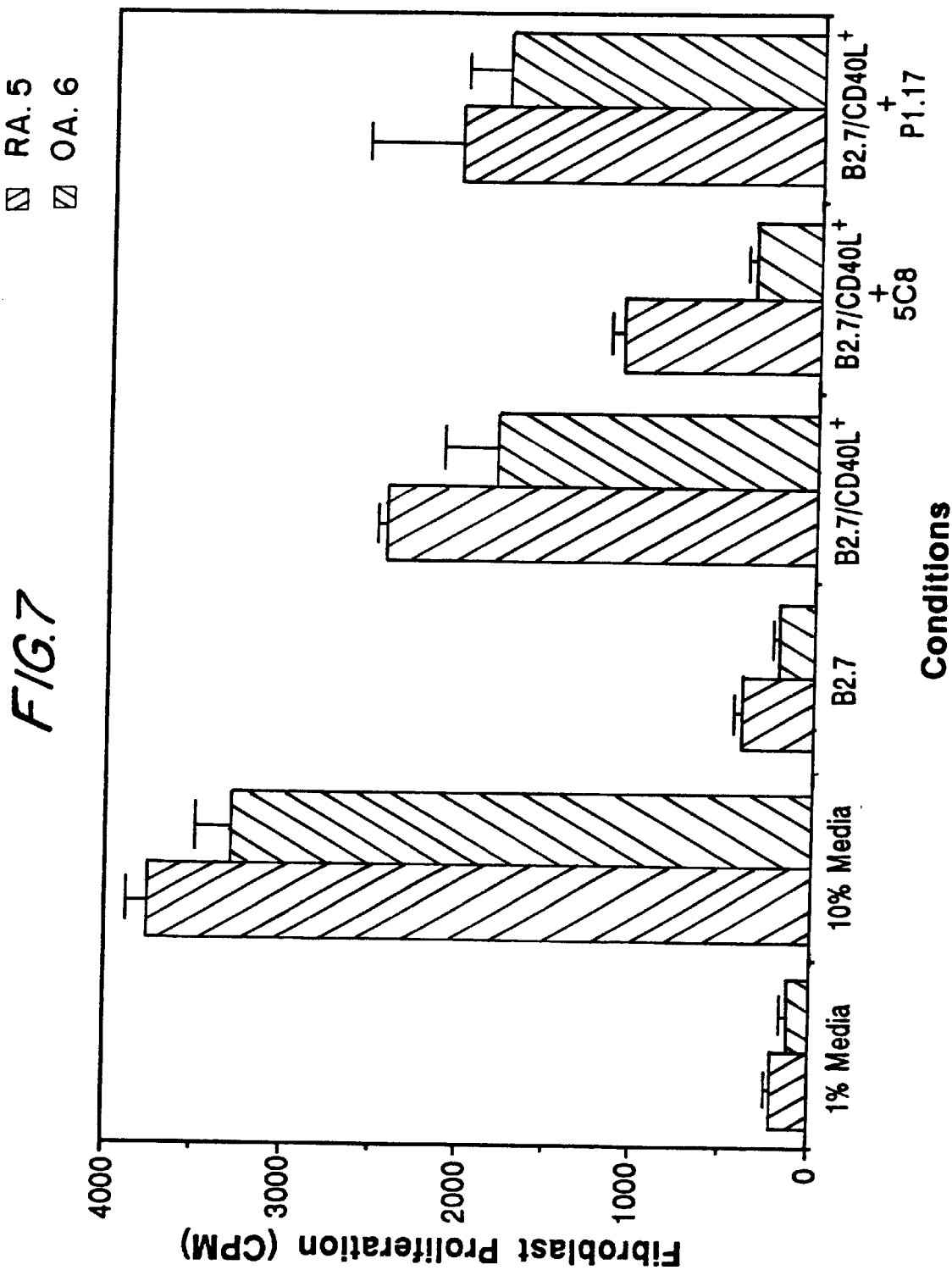

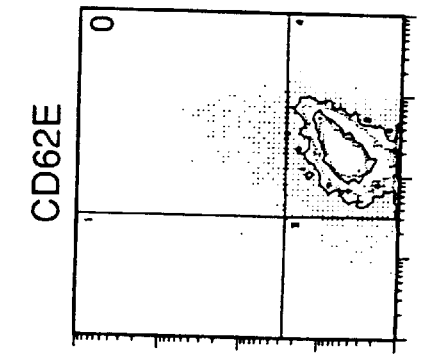
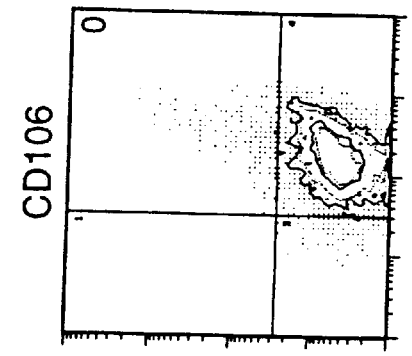
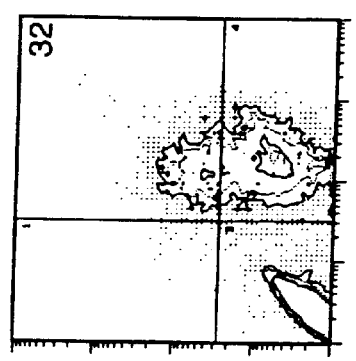
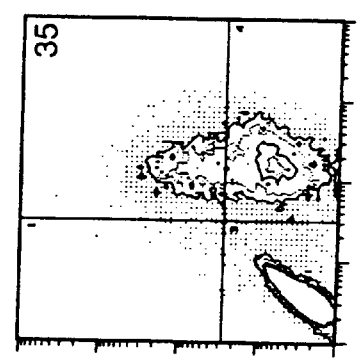
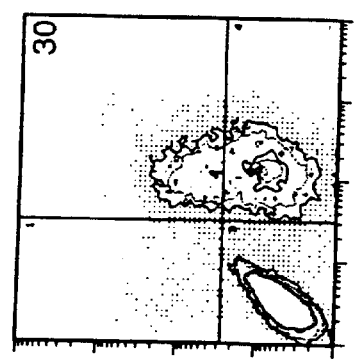

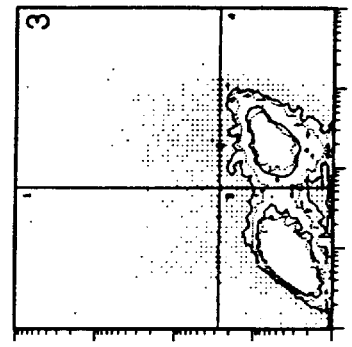
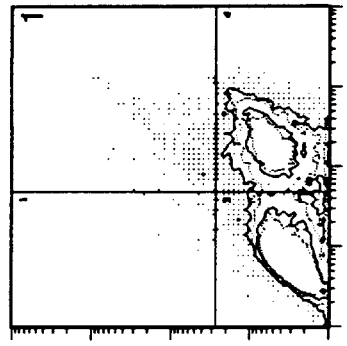
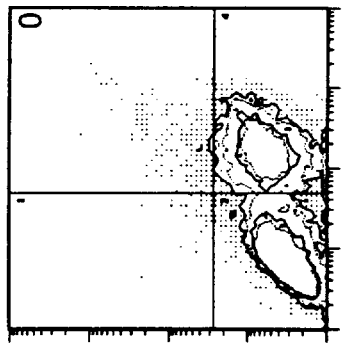
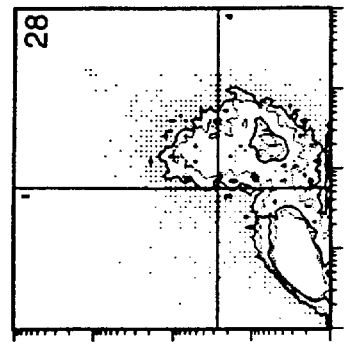
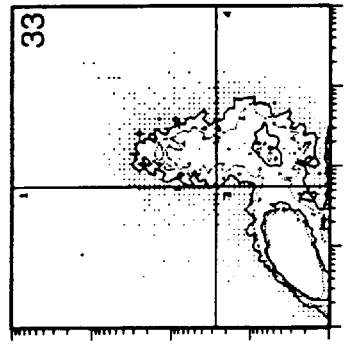
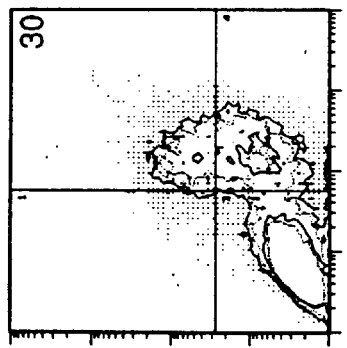

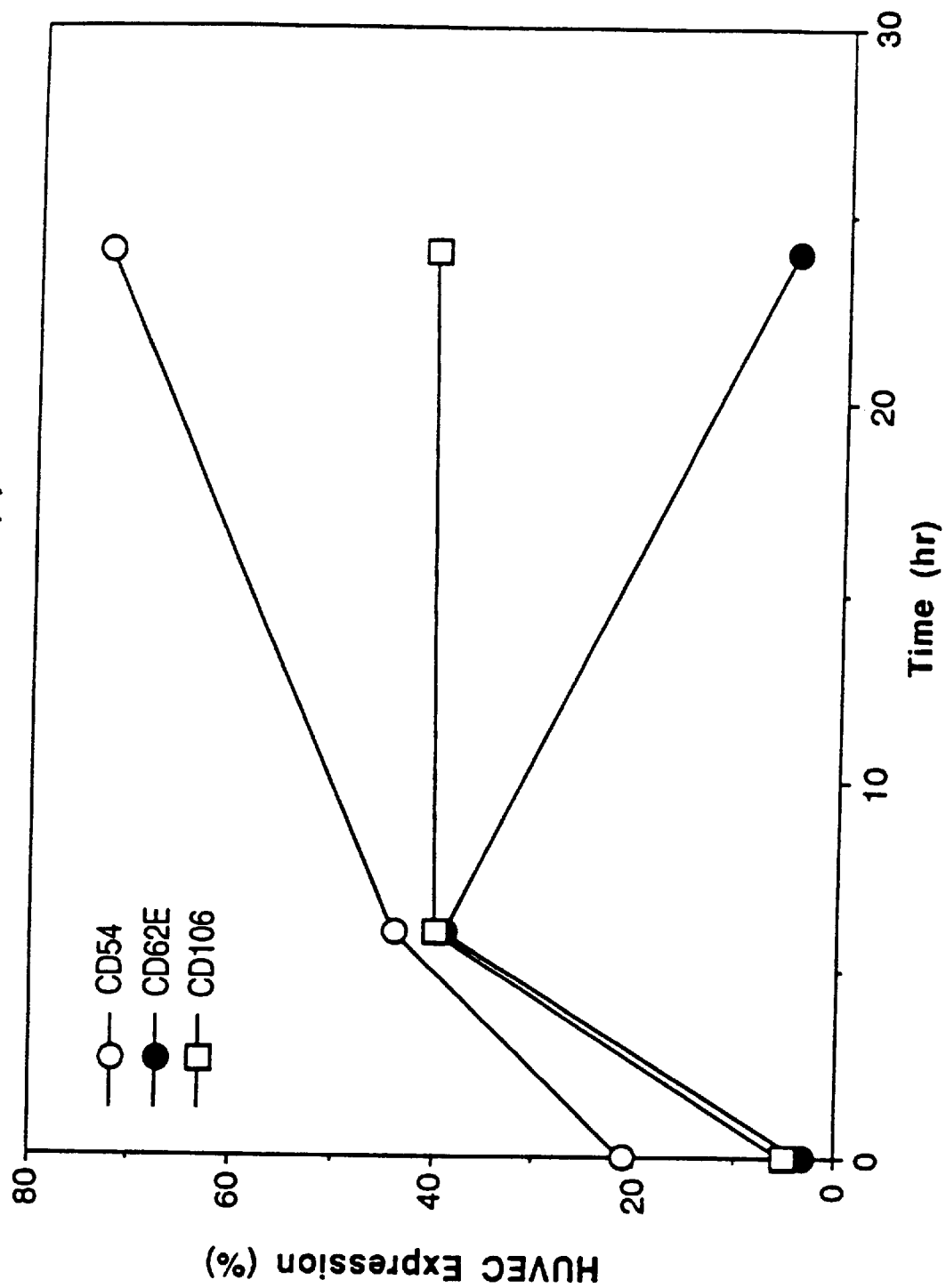

FIG.17A

```
REMARKS ATOMIC COORDINATES OF CD40L CRYSTAL STRUCTURE IN PDB FORMAT
CRYST     77.170      77.170     90.460  90.00  90.00 120.00 R3
ATOM      1   N    GLY  116     -7.954  -16.144   22.488  1.00  64.71        A
ATOM      2   HT1  GLY  116     -7.087  -15.852   21.964  1.00  15.00        A
ATOM      3   HT2  GLY  116     -8.082  -17.142   22.242  1.00  15.00        A
ATOM      4   HT3  GLY  116     -8.630  -15.576   21.928  1.00  15.00        A
ATOM      5   CA   GLY  116     -7.927  -15.755   23.928  1.00  64.37        A
ATOM      6   C    GLY  116     -6.990  -16.621   24.780  1.00  64.34        A
ATOM      7   O    GLY  116     -6.968  -17.814   24.563  1.00  64.44        A
ATOM      8   N    ASP  117     -6.238  -16.043   25.740  1.00  64.04        A
ATOM      9   H    ASP  117     -5.617  -16.709   26.170  1.00  15.00        A
ATOM     10   CA   ASP  117     -6.284  -14.616   26.130  1.00  63.57        A
ATOM     11   CB   ASP  117     -5.711  -14.402   27.539  1.00  63.36        A
ATOM     12   CG   ASP  117     -6.518  -15.163   28.574  1.00  63.71        A
ATOM     13   OD1  ASP  117     -6.090  -16.247   28.965  1.00  63.24        A
ATOM     14   OD2  ASP  117     -7.566  -14.668   28.987  1.00  63.29        A
ATOM     15   C    ASP  117     -5.651  -13.585   25.184  1.00  63.31        A
ATOM     16   O    ASP  117     -6.039  -12.427   25.145  1.00  63.35        A
ATOM     17   N    GLN  118     -4.713  -14.090   24.379  1.00  62.72        A
ATOM     18   H    GLN  118     -4.450  -15.040   24.541  1.00  15.00        A
ATOM     19   CA   GLN  118     -4.097  -13.313   23.281  1.00  61.79        A
ATOM     20   CB   GLN  118     -2.918  -14.117   22.687  1.00  62.46        A
ATOM     21   CG   GLN  118     -3.047  -15.659   22.562  1.00  62.95        A
ATOM     22   CD   GLN  118     -4.277  -16.118   21.790  1.00  63.26        A
ATOM     23   OE1  GLN  118     -5.396  -16.000   22.277  1.00  63.43        A
ATOM     24   NE2  GLN  118     -4.044  -16.665   20.601  1.00  63.42        A
ATOM     25   HE21 GLN  118     -4.836  -16.715   19.975  1.00  15.00        A
ATOM     26   HE22 GLN  118     -3.151  -16.995   20.298  1.00  15.00        A
ATOM     27   C    GLN  118     -4.999  -12.841   22.128  1.00  60.59        A
ATOM     28   O    GLN  118     -4.887  -13.379   21.052  1.00  60.79        A
ATOM     29   N    ASN  119     -5.912  -11.901   22.445  1.00  58.61        A
ATOM     30   H    ASN  119     -5.917  -11.600   23.389  1.00  15.00        A
ATOM     31   CA   ASN  119     -6.689  -11.222   21.386  1.00  56.39        A
ATOM     32   CB   ASN  119     -7.947  -11.982   20.936  1.00  56.95        A
ATOM     33   CG   ASN  119     -7.652  -13.352   20.375  1.00  57.45        A
ATOM     34   OD1  ASN  119     -7.941  -14.303   21.084  1.00  58.50        A
ATOM     35   ND2  ASN  119     -7.005  -13.431   19.241  1.00  58.58        A
ATOM     36   HD21 ASN  119     -6.843  -12.617   18.646  1.00  15.00        A
ATOM     37   HD22 ASN  119     -6.740  -14.221   18.684  1.00  15.00        A
ATOM     38   C    ASN  119     -7.053   -9.724   21.571  1.00  53.62        A
ATOM     39   O    ASN  119     -6.746   -8.933   20.694  1.00  56.55        A
ATOM     40   N    PRO  120     -7.737   -9.288   22.698  1.00  50.17        A
ATOM     41   CD   PRO  120     -8.151  -10.129   23.810  1.00  51.90        A
ATOM     42   CA   PRO  120     -8.402   -7.945   22.818  1.00  48.19        A
ATOM     43   CB   PRO  120     -9.191   -8.008   24.117  1.00  47.42        A
ATOM     44   CG   PRO  120     -9.444   -9.493   24.321  1.00  51.93        A
ATOM     45   C    PRO  120     -7.750   -6.524   22.657  1.00  45.59        A
ATOM     46   O    PRO  120     -8.187   -5.516   23.225  1.00  45.37        A
ATOM     47   N    GLN  121     -6.789   -6.458   21.721  1.00  38.52        A
ATOM     48   H    GLN  121     -6.287   -7.304   21.505  1.00  15.00        A
ATOM     49   CA   GLN  121     -6.733   -5.359   20.753  1.00  29.14        A
ATOM     50   CB   GLN  121     -5.454   -5.735   19.971  1.00  26.30        A
ATOM     51   CG   GLN  121     -5.128   -4.943   18.710  1.00  26.84        A
ATOM     52   CD   GLN  121     -4.923   -3.460   18.949  1.00  27.26        A
ATOM     53   OE1  GLN  121     -5.822   -2.668   18.709  1.00  28.66        A
ATOM     54   NE2  GLN  121     -3.717   -3.100   19.341  1.00  33.90        A
ATOM     55   HE21 GLN  121      2.883   -3.614   19.564  1.00  15.00        A
ATOM     56   HE22 GLN  121     -3.442   -2.138   19.204  1.00  15.00        A
ATOM     57   C    GLN  121     -8.065   -5.218   19.903  1.00  26.33        A
ATOM     58   O    GLN  121     -8.905   -6.097   19.834  1.00  21.41        A
ATOM     59   N    ILE  122     -8.288   -4.051   19.272  1.00  21.21        A
```

FIG. 17B

```
ATOM    60  H    ILE  122    -7.600   -3.320  19.337  1.00  15.00      A
ATOM    61  CA   ILE  122    -9.383   -3.952  18.295  1.00  20.92      A
ATOM    62  CB   ILE  122   -10.238   -2.629  18.396  1.00  22.17      A
ATOM    63  CG2  ILE  122   -11.275   -2.428  17.272  1.00  21.61      A
ATOM    64  CG1  ILE  122   -11.076   -2.744  19.668  1.00  24.13      A
ATOM    65  CD1  ILE  122   -11.751   -1.440  20.073  1.00  23.04      A
ATOM    66  C    ILE  122    -8.833   -4.108  16.895  1.00  18.96      A
ATOM    67  O    ILE  122    -8.135   -3.243  16.379  1.00  17.93      A
ATOM    68  N    ALA  123    -9.159   -5.240  16.283  1.00  14.72      A
ATOM    69  H    ALA  123    -9.599   -5.978  16.805  1.00  15.00      A
ATOM    70  CA   ALA  123    -8.656   -5.401  14.917  1.00  14.29      A
ATOM    71  CB   ALA  123    -7.176   -5.868  14.903  1.00  12.83      A
ATOM    72  C    ALA  123    -9.483   -6.315  13.985  1.00  15.66      A
ATOM    73  O    ALA  123   -10.170   -7.261  14.323  1.00  13.58      A
ATOM    74  N    ALA  124    -9.388   -6.009  12.724  1.00  13.45      A
ATOM    75  H    ALA  124    -8.894   -5.185  12.456  1.00  15.00      A
ATOM    76  CA   ALA  124   -10.087   -6.920  11.836  1.00  14.55      A
ATOM    77  CB   ALA  124   -11.486   -6.368  11.446  1.00  11.37      A
ATOM    78  C    ALA  124    -9.271   -7.123  10.563  1.00  13.54      A
ATOM    79  O    ALA  124    -8.501   -6.274  10.129  1.00  16.29      A
ATOM    80  N    HIS  125    -9.544   -8.248   9.937  1.00  11.49      A
ATOM    81  H    HIS  125   -10.100   -8.900  10.426  1.00  15.00      A
ATOM    82  CA   HIS  125    -9.100   -8.524   8.590  1.00  11.51      A
ATOM    83  CB   HIS  125    -7.605   -8.908   8.614  1.00  11.43      A
ATOM    84  CG   HIS  125    -7.119   -9.116   7.205  1.00   7.41      A
ATOM    85  ND1  HIS  125    -6.750   -8.130   6.421  1.00   6.60      A
ATOM    86  HD1  HIS  125    -6.708   -7.168   6.621  1.00  15.00      A
ATOM    87  CD2  HIS  125    -7.075  -10.291   6.456  1.00  12.36      A
ATOM    88  NE2  HIS  125    -6.670   -9.971   5.234  1.00   6.20      A
ATOM    89  CE1  HIS  125    -6.462   -8.646   5.211  1.00   4.48      A
ATOM    90  C    HIS  125   -10.024   -9.570   7.931  1.00  12.63      A
ATOM    91  O    HIS  125   -10.324  -10.650   8.383  1.00  13.14      A
ATOM    92  N    VAL  126   -10.550   -9.129   6.806  1.00  15.65      A
ATOM    93  H    VAL  126   -10.169   -8.286   6.428  1.00  15.00      A
ATOM    94  CA   VAL  126   -11.743   -9.717   6.201  1.00  14.38      A
ATOM    95  CB   VAL  126   -12.877   -8.808   6.675  1.00  13.37      A
ATOM    96  CG1  VAL  126   -13.794   -9.722   7.379  1.00  12.60      A
ATOM    97  CG2  VAL  126   -13.449   -7.663   5.814  1.00   9.61      A
ATOM    98  C    VAL  126   -11.502   -9.971   4.685  1.00  16.03      A
ATOM    99  O    VAL  126   -10.684   -9.297   4.074  1.00  16.42      A
ATOM   100  N    ILE  127   -12.118  -11.013   4.136  1.00  15.99      A
ATOM   101  H    ILE  127   -12.807  -11.481   4.691  1.00  15.00      A
ATOM   102  CA   ILE  127   -11.651  -11.532   2.831  1.00  14.86      A
ATOM   103  CB   ILE  127   -11.414  -13.051   3.002  1.00  17.56      A
ATOM   104  CG2  ILE  127   -11.716  -13.910   1.765  1.00  17.17      A
ATOM   105  CG1  ILE  127    -9.972  -13.316   3.399  1.00  16.47      A
ATOM   106  CD1  ILE  127    -9.705  -12.992   4.864  1.00  19.64      A
ATOM   107  C    ILE  127   -12.691  -11.269   1.765  1.00  18.96      A
ATOM   108  O    ILE  127   -13.898  -11.391   2.016  1.00  20.01      A
ATOM   109  N    SER  128   -12.229  -10.882   0.581  1.00  17.54      A
ATOM   110  H    SER  128   -11.232  -10.871   0.382  1.00  15.00      A
ATOM   111  CA   SER  128   -13.274  -10.667  -0.437  1.00  15.55      A
ATOM   112  CB   SER  128   -12.664  -10.130  -1.706  1.00  18.16      A
ATOM   113  OG   SER  128   -12.205  -11.207  -2.574  1.00  19.90      A
ATOM   114  HG   SER  128   -11.832  -11.931  -2.029  1.00  15.00      A
ATOM   115  C    SER  128   -14.295  -11.761  -0.792  1.00  13.62      A
ATOM   116  O    SER  128   -14.052  -12.960  -0.832  1.00   8.98      A
ATOM   117  N    GLU  129   -15.492  -11.246  -1.027  1.00  13.36      A
ATOM   118  H    GLU  129   -15.661  -10.257  -0.937  1.00  15.00      A
ATOM   119  CA   GLU  129   -16.379  -12.024  -1.840  1.00  17.20      A
```

FIG. 17C

```
ATOM    120  CB   GLU   129     -17.052  -13.117   -1.021  1.00  20.55      A
ATOM    121  CG   GLU   129     -18.092  -12.694   -0.036  1.00  17.92      A
ATOM    122  CD   GLU   129     -18.781  -13.951    0.376  1.00  21.98      A
ATOM    123  OE1  GLU   129     -19.997  -13.932    0.368  1.00  32.23      A
ATOM    124  OE2  GLU   129     -18.150  -14.938    0.734  1.00  33.12      A
ATOM    125  C    GLU   129     -17.371  -11.409   -2.809  1.00  17.71      A
ATOM    126  O    GLU   129     -17.972  -10.389   -2.553  1.00  21.59      A
ATOM    127  N    ALA   130     -17.550  -12.145   -3.914  1.00  20.52      A
ATOM    128  H    ALA   130     -17.136  -13.057   -3.923  1.00  15.00      A
ATOM    129  CA   ALA   130     -18.379  -11.649   -5.019  1.00  23.36      A
ATOM    130  CB   ALA   130     -18.424  -12.633   -6.208  1.00  19.66      A
ATOM    131  C    ALA   130     -19.811  -11.298   -4.570  1.00  26.86      A
ATOM    132  O    ALA   130     -20.519  -12.022   -3.869  1.00  29.40      A
ATOM    133  N    SER   131     -20.198  -10.086   -4.968  1.00  21.70      A
ATOM    134  H    SER   131     -19.515   -9.481   -5.410  1.00  15.00      A
ATOM    135  CA   SER   131     -21.592   -9.782   -4.732  1.00  20.04      A
ATOM    136  CB   SER   131     -21.829   -8.266   -4.787  1.00  20.65      A
ATOM    137  OG   SER   131     -23.182   -8.001   -4.435  1.00  15.24      A
ATOM    138  HG   SER   131     -23.329   -7.069   -4.559  1.00  15.00      A
ATOM    139  C    SER   131     -22.546  -10.501   -5.668  1.00  17.15      A
ATOM    140  O    SER   131     -22.236  -10.853   -6.786  1.00  14.30      A
ATOM    141  N    SER   132     -23.756  -10.731   -5.187  1.00  20.15      A
ATOM    142  H    SER   132     -23.967  -10.586   -4.209  1.00  15.00      A
ATOM    143  CA   SER   132     -24.674  -11.250   -6.218  1.00  21.62      A
ATOM    144  CB   SER   132     -25.266  -12.616   -5.893  1.00  16.00      A
ATOM    145  OG   SER   132     -26.203  -12.324   -4.894  1.00  23.84      A
ATOM    146  HG   SER   132     -26.016  -12.944   -4.179  1.00  15.00      A
ATOM    147  C    SER   132     -25.727  -10.268   -6.671  1.00  20.07      A
ATOM    148  O    SER   132     -26.535  -10.544   -7.547  1.00  20.27      A
ATOM    149  N    LYS   133     -25.606   -9.063   -6.118  1.00  21.87      A
ATOM    150  H    LYS   133     -24.904   -8.969   -5.397  1.00  15.00      A
ATOM    151  CA   LYS   133     -26.406   -7.916   -6.517  1.00  19.23      A
ATOM    152  CB   LYS   133     -27.024   -7.309   -5.256  1.00  23.08      A
ATOM    153  CG   LYS   133     -27.684   -8.364   -4.354  1.00  21.07      A
ATOM    154  CD   LYS   133     -29.174   -8.110   -4.330  1.00  27.36      A
ATOM    155  CE   LYS   133     -29.939   -7.884   -5.670  1.00  30.56      A
ATOM    156  NZ   LYS   133     -31.323   -7.515   -5.345  1.00  21.56      A
ATOM    157  HZ1  LYS   133     -31.862   -7.351   -6.218  1.00  15.00      A
ATOM    158  HZ2  LYS   133     -31.753   -8.299   -4.811  1.00  15.00      A
ATOM    159  HZ3  LYS   133     -31.333   -6.654   -4.760  1.00  15.00      A
ATOM    160  C    LYS   133     -25.579   -6.876   -7.194  1.00  20.10      A
ATOM    161  O    LYS   133     -24.378   -6.801   -7.007  1.00  17.94      A
ATOM    162  N    THR   134     -26.260   -6.052   -7.983  1.00  22.95      A
ATOM    163  H    THR   134     -27.275   -6.130   -8.036  1.00  15.00      A
ATOM    164  CA   THR   134     -25.556   -4.879   -8.561  1.00  27.89      A
ATOM    165  CB   THR   134     -26.498   -4.274   -9.592  1.00  24.59      A
ATOM    166  OG1  THR   134     -26.540   -5.037  -10.792  1.00  24.32      A
ATOM    167  HG1  THR   134     -26.232   -4.411  -11.456  1.00  15.00      A
ATOM    168  CG2  THR   134     -26.044   -2.897   -9.968  1.00  22.97      A
ATOM    169  C    THR   134     -24.987   -3.798   -7.559  1.00  32.51      A
ATOM    170  O    THR   134     -25.658   -3.461   -6.603  1.00  38.43      A
ATOM    171  N    THR   135     -23.717   -3.352   -7.690  1.00  35.98      A
ATOM    172  H    THR   135     -23.292   -3.555   -8.585  1.00  15.00      A
ATOM    173  CA   THR   135     -22.964   -3.469   -6.386  1.00  36.02      A
ATOM    174  CB   THR   135     -21.575   -4.276   -6.534  1.00  36.01      A
ATOM    175  OG1  THR   135     -21.645   -5.388   -7.488  1.00  30.60      A
ATOM    176  HG1  THR   135     -22.255   -6.094   -7.312  1.00  15.00      A
ATOM    177  CG2  THR   135     -20.866   -4.776   -5.264  1.00  35.55      A
ATOM    178  C    THR   135     -22.949   -2.266   -5.404  1.00  30.25      A
ATOM    179  O    THR   135     -23.541   -2.348   -4.331  1.00  28.35      A
```

FIG.17D

| | | | | | | | | | | |
|---|---|---|---|---|---|---|---|---|---|---|
| ATOM | 180 | N | SER | 136 | -22.294 | -1.146 | -5.776 | 1.00 | 23.29 | A |
| ATOM | 181 | H | SER | 136 | -22.828 | -0.357 | -5.460 | 1.00 | 15.00 | A |
| ATOM | 182 | CA | SER | 136 | -20.857 | -1.051 | -6.143 | 1.00 | 23.04 | A |
| ATOM | 183 | CB | SER | 136 | -20.560 | 0.187 | -6.965 | 1.00 | 21.03 | A |
| ATOM | 184 | OG | SER | 136 | -20.624 | 1.261 | -6.043 | 1.00 | 28.21 | A |
| ATOM | 185 | HG | SER | 136 | -19.815 | 1.793 | -6.008 | 1.00 | 15.00 | A |
| ATOM | 186 | C | SER | 136 | -19.853 | -1.090 | -4.958 | 1.00 | 21.77 | A |
| ATOM | 187 | O | SER | 136 | -18.630 | -1.096 | -5.080 | 1.00 | 21.94 | A |
| ATOM | 188 | N | VAL | 137 | -20.452 | -1.227 | -3.752 | 1.00 | 24.03 | A |
| ATOM | 189 | H | VAL | 137 | -21.440 | -1.063 | -3.705 | 1.00 | 15.00 | A |
| ATOM | 190 | CA | VAL | 137 | -19.699 | -1.632 | -2.570 | 1.00 | 19.65 | A |
| ATOM | 191 | CB | VAL | 137 | -20.218 | -1.010 | -1.248 | 1.00 | 21.14 | A |
| ATOM | 192 | CG1 | VAL | 137 | -20.419 | -1.907 | -0.058 | 1.00 | 18.16 | A |
| ATOM | 193 | CG2 | VAL | 137 | -21.322 | -0.026 | -1.442 | 1.00 | 13.49 | A |
| ATOM | 194 | C | VAL | 137 | -19.370 | -3.116 | -2.473 | 1.00 | 17.15 | A |
| ATOM | 195 | O | VAL | 137 | -20.209 | -3.969 | -2.593 | 1.00 | 16.69 | A |
| ATOM | 196 | N | LEU | 138 | -18.077 | -3.344 | -2.271 | 1.00 | 15.84 | A |
| ATOM | 197 | H | LEU | 138 | -17.502 | -2.528 | -2.246 | 1.00 | 15.00 | A |
| ATOM | 198 | CA | LEU | 138 | -17.507 | -4.667 | -1.938 | 1.00 | 18.21 | A |
| ATOM | 199 | CB | LEU | 138 | -15.962 | -4.530 | -1.791 | 1.00 | 13.60 | A |
| ATOM | 200 | CG | LEU | 138 | -15.273 | -3.854 | -2.998 | 1.00 | 16.09 | A |
| ATOM | 201 | CD1 | LEU | 138 | -15.923 | -4.379 | -4.300 | 1.00 | 20.35 | A |
| ATOM | 202 | CD2 | LEU | 138 | -13.710 | -3.936 | -2.982 | 1.00 | 12.34 | A |
| ATOM | 203 | C | LEU | 138 | -18.170 | -5.480 | -0.772 | 1.00 | 16.29 | A |
| ATOM | 204 | O | LEU | 138 | -18.498 | -4.986 | 0.301 | 1.00 | 12.97 | A |
| ATOM | 205 | N | GLN | 139 | -18.345 | -6.768 | -1.035 | 1.00 | 13.04 | A |
| ATOM | 206 | H | GLN | 139 | -18.052 | -7.078 | -1.960 | 1.00 | 15.00 | A |
| ATOM | 207 | CA | GLN | 139 | -18.757 | -7.658 | 0.013 | 1.00 | 15.32 | A |
| ATOM | 208 | CB | GLN | 139 | -19.847 | -8.678 | -0.481 | 1.00 | 13.99 | A |
| ATOM | 209 | CG | GLN | 139 | -21.068 | -7.960 | -1.113 | 1.00 | 20.85 | A |
| ATOM | 210 | CD | GLN | 139 | -21.872 | -7.022 | -0.193 | 1.00 | 22.04 | A |
| ATOM | 211 | OE1 | GLN | 139 | -22.343 | -7.439 | 0.878 | 1.00 | 25.45 | A |
| ATOM | 212 | NE2 | GLN | 139 | -21.963 | -5.739 | -0.618 | 1.00 | 17.74 | A |
| ATOM | 213 | HE21 | GLN | 139 | -22.697 | -5.181 | -0.206 | 1.00 | 15.00 | A |
| ATOM | 214 | HE22 | GLN | 139 | -21.460 | -5.326 | -1.374 | 1.00 | 15.00 | A |
| ATOM | 215 | C | GLN | 139 | -17.527 | -8.383 | 0.541 | 1.00 | 14.26 | A |
| ATOM | 216 | O | GLN | 139 | -16.554 | -8.640 | -0.144 | 1.00 | 14.40 | A |
| ATOM | 217 | N | TRP | 140 | -17.647 | -8.780 | 1.805 | 1.00 | 12.80 | A |
| ATOM | 218 | H | TRP | 140 | -18.433 | -8.447 | 2.297 | 1.00 | 15.00 | A |
| ATOM | 219 | CA | TRP | 140 | -16.542 | -9.500 | 2.463 | 1.00 | 14.03 | A |
| ATOM | 220 | CB | TRP | 140 | -15.813 | -8.623 | 3.483 | 1.00 | 14.18 | A |
| ATOM | 221 | CG | TRP | 140 | -15.467 | -7.291 | 2.823 | 1.00 | 8.44 | A |
| ATOM | 222 | CD2 | TRP | 140 | -14.379 | -6.966 | 1.941 | 1.00 | 9.01 | A |
| ATOM | 223 | CE2 | TRP | 140 | -14.549 | -5.625 | 1.482 | 1.00 | 8.40 | A |
| ATOM | 224 | CE3 | TRP | 140 | -13.215 | -7.688 | 1.581 | 1.00 | 10.14 | A |
| ATOM | 225 | CD1 | TRP | 140 | -16.225 | -6.137 | 2.863 | 1.00 | 11.29 | A |
| ATOM | 226 | NE1 | TRP | 140 | -15.710 | -5.150 | 2.077 | 1.00 | 14.27 | A |
| ATOM | 227 | HE1 | TRP | 140 | -16.121 | -4.268 | 2.010 | 1.00 | 15.00 | A |
| ATOM | 228 | CZ2 | TRP | 140 | -13.640 | -5.009 | 0.590 | 1.00 | 8.16 | A |
| ATOM | 229 | CZ3 | TRP | 140 | -12.292 | -7.069 | 0.713 | 1.00 | 13.90 | A |
| ATOM | 230 | CH2 | TRP | 140 | -12.497 | -5.749 | 0.215 | 1.00 | 12.11 | A |
| ATOM | 231 | C | TRP | 140 | -17.016 | -10.701 | 3.170 | 1.00 | 14.34 | A |
| ATOM | 232 | O | TRP | 140 | -18.193 | -10.862 | 3.392 | 1.00 | 16.00 | A |
| ATOM | 233 | N | ALA | 141 | -16.082 | -11.528 | 3.558 | 1.00 | 14.80 | A |
| ATOM | 234 | H | ALA | 141 | -15.133 | -11.377 | 3.294 | 1.00 | 15.00 | A |
| ATOM | 235 | CA | ALA | 141 | -16.489 | -12.617 | 4.394 | 1.00 | 15.27 | A |
| ATOM | 236 | CB | ALA | 141 | -16.504 | -13.920 | 3.583 | 1.00 | 16.97 | A |
| ATOM | 237 | C | ALA | 141 | -15.585 | -12.761 | 5.607 | 1.00 | 15.90 | A |
| ATOM | 238 | O | ALA | 141 | -14.453 | -12.338 | 5.550 | 1.00 | 14.25 | A |
| ATOM | 239 | N | GLU | 142 | -16.068 | -13.366 | 6.688 | 1.00 | 19.74 | A |

FIG.17E

| | | | | | | | | | |
|---|---|---|---|---|---|---|---|---|---|
| ATOM | 240 | H | GLU | 142 | -17.055 | -13.574 | 6.688 | 1.00 15.00 | A |
| ATOM | 241 | CA | GLU | 142 | -15.149 | -13.759 | 7.731 | 1.00 25.93 | A |
| ATOM | 242 | CB | GLU | 142 | -15.794 | -13.910 | 9.117 | 1.00 21.75 | A |
| ATOM | 243 | CG | GLU | 142 | -15.716 | -12.456 | 9.647 | 1.00 24.05 | A |
| ATOM | 244 | CD | GLU | 142 | -16.749 | -12.087 | 10.711 | 1.00 26.61 | A |
| ATOM | 245 | OE1 | GLU | 142 | -17.908 | -11.888 | 10.361 | 1.00 34.72 | A |
| ATOM | 246 | OE2 | GLU | 142 | -16.404 | -11.984 | 11.886 | 1.00 30.07 | A |
| ATOM | 247 | C | GLU | 142 | -14.200 | -14.797 | 7.193 | 1.00 33.25 | A |
| ATOM | 248 | O | GLU | 142 | -13.156 | -14.349 | 6.737 | 1.00 41.84 | A |
| ATOM | 249 | N | LYS | 143 | -14.577 | -16.080 | 7.084 | 1.00 34.17 | A |
| ATOM | 250 | H | LYS | 143 | -15.432 | -16.384 | 7.492 | 1.00 15.00 | A |
| ATOM | 251 | CA | LYS | 143 | -13.882 | -16.854 | 5.980 | 1.00 35.31 | A |
| ATOM | 252 | CB | LYS | 143 | -14.673 | -16.603 | 4.681 | 1.00 37.64 | A |
| ATOM | 253 | CG | LYS | 143 | -14.300 | -17.505 | 3.531 | 1.00 47.37 | A |
| ATOM | 254 | CD | LYS | 143 | -15.022 | -17.284 | 2.202 | 1.00 50.37 | A |
| ATOM | 255 | CE | LYS | 143 | -14.686 | -16.047 | 1.357 | 1.00 49.23 | A |
| ATOM | 256 | NZ | LYS | 143 | -15.632 | -16.097 | 0.221 | 1.00 51.67 | A |
| ATOM | 257 | HZ1 | LYS | 143 | -15.333 | -15.445 | -0.534 | 1.00 15.00 | A |
| ATOM | 258 | HZ2 | LYS | 143 | -15.680 | -17.061 | -0.177 | 1.00 15.00 | A |
| ATOM | 259 | HZ3 | LYS | 143 | -16.564 | -15.833 | 0.585 | 1.00 15.00 | A |
| ATOM | 260 | C | LYS | 143 | -12.330 | -16.979 | 5.637 | 1.00 32.80 | A |
| ATOM | 261 | O | LYS | 143 | -11.831 | -18.041 | 5.276 | 1.00 35.64 | A |
| ATOM | 262 | N | GLY | 144 | -11.522 | -15.923 | 5.637 | 1.00 28.26 | A |
| ATOM | 263 | H | GLY | 144 | -11.718 | -14.995 | 5.910 | 1.00 15.00 | A |
| ATOM | 264 | CA | GLY | 144 | -10.243 | -16.458 | 5.194 | 1.00 32.94 | A |
| ATOM | 265 | C | GLY | 144 | -9.178 | -16.862 | 6.180 | 1.00 29.93 | A |
| ATOM | 266 | O | GLY | 144 | -9.345 | -17.454 | 7.205 | 1.00 24.67 | A |
| ATOM | 267 | N | TYR | 145 | -8.069 | -16.270 | 5.815 | 1.00 26.37 | A |
| ATOM | 268 | H | TYR | 145 | -8.160 | -15.729 | 4.966 | 1.00 15.00 | A |
| ATOM | 269 | CA | TYR | 145 | -7.027 | -16.002 | 6.777 | 1.00 27.61 | A |
| ATOM | 270 | CB | TYR | 145 | -5.708 | -15.877 | 5.947 | 1.00 37.54 | A |
| ATOM | 271 | CG | TYR | 145 | -5.962 | -15.774 | 4.456 | 1.00 50.95 | A |
| ATOM | 272 | CD1 | TYR | 145 | -5.682 | -14.633 | 3.706 | 1.00 53.22 | A |
| ATOM | 273 | CE1 | TYR | 145 | -6.313 | -14.377 | 2.468 | 1.00 60.28 | A |
| ATOM | 274 | CD2 | TYR | 145 | -6.591 | -16.847 | 3.791 | 1.00 53.11 | A |
| ATOM | 275 | CE2 | TYR | 145 | -7.207 | -16.699 | 2.551 | 1.00 56.30 | A |
| ATOM | 276 | CZ | TYR | 145 | -7.162 | -15.430 | 1.873 | 1.00 61.12 | A |
| ATOM | 277 | OH | TYR | 145 | -7.812 | -15.119 | 0.665 | 1.00 62.63 | A |
| ATOM | 278 | HH | TYR | 145 | -8.575 | -15.686 | 0.401 | 1.00 15.00 | A |
| ATOM | 279 | C | TYR | 145 | -7.532 | -14.762 | 7.620 | 1.00 22.41 | A |
| ATOM | 280 | O | TYR | 145 | -7.000 | -13.677 | 7.650 | 1.00 22.68 | A |
| ATOM | 281 | N | TYR | 146 | -8.731 | -14.884 | 8.196 | 1.00 20.39 | A |
| ATOM | 282 | H | TYR | 146 | -8.935 | -15.824 | 8.509 | 1.00 15.00 | A |
| ATOM | 283 | CA | TYR | 146 | -9.423 | -13.700 | 8.725 | 1.00 20.40 | A |
| ATOM | 284 | CB | TYR | 146 | -10.886 | -13.673 | 8.306 | 1.00 22.53 | A |
| ATOM | 285 | CG | TYR | 146 | -11.710 | -14.460 | 9.286 | 1.00 23.02 | A |
| ATOM | 286 | CD1 | TYR | 146 | -11.635 | -15.873 | 9.236 | 1.00 26.99 | A |
| ATOM | 287 | CE1 | TYR | 146 | -12.254 | -16.623 | 10.239 | 1.00 25.44 | A |
| ATOM | 288 | CD2 | TYR | 146 | -12.477 | -13.766 | 10.236 | 1.00 23.45 | A |
| ATOM | 289 | CE2 | TYR | 146 | -13.150 | -14.520 | 11.205 | 1.00 26.81 | A |
| ATOM | 290 | CZ | TYR | 146 | -13.007 | -15.937 | 11.204 | 1.00 27.40 | A |
| ATOM | 291 | OH | TYR | 146 | -13.647 | -16.689 | 12.170 | 1.00 31.91 | A |
| ATOM | 292 | HH | TYR | 146 | -12.911 | -17.080 | 12.676 | 1.00 15.00 | A |
| ATOM | 293 | C | TYR | 146 | -9.291 | -13.419 | 10.219 | 1.00 18.79 | A |
| ATOM | 294 | O | TYR | 146 | -8.904 | -14.232 | 11.012 | 1.00 16.13 | A |
| ATOM | 295 | N | THR | 147 | -9.596 | -12.169 | 10.556 | 1.00 17.54 | A |
| ATOM | 296 | H | THR | 147 | -9.973 | -11.607 | 9.830 | 1.00 15.00 | A |
| ATOM | 297 | CA | THR | 147 | -9.432 | -11.764 | 11.948 | 1.00 14.06 | A |
| ATOM | 298 | CB | THR | 147 | -8.162 | -10.875 | 12.182 | 1.00 13.66 | A |
| ATOM | 299 | OG1 | THR | 147 | -6.912 | -11.505 | 11.856 | 1.00 12.56 | A |

FIG. 17F

| ATOM | 300 | HG1 | THR | 147 | -6.934 | -11.898 | 10.980 | 1.00 | 15.00 | A |
|---|---|---|---|---|---|---|---|---|---|---|
| ATOM | 301 | CG2 | THR | 147 | -8.025 | -10.236 | 13.554 | 1.00 | 7.22 | A |
| ATOM | 302 | C | THR | 147 | -10.619 | -10.925 | 12.253 | 1.00 | 15.60 | A |
| ATOM | 303 | O | THR | 147 | -11.044 | -10.074 | 11.496 | 1.00 | 16.39 | A |
| ATOM | 304 | N | MET | 148 | -11.144 | -11.139 | 13.412 | 1.00 | 20.67 | A |
| ATOM | 305 | H | MET | 148 | -10.838 | -11.988 | 13.828 | 1.00 | 15.00 | A |
| ATOM | 306 | CA | MET | 148 | -12.124 | -10.311 | 14.110 | 1.00 | 19.71 | A |
| ATOM | 307 | CB | MET | 148 | -13.546 | -10.702 | 13.705 | 1.00 | 17.89 | A |
| ATOM | 308 | CG | MET | 148 | -14.541 | -9.580 | 14.019 | 1.00 | 13.53 | A |
| ATOM | 309 | SD | MET | 148 | -14.492 | -8.149 | 12.952 | 1.00 | 14.69 | A |
| ATOM | 310 | CE | MET | 148 | -14.566 | -8.928 | 11.333 | 1.00 | 10.10 | A |
| ATOM | 311 | C | MET | 148 | -11.915 | -10.282 | 15.639 | 1.00 | 21.49 | A |
| ATOM | 312 | O | MET | 148 | -12.594 | -10.905 | 16.436 | 1.00 | 22.98 | A |
| ATOM | 313 | N | SER | 149 | -10.955 | -9.412 | 16.055 | 1.00 | 20.58 | A |
| ATOM | 314 | H | SER | 149 | -10.516 | -8.786 | 15.406 | 1.00 | 15.00 | A |
| ATOM | 315 | CA | SER | 149 | -10.388 | -9.698 | 17.419 | 1.00 | 19.11 | A |
| ATOM | 316 | CB | SER | 149 | -9.174 | -8.860 | 17.792 | 1.00 | 12.17 | A |
| ATOM | 317 | OG | SER | 149 | -9.540 | -7.513 | 17.975 | 1.00 | 14.10 | A |
| ATOM | 318 | HG | SER | 149 | -9.571 | -7.487 | 18.934 | 1.00 | 15.00 | A |
| ATOM | 319 | C | SER | 149 | -11.203 | -9.844 | 18.727 | 1.00 | 22.19 | A |
| ATOM | 320 | O | SER | 149 | -10.728 | -10.267 | 19.772 | 1.00 | 22.95 | A |
| ATOM | 321 | N | ASN | 150 | -12.456 | -9.322 | 18.631 | 1.00 | 22.71 | A |
| ATOM | 322 | H | ASN | 150 | -12.782 | -9.247 | 17.688 | 1.00 | 15.00 | A |
| ATOM | 323 | CA | ASN | 150 | -13.361 | -9.236 | 19.764 | 1.00 | 20.32 | A |
| ATOM | 324 | CB | ASN | 150 | -12.734 | -8.446 | 20.955 | 1.00 | 21.56 | A |
| ATOM | 325 | CG | ASN | 150 | -12.343 | -6.962 | 20.706 | 1.00 | 20.71 | A |
| ATOM | 326 | OD1 | ASN | 150 | -13.059 | -6.187 | 20.119 | 1.00 | 17.81 | A |
| ATOM | 327 | ND2 | ASN | 150 | -11.222 | -6.485 | 21.271 | 1.00 | 23.86 | A |
| ATOM | 328 | HD21 | ASN | 150 | -11.035 | -5.521 | 21.092 | 1.00 | 15.00 | A |
| ATOM | 329 | HD22 | ASN | 150 | -10.670 | -7.109 | 21.821 | 1.00 | 15.00 | A |
| ATOM | 330 | C | ASN | 150 | -14.644 | -8.657 | 19.256 | 1.00 | 20.60 | A |
| ATOM | 331 | O | ASN | 150 | -14.718 | -8.130 | 18.148 | 1.00 | 20.56 | A |
| ATOM | 332 | N | ASN | 151 | -15.637 | -8.713 | 20.149 | 1.00 | 23.49 | A |
| ATOM | 333 | H | ASN | 151 | -15.455 | -9.124 | 21.038 | 1.00 | 15.00 | A |
| ATOM | 334 | CA | ASN | 151 | -16.974 | -8.080 | 19.823 | 1.00 | 24.71 | A |
| ATOM | 335 | CB | ASN | 151 | -18.130 | -8.645 | 20.712 | 1.00 | 28.30 | A |
| ATOM | 336 | CG | ASN | 151 | -17.959 | -8.271 | 22.173 | 1.00 | 33.23 | A |
| ATOM | 337 | OD1 | ASN | 151 | -17.075 | -7.562 | 22.606 | 1.00 | 39.79 | A |
| ATOM | 338 | ND2 | ASN | 151 | -18.782 | -8.838 | 23.011 | 1.00 | 38.32 | A |
| ATOM | 339 | HD21 | ASN | 151 | -18.553 | -8.524 | 23.928 | 1.00 | 15.00 | A |
| ATOM | 340 | HD22 | ASN | 151 | -19.495 | -9.465 | 22.733 | 1.00 | 15.00 | A |
| ATOM | 341 | C | ASN | 151 | -17.172 | -6.531 | 19.645 | 1.00 | 22.53 | A |
| ATOM | 342 | O | ASN | 151 | -18.254 | -6.048 | 19.374 | 1.00 | 21.32 | A |
| ATOM | 343 | N | LEU | 152 | -16.066 | -5.762 | 19.859 | 1.00 | 23.00 | A |
| ATOM | 344 | H | LEU | 152 | -15.247 | -6.289 | 20.070 | 1.00 | 15.00 | A |
| ATOM | 345 | CA | LEU | 152 | -15.924 | -4.335 | 19.525 | 1.00 | 18.87 | A |
| ATOM | 346 | CB | LEU | 152 | -14.830 | -3.700 | 20.325 | 1.00 | 21.77 | A |
| ATOM | 347 | CG | LEU | 152 | -14.981 | -3.999 | 21.806 | 1.00 | 24.80 | A |
| ATOM | 348 | CD1 | LEU | 152 | -16.390 | -3.645 | 22.316 | 1.00 | 22.82 | A |
| ATOM | 349 | CD2 | LEU | 152 | -13.847 | -3.256 | 22.556 | 1.00 | 23.56 | A |
| ATOM | 350 | C | LEU | 152 | -15.565 | -3.993 | 18.094 | 1.00 | 17.34 | A |
| ATOM | 351 | O | LEU | 152 | -15.590 | -2.840 | 17.708 | 1.00 | 13.39 | A |
| ATOM | 352 | N | VAL | 153 | -15.267 | -5.054 | 17.309 | 1.00 | 18.65 | A |
| ATOM | 353 | H | VAL | 153 | -15.156 | -5.962 | 17.716 | 1.00 | 15.00 | A |
| ATOM | 354 | CA | VAL | 153 | -15.439 | -4.910 | 15.849 | 1.00 | 16.81 | A |
| ATOM | 355 | CB | VAL | 153 | -14.138 | -5.021 | 14.980 | 1.00 | 15.33 | A |
| ATOM | 356 | CG1 | VAL | 153 | -12.908 | -5.718 | 15.562 | 1.00 | 21.22 | A |
| ATOM | 357 | CG2 | VAL | 153 | -13.775 | -3.757 | 14.287 | 1.00 | 16.95 | A |
| ATOM | 358 | C | VAL | 153 | -16.405 | -5.964 | 15.301 | 1.00 | 13.48 | A |
| ATOM | 359 | O | VAL | 153 | -16.363 | -7.116 | 15.647 | 1.00 | 13.06 | A |

FIG. 17G

| | | | | | | | | | | |
|---|---|---|---|---|---|---|---|---|---|---|
| ATOM | 360 | N | THR | 154 | -17.207 | -5.546 | 14.358 | 1.00 | 12.06 | A |
| ATOM | 361 | H | THR | 154 | -17.313 | -4.568 | 14.215 | 1.00 | 15.00 | A |
| ATOM | 362 | CA | THR | 154 | -17.903 | -6.600 | 13.615 | 1.00 | 16.26 | A |
| ATOM | 363 | CB | THR | 154 | -19.366 | -6.747 | 14.157 | 1.00 | 19.51 | A |
| ATOM | 364 | CG1 | THR | 154 | -19.995 | -5.459 | 14.205 | 1.00 | 19.31 | A |
| ATOM | 365 | HG1 | THR | 154 | -20.577 | -5.508 | 14.949 | 1.00 | 15.00 | A |
| ATOM | 366 | CG2 | THR | 154 | -19.502 | -7.288 | 15.571 | 1.00 | 21.62 | A |
| ATOM | 367 | C | THR | 154 | -17.997 | -6.252 | 12.107 | 1.00 | 18.12 | A |
| ATOM | 368 | O | THR | 154 | -17.992 | -5.110 | 11.605 | 1.00 | 16.55 | A |
| ATOM | 369 | N | LEU | 155 | -18.101 | -7.324 | 11.357 | 1.00 | 16.77 | A |
| ATOM | 370 | H | LEU | 155 | -18.056 | -8.202 | 11.791 | 1.00 | 15.00 | A |
| ATOM | 371 | CA | LEU | 155 | -18.514 | -7.198 | 9.967 | 1.00 | 17.10 | A |
| ATOM | 372 | CB | LEU | 155 | -17.829 | -8.353 | 9.204 | 1.00 | 20.04 | A |
| ATOM | 373 | CG | LEU | 155 | -17.524 | -8.428 | 7.692 | 1.00 | 20.81 | A |
| ATOM | 374 | CD1 | LEU | 155 | -17.822 | -7.159 | 6.908 | 1.00 | 17.03 | A |
| ATOM | 375 | CD2 | LEU | 155 | -17.912 | -9.810 | 7.139 | 1.00 | 12.42 | A |
| ATOM | 376 | C | LEU | 155 | -20.055 | -7.187 | 9.904 | 1.00 | 20.71 | A |
| ATOM | 377 | O | LEU | 155 | -20.712 | -8.163 | 10.217 | 1.00 | 18.01 | A |
| ATOM | 378 | N | GLU | 156 | -20.593 | -5.995 | 9.561 | 1.00 | 19.51 | A |
| ATOM | 379 | H | GLU | 156 | -19.959 | -5.230 | 9.440 | 1.00 | 15.00 | A |
| ATOM | 380 | CA | GLU | 156 | -22.036 | -5.888 | 9.413 | 1.00 | 21.95 | A |
| ATOM | 381 | CB | GLU | 156 | -22.641 | -4.631 | 10.033 | 1.00 | 18.95 | A |
| ATOM | 382 | CG | GLU | 156 | -22.098 | -4.412 | 11.436 | 1.00 | 27.68 | A |
| ATOM | 383 | CD | GLU | 156 | -22.721 | -5.194 | 12.587 | 1.00 | 31.62 | A |
| ATOM | 384 | OE1 | GLU | 156 | -23.347 | -6.248 | 12.367 | 1.00 | 33.40 | A |
| ATOM | 385 | OE2 | GLU | 156 | -22.532 | -4.721 | 13.724 | 1.00 | 35.00 | A |
| ATOM | 386 | C | GLU | 156 | -22.457 | -5.966 | 7.964 | 1.00 | 25.36 | A |
| ATOM | 387 | O | GLU | 156 | -21.958 | -5.298 | 7.077 | 1.00 | 22.70 | A |
| ATOM | 388 | N | ASN | 157 | -23.437 | -6.808 | 7.696 | 1.00 | 30.92 | A |
| ATOM | 389 | H | ASN | 157 | -23.594 | -7.590 | 8.300 | 1.00 | 15.00 | A |
| ATOM | 390 | CA | ASN | 157 | -23.804 | -6.620 | 6.300 | 1.00 | 33.31 | A |
| ATOM | 391 | CB | ASN | 157 | -23.856 | -7.970 | 5.614 | 1.00 | 31.69 | A |
| ATOM | 392 | CG | ASN | 157 | -23.669 | -7.693 | 4.168 | 1.00 | 27.70 | A |
| ATOM | 393 | OD1 | ASN | 157 | -23.397 | -6.593 | 3.810 | 1.00 | 25.89 | A |
| ATOM | 394 | ND2 | ASN | 157 | -23.893 | -8.640 | 3.275 | 1.00 | 41.69 | A |
| ATOM | 395 | HD21 | ASN | 157 | -24.069 | -9.603 | 3.467 | 1.00 | 15.00 | A |
| ATOM | 396 | HD22 | ASN | 157 | -23.745 | -8.295 | 2.340 | 1.00 | 15.00 | A |
| ATOM | 397 | C | ASN | 157 | -24.988 | -5.658 | 6.118 | 1.00 | 35.08 | A |
| ATOM | 398 | O | ASN | 157 | -26.107 | -5.949 | 6.499 | 1.00 | 37.06 | A |
| ATOM | 399 | N | GLY | 158 | -24.746 | -4.443 | 5.560 | 1.00 | 40.03 | A |
| ATOM | 400 | H | GLY | 158 | -25.601 | -3.952 | 5.429 | 1.00 | 15.00 | A |
| ATOM | 401 | CA | GLY | 158 | -23.422 | -3.887 | 5.121 | 1.00 | 38.11 | A |
| ATOM | 402 | C | GLY | 158 | -23.062 | -3.720 | 3.617 | 1.00 | 37.48 | A |
| ATOM | 403 | O | GLY | 158 | -23.890 | -3.108 | 2.950 | 1.00 | 41.11 | A |
| ATOM | 404 | N | LYS | 159 | -21.867 | -4.220 | 3.135 | 1.00 | 32.75 | A |
| ATOM | 405 | H | LYS | 159 | -21.904 | -4.134 | 2.130 | 1.00 | 15.00 | A |
| ATOM | 406 | CA | LYS | 159 | -20.828 | -4.928 | 3.962 | 1.00 | 27.83 | A |
| ATOM | 407 | CB | LYS | 159 | -20.317 | -6.122 | 3.217 | 1.00 | 28.17 | A |
| ATOM | 408 | CG | LYS | 159 | -19.734 | -7.168 | 4.069 | 1.00 | 20.48 | A |
| ATOM | 409 | CD | LYS | 159 | -20.533 | -8.426 | 4.192 | 1.00 | 29.61 | A |
| ATOM | 410 | CE | LYS | 159 | -20.577 | -9.191 | 2.869 | 1.00 | 40.41 | A |
| ATOM | 411 | NZ | LYS | 159 | -20.796 | -10.663 | 2.986 | 1.00 | 40.88 | A |
| ATOM | 412 | HZ1 | LYS | 159 | -20.739 | -11.087 | 2.035 | 1.00 | 15.00 | A |
| ATOM | 413 | HZ2 | LYS | 159 | -20.070 | -11.087 | 3.600 | 1.00 | 15.00 | A |
| ATOM | 414 | HZ3 | LYS | 159 | -21.738 | -10.848 | 3.389 | 1.00 | 15.00 | A |
| ATOM | 415 | C | LYS | 159 | -19.688 | -4.065 | 4.463 | 1.00 | 26.08 | A |
| ATOM | 416 | O | LYS | 159 | -19.023 | -3.369 | 3.696 | 1.00 | 28.01 | A |
| ATOM | 417 | N | GLN | 160 | -19.683 | -3.990 | 5.807 | 1.00 | 18.90 | A |
| ATOM | 418 | H | GLN | 160 | -20.211 | -4.674 | 6.319 | 1.00 | 15.00 | A |
| ATOM | 419 | CA | GLN | 160 | -18.922 | -2.929 | 6.464 | 1.00 | 13.89 | A |

FIG.17H

| | | | | | | | | | |
|---|---|---|---|---|---|---|---|---|---|
| ATOM | 420 | CB | GLN | 160 | -19.778 | -1.694 | 6.611 | 1.00 16.79 | A |
| ATOM | 421 | CG | GLN | 160 | -20.881 | -1.896 | 7.633 | 1.00 18.34 | A |
| ATOM | 422 | CD | GLN | 160 | -22.133 | -1.166 | 7.193 | 1.00 23.97 | A |
| ATOM | 423 | OE1 | GLN | 160 | -23.088 | -0.970 | 7.893 | 1.00 31.18 | A |
| ATOM | 424 | NE2 | GLN | 160 | -22.257 | -0.771 | 5.948 | 1.00 28.16 | A |
| ATOM | 425 | HE21 | GLN | 160 | -23.194 | -0.420 | 5.928 | 1.00 15.00 | A |
| ATOM | 426 | HE22 | GLN | 160 | -21.624 | -0.780 | 5.186 | 1.00 15.00 | A |
| ATOM | 427 | C | GLN | 160 | -18.313 | -3.309 | 7.777 | 1.00 12.87 | A |
| ATOM | 428 | O | GLN | 160 | -18.838 | -4.151 | 8.498 | 1.00 14.78 | A |
| ATOM | 429 | N | LEU | 161 | -17.187 | -2.637 | 8.085 | 1.00 11.22 | A |
| ATOM | 430 | H | LEU | 161 | -16.767 | -2.124 | 7.340 | 1.00 15.00 | A |
| ATOM | 431 | CA | LEU | 161 | -16.583 | -2.870 | 9.405 | 1.00 9.71 | A |
| ATOM | 432 | CB | LEU | 161 | -15.052 | -2.939 | 9.390 | 1.00 4.67 | A |
| ATOM | 433 | CG | LEU | 161 | -14.438 | -4.060 | 8.559 | 1.00 7.30 | A |
| ATOM | 434 | CD1 | LEU | 161 | -14.511 | -5.447 | 9.207 | 1.00 10.80 | A |
| ATOM | 435 | CD2 | LEU | 161 | -12.964 | -3.794 | 8.389 | 1.00 5.48 | A |
| ATOM | 436 | C | LEU | 161 | -17.082 | -1.836 | 10.412 | 1.00 10.17 | A |
| ATOM | 437 | O | LEU | 161 | -16.826 | -0.657 | 10.341 | 1.00 13.36 | A |
| ATOM | 438 | N | THR | 162 | -17.848 | -2.338 | 11.375 | 1.00 16.94 | A |
| ATOM | 439 | H | THR | 162 | -18.153 | -3.279 | 11.251 | 1.00 15.00 | A |
| ATOM | 440 | CA | THR | 162 | -18.317 | -1.480 | 12.493 | 1.00 16.14 | A |
| ATOM | 441 | CB | THR | 162 | -19.807 | -1.769 | 12.640 | 1.00 13.33 | A |
| ATOM | 442 | OG1 | THR | 162 | -20.339 | -1.707 | 11.308 | 1.00 16.73 | A |
| ATOM | 443 | HG1 | THR | 162 | -21.211 | -1.254 | 11.343 | 1.00 15.00 | A |
| ATOM | 444 | CG2 | THR | 162 | -20.553 | -0.832 | 13.562 | 1.00 15.01 | A |
| ATOM | 445 | C | THR | 162 | -17.531 | -1.547 | 13.842 | 1.00 13.28 | A |
| ATOM | 446 | O | THR | 162 | -17.358 | -2.587 | 14.449 | 1.00 20.21 | A |
| ATOM | 447 | N | VAL | 163 | -16.994 | -0.437 | 14.282 | 1.00 14.22 | A |
| ATOM | 448 | H | VAL | 163 | -16.859 | 0.243 | 13.567 | 1.00 15.00 | A |
| ATOM | 449 | CA | VAL | 163 | -16.326 | -0.358 | 15.586 | 1.00 15.72 | A |
| ATOM | 450 | CB | VAL | 163 | -15.038 | 0.426 | 15.428 | 1.00 11.82 | A |
| ATOM | 451 | CG1 | VAL | 163 | -15.191 | 1.944 | 15:368 | 1.00 9.87 | A |
| ATOM | 452 | CG2 | VAL | 163 | -14.229 | -0.124 | 14.245 | 1.00 18.88 | A |
| ATOM | 453 | C | VAL | 163 | -17.193 | 0.283 | 16.706 | 1.00 17.93 | A |
| ATOM | 454 | O | VAL | 163 | -18.001 | 1.180 | 16.453 | 1.00 20.25 | A |
| ATOM | 455 | N | LYS | 164 | -17.037 | -0.232 | 17.925 | 1.00 15.44 | A |
| ATOM | 456 | H | LYS | 164 | -16.254 | -0.858 | 18.020 | 1.00 15.00 | A |
| ATOM | 457 | CA | LYS | 164 | -17.856 | 0.138 | 19.109 | 1.00 17.33 | A |
| ATOM | 458 | CB | LYS | 164 | -18.351 | -1.150 | 19.807 | 1.00 19.58 | A |
| ATOM | 459 | CG | LYS | 164 | -19.214 | -1.885 | 18.759 | 1.00 23.56 | A |
| ATOM | 460 | CD | LYS | 164 | -19.417 | -3.410 | 18.851 | 1.00 28.85 | A |
| ATOM | 461 | CE | LYS | 164 | -20.039 | -4.047 | 17.554 | 1.00 33.81 | A |
| ATOM | 462 | NZ | LYS | 164 | -19.428 | -3.681 | 16.227 | 1.00 18.98 | A |
| ATOM | 463 | HZ1 | LYS | 164 | -19.195 | -2.667 | 16.222 | 1.00 15.00 | A |
| ATOM | 464 | HZ2 | LYS | 164 | -18.552 | -4.223 | 16.092 | 1.00 15.00 | A |
| ATOM | 465 | HZ3 | LYS | 164 | -20.084 | -3.888 | 15.445 | 1.00 15.00 | A |
| ATOM | 466 | C | LYS | 164 | -17.193 | 1.099 | 20.056 | 1.00 15.14 | A |
| ATOM | 467 | O | LYS | 164 | -17.712 | 1.588 | 21.048 | 1.00 17.72 | A |
| ATOM | 468 | N | ARG | 165 | -15.992 | 1.428 | 19.621 | 1.00 17.49 | A |
| ATOM | 469 | H | ARG | 165 | -15.550 | 0.838 | 18.932 | 1.00 15.00 | A |
| ATOM | 470 | CA | ARG | 165 | -15.184 | 2.415 | 20.325 | 1.00 20.18 | A |
| ATOM | 471 | CB | ARG | 165 | -13.985 | 1.806 | 21.049 | 1.00 24.65 | A |
| ATOM | 472 | CG | ARG | 165 | -14.363 | 0.833 | 22.126 | 1.00 29.54 | A |
| ATOM | 473 | CD | ARG | 165 | -13.274 | 1.077 | 23.145 | 1.00 38.82 | A |
| ATOM | 474 | NE | ARG | 165 | -13.719 | 1.998 | 24.186 | 1.00 43.41 | A |
| ATOM | 475 | HE | ARG | 165 | -14.331 | 1.671 | 24.908 | 1.00 15.00 | A |
| ATOM | 476 | CZ | ARG | 165 | -13.190 | 3.250 | 24.362 | 1.00 44.06 | A |
| ATOM | 477 | NH1 | ARG | 165 | -13.406 | 3.765 | 25.562 | 1.00 41.25 | A |
| ATOM | 478 | HH11 | ARG | 165 | -13.054 | 4.683 | 25.763 | 1.00 15.00 | A |
| ATOM | 479 | HH12 | ARG | 165 | -13.919 | 3.249 | 26.250 | 1.00 15.00 | A |

FIG. 171

| | | | | | | | | | |
|---|---|---|---|---|---|---|---|---|---|
| ATOM | 480 | NH2 | ARG | 165 | -12.485 | 3.946 | 23.425 | 1.00 31.65 | A |
| ATOM | 481 | HH21 | ARG | 165 | -12.133 | 4.860 | 23.623 | 1.00 15.00 | A |
| ATOM | 482 | HH22 | ARG | 165 | -12.322 | 3.527 | 22.530 | 1.00 15.00 | A |
| ATOM | 483 | C | ARG | 165 | -14.608 | 3.554 | 19.510 | 1.00 17.70 | A |
| ATOM | 484 | O | ARG | 165 | -14.018 | 3.450 | 18.441 | 1.00 18.26 | A |
| ATOM | 485 | N | GLN | 166 | -14.763 | 4.687 | 20.151 | 1.00 17.43 | A |
| ATOM | 486 | H | GLN | 166 | -15.263 | 4.614 | 21.007 | 1.00 15.00 | A |
| ATOM | 487 | CA | GLN | 166 | -14.138 | 5.911 | 19.698 | 1.00 19.00 | A |
| ATOM | 488 | CB | GLN | 166 | -14.613 | 7.021 | 20.610 | 1.00 23.79 | A |
| ATOM | 489 | CG | GLN | 166 | -14.067 | 8.409 | 20.386 | 1.00 34.06 | A |
| ATOM | 490 | CD | GLN | 166 | -15.178 | 9.399 | 20.659 | 1.00 45.91 | A |
| ATOM | 491 | OE1 | GLN | 166 | -15.102 | 10.492 | 20.135 | 1.00 53.64 | A |
| ATOM | 492 | NE2 | GLN | 166 | -16.202 | 9.046 | 21.418 | 1.00 44.10 | A |
| ATOM | 493 | HE21 | GLN | 166 | -16.906 | 9.765 | 21.443 | 1.00 15.00 | A |
| ATOM | 494 | HE22 | GLN | 166 | -16.577 | 8.287 | 21.935 | 1.00 15.00 | A |
| ATOM | 495 | C | GLN | 166 | -12.649 | 5.881 | 19.644 | 1.00 17.48 | A |
| ATOM | 496 | O | GLN | 166 | -12.029 | 5.378 | 20.561 | 1.00 18.13 | A |
| ATOM | 497 | N | GLY | 167 | -12.160 | 6.478 | 18.565 | 1.00 14.83 | A |
| ATOM | 498 | H | GLY | 167 | -12.750 | 6.836 | 17.850 | 1.00 15.00 | A |
| ATOM | 499 | CA | GLY | 167 | -10.728 | 6.711 | 18.557 | 1.00 16.28 | A |
| ATOM | 500 | C | GLY | 167 | -10.044 | 6.685 | 17.204 | 1.00 16.48 | A |
| ATOM | 501 | O | GLY | 167 | -10.674 | 6.601 | 16.162 | 1.00 19.19 | A |
| ATOM | 502 | N | LEU | 168 | -8.720 | 6.735 | 17.209 | 1.00 17.06 | A |
| ATOM | 503 | H | LEU | 168 | -8.311 | 6.890 | 18.120 | 1.00 15.00 | A |
| ATOM | 504 | CA | LEU | 168 | -7.925 | 6.625 | 15.992 | 1.00 16.60 | A |
| ATOM | 505 | CB | LEU | 168 | -6.600 | 7.343 | 16.289 | 1.00 21.87 | A |
| ATOM | 506 | CG | LEU | 168 | -6.247 | 8.745 | 15.716 | 1.00 22.69 | A |
| ATOM | 507 | CD1 | LEU | 168 | -5.119 | 9.410 | 16.539 | 1.00 21.20 | A |
| ATOM | 508 | CD2 | LEU | 168 | -7.436 | 9.617 | 15.361 | 1.00 18.38 | A |
| ATOM | 509 | C | LEU | 168 | -7.686 | 5.136 | 15.604 | 1.00 14.84 | A |
| ATOM | 510 | O | LEU | 168 | -7.282 | 4.278 | 16.392 | 1.00 15.89 | A |
| ATOM | 511 | N | TYR | 169 | -7.943 | 4.873 | 14.300 | 1.00 10.57 | A |
| ATOM | 512 | H | TYR | 169 | -8.313 | 5.659 | 13.807 | 1.00 15.00 | A |
| ATOM | 513 | CA | TYR | 169 | -7.683 | 3.572 | 13.656 | 1.00 5.27 | A |
| ATOM | 514 | CB | TYR | 169 | -8.989 | 3.014 | 13.230 | 1.00 5.83 | A |
| ATOM | 515 | CG | TYR | 169 | -9.857 | 2.620 | 14.423 | 1.00 6.94 | A |
| ATOM | 516 | CD1 | TYR | 169 | -10.524 | 3.598 | 15.168 | 1.00 7.40 | A |
| ATOM | 517 | CE1 | TYR | 169 | -11.390 | 3.193 | 16.218 | 1.00 7.77 | A |
| ATOM | 518 | CD2 | TYR | 169 | -10.016 | 1.255 | 14.744 | 1.00 8.89 | A |
| ATOM | 519 | CE2 | TYR | 169 | -10.850 | 0.841 | 15.804 | 1.00 9.40 | A |
| ATOM | 520 | CZ | TYR | 169 | -11.563 | 1.827 | 16.534 | 1.00 10.39 | A |
| ATOM | 521 | OH | TYR | 169 | -12.443 | 1.410 | 17.534 | 1.00 7.99 | A |
| ATOM | 522 | HH | TYR | 169 | -13.009 | 2.117 | 17.800 | 1.00 15.00 | A |
| ATOM | 523 | C | TYR | 169 | -6.810 | 3.642 | 12.390 | 1.00 6.72 | A |
| ATOM | 524 | O | TYR | 169 | -6.917 | 4.498 | 11.557 | 1.00 9.12 | A |
| ATOM | 525 | N | TYR | 170 | -5.899 | 2.722 | 12.228 | 1.00 9.53 | A |
| ATOM | 526 | H | TYR | 170 | -5.806 | 2.081 | 12.986 | 1.00 15.00 | A |
| ATOM | 527 | CA | TYR | 170 | -5.313 | 2.511 | 10.899 | 1.00 10.01 | A |
| ATOM | 528 | CB | TYR | 170 | -3.967 | 1.797 | 11.044 | 1.00 7.46 | A |
| ATOM | 529 | CG | TYR | 170 | -3.259 | 1.636 | 9.679 | 1.00 13.45 | A |
| ATOM | 530 | CD1 | TYR | 170 | -2.680 | 2.766 | 9.052 | 1.00 12.66 | A |
| ATOM | 531 | CE1 | TYR | 170 | -2.213 | 2.658 | 7.738 | 1.00 10.18 | A |
| ATOM | 532 | CD2 | TYR | 170 | -3.304 | 0.385 | 9.057 | 1.00 10.90 | A |
| ATOM | 533 | CE2 | TYR | 170 | -2.891 | 0.303 | 7.730 | 1.00 8.68 | A |
| ATOM | 534 | CZ | TYR | 170 | -2.331 | 1.419 | 7.124 | 1.00 9.97 | A |
| ATOM | 535 | OH | TYR | 170 | -1.774 | 1.286 | 5.859 | 1.00 17.50 | A |
| ATOM | 536 | HH | TYR | 170 | -1.886 | 0.404 | 5.514 | 1.00 15.00 | A |
| ATOM | 537 | C | TYR | 170 | -6.279 | 1.610 | 10.073 | 1.00 10.40 | A |
| ATOM | 538 | O | TYR | 170 | -6.679 | 0.500 | 10.421 | 1.00 12.52 | A |
| ATOM | 539 | N | ILE | 171 | -6.704 | 2.174 | 8.968 | 1.00 12.16 | A |

FIG. 17J

| ATOM | 540 | H | ILE | 171 | -6.475 | 3.135 | 8.808 | 1.00 | 15.00 | A |
|---|---|---|---|---|---|---|---|---|---|---|
| ATOM | 541 | CA | ILE | 171 | -7.608 | 1.430 | 8.138 | 1.00 | 9.37 | A |
| ATOM | 542 | CB | ILE | 171 | -9.070 | 1.990 | 8.317 | 1.00 | 11.21 | A |
| ATOM | 543 | CG2 | ILE | 171 | -9.326 | 3.501 | 8.677 | 1.00 | 17.27 | A |
| ATOM | 544 | CG1 | ILE | 171 | -10.046 | 1.564 | 7.214 | 1.00 | 13.33 | A |
| ATOM | 545 | CD1 | ILE | 171 | -10.647 | 0.250 | 7.619 | 1.00 | 17.53 | A |
| ATOM | 546 | C | ILE | 171 | -7.074 | 1.234 | 6.694 | 1.00 | 8.34 | A |
| ATOM | 547 | O | ILE | 171 | -6.453 | 2.088 | 6.082 | 1.00 | 6.96 | A |
| ATOM | 548 | N | TYR | 172 | -7.286 | 0.005 | 6.216 | 1.00 | 11.07 | A |
| ATOM | 549 | H | TYR | 172 | -7.809 | -0.624 | 6.786 | 1.00 | 15.00 | A |
| ATOM | 550 | CA | TYR | 172 | -6.708 | -0.378 | 4.922 | 1.00 | 15.60 | A |
| ATOM | 551 | CB | TYR | 172 | -5.332 | -1.082 | 5.037 | 1.00 | 14.32 | A |
| ATOM | 552 | CG | TYR | 172 | -5.389 | -2.397 | 5.796 | 1.00 | 9.21 | A |
| ATOM | 553 | CD1 | TYR | 172 | -5.342 | -2.402 | 7.216 | 1.00 | 12.52 | A |
| ATOM | 554 | CE1 | TYR | 172 | -5.607 | -3.620 | 7.901 | 1.00 | 10.88 | A |
| ATOM | 555 | CD2 | TYR | 172 | -5.565 | -3.586 | 5.050 | 1.00 | 12.66 | A |
| ATOM | 556 | CE2 | TYR | 172 | -5.829 | -4.800 | 5.740 | 1.00 | 15.83 | A |
| ATOM | 557 | CZ | TYR | 172 | -5.822 | -4.808 | 7.164 | 1.00 | 11.94 | A |
| ATOM | 558 | OH | TYR | 172 | -5.995 | -6.002 | 7.820 | 1.00 | 12.17 | A |
| ATOM | 559 | HH | TYR | 172 | -6.433 | -5.843 | 8.657 | 1.00 | 15.00 | A |
| ATOM | 560 | C | TYR | 172 | -7.605 | -1.276 | 4.106 | 1.00 | 16.85 | A |
| ATOM | 561 | O | TYR | 172 | -8.346 | -2.057 | 4.692 | 1.00 | 14.06 | A |
| ATOM | 562 | N | ALA | 173 | -7.448 | -1.141 | 2.776 | 1.00 | 16.29 | A |
| ATOM | 563 | H | ALA | 173 | -6.751 | -0.490 | 2.503 | 1.00 | 15.00 | A |
| ATOM | 564 | CA | ALA | 173 | -7.940 | -2.152 | 1.836 | 1.00 | 15.11 | A |
| ATOM | 565 | CB | ALA | 173 | -9.300 | -1.725 | 1.292 | 1.00 | 12.08 | A |
| ATOM | 566 | C | ALA | 173 | -7.007 | -2.537 | 0.653 | 1.00 | 15.86 | A |
| ATOM | 567 | O | ALA | 173 | -6.147 | -1.806 | 0.191 | 1.00 | 14.20 | A |
| ATOM | 568 | N | GLN | 174 | -7.244 | -3.714 | 0.109 | 1.00 | 16.56 | A |
| ATOM | 569 | H | GLN | 174 | -7.774 | -4.389 | 0.620 | 1.00 | 15.00 | A |
| ATOM | 570 | CA | GLN | 174 | -6.470 | -4.119 | -1.070 | 1.00 | 19.25 | A |
| ATOM | 571 | CB | GLN | 174 | -5.582 | -5.292 | -0.832 | 1.00 | 21.99 | A |
| ATOM | 572 | CG | GLN | 174 | -4.205 | -4.727 | -1.030 | 1.00 | 30.99 | A |
| ATOM | 573 | CD | GLN | 174 | -3.174 | -5.845 | -0.979 | 1.00 | 34.25 | A |
| ATOM | 574 | OE1 | GLN | 174 | -2.308 | -5.899 | -0.105 | 1.00 | 32.91 | A |
| ATOM | 575 | NE2 | GLN | 174 | -3.268 | -6.699 | -2.014 | 1.00 | 31.50 | A |
| ATOM | 576 | HE21 | GLN | 174 | -2.668 | -7.487 | -1.970 | 1.00 | 15.00 | A |
| ATOM | 577 | HE22 | GLN | 174 | -3.973 | -6.621 | -2.714 | 1.00 | 15.00 | A |
| ATOM | 578 | C | GLN | 174 | -7.413 | -4.644 | -2.114 | 1.00 | 19.20 | A |
| ATOM | 579 | O | GLN | 174 | -8.285 | -5.434 | -1.880 | 1.00 | 20.03 | A |
| ATOM | 580 | N | VAL | 175 | -7.291 | -4.107 | -3.301 | 1.00 | 19.28 | A |
| ATOM | 581 | H | VAL | 175 | -6.594 | -3.401 | -3.400 | 1.00 | 15.00 | A |
| ATOM | 582 | CA | VAL | 175 | -8.247 | -4.500 | -4.323 | 1.00 | 22.43 | A |
| ATOM | 583 | CB | VAL | 175 | -9.319 | -3.409 | -4.644 | 1.00 | 21.41 | A |
| ATOM | 584 | CG1 | VAL | 175 | -10.146 | -2.830 | -3.495 | 1.00 | 20.17 | A |
| ATOM | 585 | CG2 | VAL | 175 | -10.268 | -4.061 | -5.639 | 1.00 | 22.88 | A |
| ATOM | 586 | C | VAL | 175 | -7.508 | -4.859 | -5.615 | 1.00 | 24.56 | A |
| ATOM | 587 | O | VAL | 175 | -6.928 | -3.997 | -6.301 | 1.00 | 23.28 | A |
| ATOM | 588 | N | THR | 176 | -7.563 | -6.180 | -5.879 | 1.00 | 25.40 | A |
| ATOM | 589 | H | THR | 176 | -7.994 | -6.850 | -5.250 | 1.00 | 15.00 | A |
| ATOM | 590 | CA | THR | 176 | -7.086 | -6.501 | -7.222 | 1.00 | 24.46 | A |
| ATOM | 591 | CB | THR | 176 | -5.844 | -7.454 | -7.256 | 1.00 | 24.78 | A |
| ATOM | 592 | OG1 | THR | 176 | -5.948 | -8.650 | -8.028 | 1.00 | 20.31 | A |
| ATOM | 593 | HG1 | THR | 176 | -5.250 | -9.253 | -7.796 | 1.00 | 15.00 | A |
| ATOM | 594 | CG2 | THR | 176 | -5.329 | -7.711 | -5.867 | 1.00 | 17.07 | A |
| ATOM | 595 | C | THR | 176 | -8.178 | -6.700 | -8.272 | 1.00 | 25.44 | A |
| ATOM | 596 | O | THR | 176 | -9.326 | -7.043 | -7.995 | 1.00 | 26.86 | A |
| ATOM | 597 | N | PHE | 177 | -7.855 | -6.341 | -9.506 | 1.00 | 22.44 | A |
| ATOM | 598 | H | PHE | 177 | -6.920 | -6.083 | -9.732 | 1.00 | 15.00 | A |
| ATOM | 599 | CA | PHE | 177 | -8.939 | -6.511 | -10.479 | 1.00 | 22.70 | A |

FIG. 17K

| | | | | | | | | | |
|---|---|---|---|---|---|---|---|---|---|
| ATOM | 600 | CB | PHE | 177 | -9.746 | -5.194 | -10.599 | 1.00 20.90 | A |
| ATOM | 601 | CG | PHE | 177 | -8.813 | -4.034 | -10.927 | 1.00 22.51 | A |
| ATOM | 602 | CD1 | PHE | 177 | -8.771 | -3.548 | -12.252 | 1.00 22.11 | A |
| ATOM | 603 | CD2 | PHE | 177 | -8.011 | -3.422 | -9.920 | 1.00 21.87 | A |
| ATOM | 604 | CE1 | PHE | 177 | -8.041 | -2.387 | -12.550 | 1.00 20.53 | A |
| ATOM | 605 | CE2 | PHE | 177 | -7.289 | -2.247 | -10.204 | 1.00 20.44 | A |
| ATOM | 606 | CZ | PHE | 177 | -7.376 | -1.713 | -11.500 | 1.00 22.79 | A |
| ATOM | 607 | C | PHE | 177 | -8.381 | -6.949 | -11.800 | 1.00 22.14 | A |
| ATOM | 608 | O | PHE | 177 | -7.219 | -6.695 | -12.072 | 1.00 21.60 | A |
| ATOM | 609 | N | CYS | 178 | -9.210 | -7.555 | -12.625 | 1.00 24.52 | A |
| ATOM | 610 | H | CYS | 178 | -10.146 | -7.797 | -12.370 | 1.00 15.00 | A |
| ATOM | 611 | CA | CYS | 178 | -8.599 | -7.849 | -13.942 | 1.00 29.77 | A |
| ATOM | 612 | CB | CYS | 178 | -8.501 | -9.365 | -14.214 | 1.00 32.06 | A |
| ATOM | 613 | SG | CYS | 178 | -7.685 | -9.731 | -15.792 | 1.00 35.17 | A |
| ATOM | 614 | C | CYS | 178 | -9.323 | -7.146 | -15.088 | 1.00 28.41 | A |
| ATOM | 615 | O | CYS | 178 | -10.534 | -7.247 | -15.185 | 1.00 27.54 | A |
| ATOM | 616 | N | SER | 179 | -8.589 | -6.393 | -15.910 | 1.00 28.86 | A |
| ATOM | 617 | H | SER | 179 | -7.608 | -6.271 | -15.754 | 1.00 15.00 | A |
| ATOM | 618 | CA | SER | 179 | -9.374 | -5.454 | -16.704 | 1.00 29.01 | A |
| ATOM | 619 | CB | SER | 179 | -9.379 | -4.118 | -16.020 | 1.00 30.82 | A |
| ATOM | 620 | OG | SER | 179 | -10.615 | -3.492 | -16.319 | 1.00 39.79 | A |
| ATOM | 621 | HG | SER | 179 | -10.725 | -2.812 | -15.667 | 1.00 15.00 | A |
| ATOM | 622 | C | SER | 179 | -9.063 | -5.196 | -18.165 | 1.00 31.16 | A |
| ATOM | 623 | O | SER | 179 | -7.931 | -4.953 | -18.537 | 1.00 28.58 | A |
| ATOM | 624 | N | ASN | 180 | -10.083 | -5.255 | -19.042 | 1.00 35.32 | A |
| ATOM | 625 | H | ASN | 180 | -10.966 | -5.700 | -18.834 | 1.00 15.00 | A |
| ATOM | 626 | CA | ASN | 180 | -9.782 | -4.725 | -20.366 | 1.00 34.74 | A |
| ATOM | 627 | CB | ASN | 180 | -10.205 | -5.554 | -21.589 | 1.00 37.96 | A |
| ATOM | 628 | CG | ASN | 180 | -9.650 | -4.980 | -22.896 | 1.00 37.12 | A |
| ATOM | 629 | OD1 | ASN | 180 | -10.058 | -3.947 | -23.356 | 1.00 40.66 | A |
| ATOM | 630 | ND2 | ASN | 180 | -8.619 | -5.536 | -23.456 | 1.00 35.85 | A |
| ATOM | 631 | HD21 | ASN | 180 | -8.343 | -6.475 | -23.306 | 1.00 15.00 | A |
| ATOM | 632 | HD22 | ASN | 180 | -8.153 | -4.891 | -24.065 | 1.00 15.00 | A |
| ATOM | 633 | C | ASN | 180 | -10.197 | -3.331 | -20.588 | 1.00 36.96 | A |
| ATOM | 634 | O | ASN | 180 | -11.314 | -2.894 | -20.433 | 1.00 37.89 | A |
| ATOM | 635 | N | ARG | 181 | -9.147 | -2.699 | -21.068 | 1.00 41.95 | A |
| ATOM | 636 | H | ARG | 181 | -8.363 | -3.318 | -21.141 | 1.00 15.00 | A |
| ATOM | 637 | CA | ARG | 181 | -8.997 | -1.313 | -21.489 | 1.00 44.24 | A |
| ATOM | 638 | CB | ARG | 181 | -7.563 | -1.279 | -22.026 | 1.00 43.43 | A |
| ATOM | 639 | CG | ARG | 181 | -6.348 | -1.638 | -21.101 | 1.00 45.11 | A |
| ATOM | 640 | CD | ARG | 181 | -6.235 | -2.853 | -20.134 | 1.00 40.68 | A |
| ATOM | 641 | NE | ARG | 181 | -5.064 | -2.772 | -19.271 | 1.00 46.11 | A |
| ATOM | 642 | HE | ARG | 181 | -4.991 | -2.058 | -18.578 | 1.00 15.00 | A |
| ATOM | 643 | CZ | ARG | 181 | -4.024 | -3.611 | -19.432 | 1.00 49.77 | A |
| ATOM | 644 | NH1 | ARG | 181 | -2.886 | -3.414 | -18.790 | 1.00 54.33 | A |
| ATOM | 645 | HH11 | ARG | 181 | -2.113 | -4.032 | -18.918 | 1.00 15.00 | A |
| ATOM | 646 | HH12 | ARG | 181 | -2.807 | -2.642 | -18.161 | 1.00 15.00 | A |
| ATOM | 647 | NH2 | ARG | 181 | -4.085 | -4.641 | -20.247 | 1.00 54.26 | A |
| ATOM | 648 | HH21 | ARG | 181 | -3.286 | -5.230 | -20.354 | 1.00 15.00 | A |
| ATOM | 649 | HH22 | ARG | 181 | -4.918 | -4.833 | -20.761 | 1.00 15.00 | A |
| ATOM | 650 | C | ARG | 181 | -10.049 | -0.866 | -22.499 | 1.00 47.10 | A |
| ATOM | 651 | O | ARG | 181 | -10.979 | -0.112 | -22.227 | 1.00 49.20 | A |
| ATOM | 652 | N | GLU | 182 | -9.895 | -1.447 | -23.690 | 1.00 49.64 | A |
| ATOM | 653 | H | GLU | 182 | -9.201 | -2.166 | -23.775 | 1.00 15.00 | A |
| ATOM | 654 | CA | GLU | 182 | -10.976 | -1.385 | -24.676 | 1.00 52.41 | A |
| ATOM | 655 | CB | GLU | 182 | -10.437 | -2.020 | -25.970 | 1.00 56.93 | A |
| ATOM | 656 | CG | GLU | 182 | -10.932 | -1.418 | -27.295 | 1.00 66.05 | A |
| ATOM | 657 | CD | GLU | 182 | -10.758 | 0.116 | -27.327 | 1.00 70.54 | A |
| ATOM | 658 | OE1 | GLU | 182 | -9.613 | 0.586 | -27.442 | 1.00 72.98 | A |
| ATOM | 659 | OE2 | GLU | 182 | -11.778 | 0.830 | -27.244 | 1.00 72.46 | A |

FIG.17L

| | | | | | | | | | |
|---|---|---|---|---|---|---|---|---|---|
| ATOM | 660 | C | GLU | 182 | -12.388 | -1.934 | -24.304 | 1.00 53.00 | A |
| ATOM | 661 | O | GLU | 182 | -13.379 | -1.492 | -24.862 | 1.00 54.27 | A |
| ATOM | 662 | N | ALA | 183 | -12.505 | -2.877 | -23.335 | 1.00 52.34 | A |
| ATOM | 663 | H | ALA | 183 | -11.676 | -3.173 | -22.865 | 1.00 15.00 | A |
| ATOM | 664 | CA | ALA | 183 | -13.867 | -3.258 | -22.899 | 1.00 50.19 | A |
| ATOM | 665 | CB | ALA | 183 | -13.855 | -4.721 | -22.447 | 1.00 45.02 | A |
| ATOM | 666 | C | ALA | 183 | -14.562 | -2.321 | -21.867 | 1.00 50.66 | A |
| ATOM | 667 | O | ALA | 183 | -15.712 | -1.945 | -21.990 | 1.00 47.77 | A |
| ATOM | 668 | N | SER | 184 | -13.773 | -1.888 | -20.878 | 1.00 52.95 | A |
| ATOM | 669 | H | SER | 184 | -12.826 | -2.172 | -20.991 | 1.00 15.00 | A |
| ATOM | 670 | CA | SER | 184 | -14.228 | -1.043 | -19.729 | 1.00 56.78 | A |
| ATOM | 671 | CB | SER | 184 | -13.384 | -1.397 | -18.481 | 1.00 53.58 | A |
| ATOM | 672 | OG | SER | 184 | -13.975 | -2.448 | -17.721 | 1.00 47.46 | A |
| ATOM | 673 | HG | SER | 184 | -13.291 | -3.019 | -17.388 | 1.00 15.00 | A |
| ATOM | 674 | C | SER | 184 | -14.183 | 0.517 | -19.880 | 1.00 59.95 | A |
| ATOM | 675 | O | SER | 184 | -13.913 | 1.297 | -18.964 | 1.00 65.25 | A |
| ATOM | 676 | N | SER | 185 | -14.324 | 0.995 | -21.131 | 1.00 60.08 | A |
| ATOM | 677 | H | SER | 185 | -14.623 | 0.345 | -21.831 | 1.00 15.00 | A |
| ATOM | 678 | CA | SER | 185 | -13.825 | 2.375 | -21.391 | 1.00 60.12 | A |
| ATOM | 679 | CB | SER | 185 | -13.522 | 2.640 | -22.869 | 1.00 60.49 | A |
| ATOM | 680 | OG | SER | 185 | -12.243 | 2.098 | -23.242 | 1.00 59.80 | A |
| ATOM | 681 | HG | SER | 185 | -12.158 | 1.234 | -22.833 | 1.00 15.00 | A |
| ATOM | 682 | C | SER | 185 | -14.580 | 3.589 | -20.885 | 1.00 59.59 | A |
| ATOM | 683 | O | SER | 185 | -15.437 | 4.159 | -21.543 | 1.00 60.08 | A |
| ATOM | 684 | N | GLN | 186 | -14.200 | 3.990 | -19.670 | 1.00 57.71 | A |
| ATOM | 685 | H | GLN | 186 | -13.601 | 3.376 | -19.153 | 1.00 15.00 | A |
| ATOM | 686 | CA | GLN | 186 | -15.121 | 4.936 | -18.993 | 1.00 57.00 | A |
| ATOM | 687 | CB | GLN | 186 | -16.094 | 4.062 | -18.175 | 1.00 58.66 | A |
| ATOM | 688 | CG | GLN | 186 | -15.355 | 3.354 | -17.050 | 1.00 59.69 | A |
| ATOM | 689 | CD | GLN | 186 | -16.369 | 2.789 | -16.088 | 1.00 59.92 | A |
| ATOM | 690 | OE1 | GLN | 186 | -17.270 | 3.513 | -15.687 | 1.00 59.81 | A |
| ATOM | 691 | NE2 | GLN | 186 | -16.249 | 1.503 | -15.787 | 1.00 59.63 | A |
| ATOM | 692 | HE21 | GLN | 186 | -15.492 | 0.948 | -16.113 | 1.00 15.00 | A |
| ATOM | 693 | HE22 | GLN | 186 | -16.950 | 1.119 | -15.168 | 1.00 15.00 | A |
| ATOM | 694 | C | GLN | 186 | -14.758 | 6.290 | -18.221 | 1.00 54.36 | A |
| ATOM | 695 | O | GLN | 186 | -15.596 | 7.198 | -18.298 | 1.00 53.98 | A |
| ATOM | 696 | N | ALA | 187 | -13.566 | 6.424 | -17.511 | 1.00 50.35 | A |
| ATOM | 697 | H | ALA | 187 | -13.476 | 7.274 | -16.970 | 1.00 15.00 | A |
| ATOM | 698 | CA | ALA | 187 | -12.388 | 5.599 | -17.832 | 1.00 43.26 | A |
| ATOM | 699 | CB | ALA | 187 | -11.546 | 6.284 | -18.918 | 1.00 38.95 | A |
| ATOM | 700 | C | ALA | 187 | -11.456 | 4.882 | -16.849 | 1.00 40.48 | A |
| ATOM | 701 | O | ALA | 187 | -10.887 | 3.875 | -17.295 | 1.00 43.24 | A |
| ATOM | 702 | N | PRO | 188 | -11.210 | 5.383 | -15.594 | 1.00 38.66 | A |
| ATOM | 703 | CD | PRO | 188 | -11.543 | 6.687 | -15.000 | 1.00 38.15 | A |
| ATOM | 704 | CA | PRO | 188 | -10.220 | 4.665 | -14.751 | 1.00 35.94 | A |
| ATOM | 705 | CB | PRO | 188 | -9.395 | 5.813 | -14.150 | 1.00 33.99 | A |
| ATOM | 706 | CG | PRO | 188 | -10.377 | 7.000 | -14.036 | 1.00 32.69 | A |
| ATOM | 707 | C | PRO | 188 | -10.840 | 3.783 | -13.683 | 1.00 33.66 | A |
| ATOM | 708 | O | PRO | 188 | -11.885 | 4.062 | -13.140 | 1.00 33.41 | A |
| ATOM | 709 | N | PHE | 189 | -10.147 | 2.695 | -13.346 | 1.00 28.66 | A |
| ATOM | 710 | H | PHE | 189 | -9.260 | 2.508 | -13.748 | 1.00 15.00 | A |
| ATOM | 711 | CA | PHE | 189 | -10.721 | 2.013 | -12.171 | 1.00 26.71 | A |
| ATOM | 712 | CB | PHE | 189 | -10.122 | 0.601 | -12.034 | 1.00 26.21 | A |
| ATOM | 713 | CG | PHE | 189 | -10.671 | -0.189 | -10.849 | 1.00 22.92 | A |
| ATOM | 714 | CD1 | PHE | 189 | -10.126 | 0.005 | -9.566 | 1.00 17.72 | A |
| ATOM | 715 | CD2 | PHE | 189 | -11.687 | -1.165 | -11.064 | 1.00 21.88 | A |
| ATOM | 716 | CE1 | PHE | 189 | -10.590 | -0.815 | -8.522 | 1.00 19.12 | A |
| ATOM | 717 | CE2 | PHE | 189 | -12.124 | -1.995 | -10.011 | 1.00 21.13 | A |
| ATOM | 718 | CZ | PHE | 189 | -11.571 | -1.806 | -8.736 | 1.00 18.44 | A |
| ATOM | 719 | C | PHE | 189 | -10.445 | 2.815 | -10.909 | 1.00 27.14 | A |

FIG. 17M

| | | | | | | | | | | |
|---|---|---|---|---|---|---|---|---|---|---|
| ATOM | 720 | O | PHE | 189 | -9.308 | 3.244 | -10.706 | 1.00 | 28.72 | A |
| ATOM | 721 | N | ILE | 190 | -11.468 | 2.964 | -10.071 | 1.00 | 24.71 | A |
| ATOM | 722 | H | ILE | 190 | -12.408 | 2.786 | -10.388 | 1.00 | 15.00 | A |
| ATOM | 723 | CA | ILE | 190 | -11.193 | 3.626 | -8.788 | 1.00 | 24.03 | A |
| ATOM | 724 | CB | ILE | 190 | -11.316 | 5.242 | -8.743 | 1.00 | 26.86 | A |
| ATOM | 725 | CG2 | ILE | 190 | -11.892 | 5.979 | -9.997 | 1.00 | 19.87 | A |
| ATOM | 726 | CG1 | ILE | 190 | -11.801 | 5.888 | -7.424 | 1.00 | 22.54 | A |
| ATOM | 727 | CD1 | ILE | 190 | -12.819 | 7.012 | -7.645 | 1.00 | 28.56 | A |
| ATOM | 728 | C | ILE | 190 | -11.844 | 2.812 | -7.656 | 1.00 | 21.97 | A |
| ATOM | 729 | O | ILE | 190 | -12.891 | 2.197 | -7.801 | 1.00 | 16.30 | A |
| ATOM | 730 | N | ALA | 191 | -11.026 | 2.700 | -6.590 | 1.00 | 17.21 | A |
| ATOM | 731 | H | ALA | 191 | -10.124 | 3.124 | -6.662 | 1.00 | 15.00 | A |
| ATOM | 732 | CA | ALA | 191 | -11.501 | 2.195 | -5.321 | 1.00 | 15.20 | A |
| ATOM | 733 | CB | ALA | 191 | -10.730 | 0.928 | -4.968 | 1.00 | 14.79 | A |
| ATOM | 734 | C | ALA | 191 | -11.439 | 3.230 | -4.206 | 1.00 | 17.11 | A |
| ATOM | 735 | O | ALA | 191 | -10.467 | 3.961 | -4.052 | 1.00 | 14.04 | A |
| ATOM | 736 | N | SER | 192 | -12.511 | 3.245 | -3.433 | 1.00 | 14.72 | A |
| ATOM | 737 | H | SER | 192 | -13.277 | 2.694 | -3.804 | 1.00 | 15.00 | A |
| ATOM | 738 | CA | SER | 192 | -12.725 | 4.289 | -2.423 | 1.00 | 16.69 | A |
| ATOM | 739 | CB | SER | 192 | -13.931 | 5.144 | -2.803 | 1.00 | 14.83 | A |
| ATOM | 740 | OG | SER | 192 | -13.556 | 5.828 | -3.994 | 1.00 | 21.23 | A |
| ATOM | 741 | HG | SER | 192 | -14.367 | 5.966 | -4.520 | 1.00 | 15.00 | A |
| ATOM | 742 | C | SER | 192 | -12.980 | 3.682 | -1.069 | 1.00 | 17.77 | A |
| ATOM | 743 | O | SER | 192 | -13.753 | 2.738 | -0.947 | 1.00 | 20.76 | A |
| ATOM | 744 | N | LEU | 193 | -12.285 | 4.209 | -0.038 | 1.00 | 15.56 | A |
| ATOM | 745 | H | LEU | 193 | -11.681 | 4.959 | -0.280 | 1.00 | 15.00 | A |
| ATOM | 746 | CA | LEU | 193 | -12.510 | 3.761 | 1.366 | 1.00 | 13.27 | A |
| ATOM | 747 | CB | LEU | 193 | -11.195 | 3.825 | 2.217 | 1.00 | 12.74 | A |
| ATOM | 748 | CG | LEU | 193 | -11.051 | 3.141 | 3.604 | 1.00 | 14.37 | A |
| ATOM | 749 | CD1 | LEU | 193 | -12.272 | 2.354 | 4.116 | 1.00 | 14.67 | A |
| ATOM | 750 | CD2 | LEU | 193 | -10.274 | 3.986 | 4.622 | 1.00 | 12.64 | A |
| ATOM | 751 | C | LEU | 193 | -13.497 | 4.748 | 1.911 | 1.00 | 11.22 | A |
| ATOM | 752 | O | LEU | 193 | -13.188 | 5.912 | 1.903 | 1.00 | 12.22 | A |
| ATOM | 753 | N | CYS | 194 | -14.652 | 4.326 | 2.310 | 1.00 | 13.66 | A |
| ATOM | 754 | H | CYS | 194 | -14.828 | 3.347 | 2.276 | 1.00 | 15.00 | A |
| ATOM | 755 | CA | CYS | 194 | -15.595 | 5.360 | 2.713 | 1.00 | 14.84 | A |
| ATOM | 756 | CB | CYS | 194 | -16.915 | 5.409 | 1.918 | 1.00 | 17.58 | A |
| ATOM | 757 | SG | CYS | 194 | -16.623 | 5.417 | 0.165 | 1.00 | 16.33 | A |
| ATOM | 758 | C | CYS | 194 | -16.046 | 5.163 | 4.137 | 1.00 | 12.81 | A |
| ATOM | 759 | O | CYS | 194 | -15.983 | 4.072 | 4.655 | 1.00 | 10.34 | A |
| ATOM | 760 | N | LEU | 195 | -16.557 | 6.254 | 4.697 | 1.00 | 14.32 | A |
| ATOM | 761 | H | LEU | 195 | -16.541 | 7.088 | 4.154 | 1.00 | 15.00 | A |
| ATOM | 762 | CA | LEU | 195 | -17.039 | 6.291 | 6.076 | 1.00 | 14.89 | A |
| ATOM | 763 | CB | LEU | 195 | -16.195 | 7.372 | 6.789 | 1.00 | 15.56 | A |
| ATOM | 764 | CG | LEU | 195 | -16.571 | 7.680 | 8.242 | 1.00 | 15.56 | A |
| ATOM | 765 | CD1 | LEU | 195 | -15.932 | 8.967 | 8.762 | 1.00 | 13.72 | A |
| ATOM | 766 | CD2 | LEU | 195 | -16.463 | 6.448 | 9.154 | 1.00 | 17.25 | A |
| ATOM | 767 | C | LEU | 195 | -18.546 | 6.544 | 6.209 | 1.00 | 13.54 | A |
| ATOM | 768 | O | LEU | 195 | -19.038 | 7.521 | 5.705 | 1.00 | 14.56 | A |
| ATOM | 769 | N | LYS | 196 | -19.238 | 5.667 | 6.905 | 1.00 | 16.36 | A |
| ATOM | 770 | H | LYS | 196 | -18.719 | 4.875 | 7.197 | 1.00 | 15.00 | A |
| ATOM | 771 | CA | LYS | 196 | -20.577 | 5.972 | 7.405 | 1.00 | 21.01 | A |
| ATOM | 772 | CB | LYS | 196 | -21.475 | 4.726 | 7.146 | 1.00 | 22.66 | A |
| ATOM | 773 | CG | LYS | 196 | -22.953 | 4.839 | 7.590 | 1.00 | 31.25 | A |
| ATOM | 774 | CD | LYS | 196 | -23.364 | 4.915 | 9.104 | 1.00 | 40.25 | A |
| ATOM | 775 | CE | LYS | 196 | -23.189 | 3.694 | 10.060 | 1.00 | 43.56 | A |
| ATOM | 776 | NZ | LYS | 196 | -23.004 | 4.158 | 11.453 | 1.00 | 44.46 | A |
| ATOM | 777 | HZ1 | LYS | 196 | -22.182 | 4.799 | 11.467 | 1.00 | 15.00 | A |
| ATOM | 778 | HZ2 | LYS | 196 | -23.847 | 4.665 | 11.778 | 1.00 | 15.00 | A |
| ATOM | 779 | HZ3 | LYS | 196 | -22.807 | 3.334 | 12.066 | 1.00 | 15.00 | A |

FIG. 17N

```
ATOM    780  C    LYS   196     -20.478    6.290    8.899  1.00 19.25      A
ATOM    781  O    LYS   196     -20.194    5.434    9.714  1.00 18.35      A
ATOM    782  N    SER   197     -20.664    7.534    9.272  1.00 20.63      A
ATOM    783  H    SER   197     -20.891    8.247    8.615  1.00 15.00      A
ATOM    784  CA   SER   197     -20.752    7.701   10.729  1.00 24.87      A
ATOM    785  CB   SER   197     -19.898    8.878   11.207  1.00 25.62      A
ATOM    786  OG   SER   197     -19.563    8.687   12.588  1.00 32.22      A
ATOM    787  HG   SER   197     -18.795    8.110   12.611  1.00 15.00      A
ATOM    788  C    SER   197     -22.216    7.810   11.218  1.00 26.33      A
ATOM    789  O    SER   197     -23.078    8.303   10.497  1.00 26.57      A
ATOM    790  N    PRO   198     -22.534    7.274   12.407  1.00 26.77      A
ATOM    791  CD   PRO   198     -21.649    6.526   13.301  1.00 32.92      A
ATOM    792  CA   PRO   198     -23.919    7.381   12.913  1.00 28.73      A
ATOM    793  CB   PRO   198     -23.784    6.789   14.318  1.00 32.89      A
ATOM    794  CG   PRO   198     -22.289    6.726   14.659  1.00 33.55      A
ATOM    795  C    PRO   198     -24.591    8.789   12.847  1.00 26.60      A
ATOM    796  O    PRO   198     -24.035    9.817   13.242  1.00 20.20      A
ATOM    797  N    GLY   199     -25.729    8.773   12.119  1.00 25.75      A
ATOM    798  H    GLY   199     -26.170    7.857   12.057  1.00 15.00      A
ATOM    799  CA   GLY   199     -26.486   10.003   11.790  1.00 26.91      A
ATOM    800  C    GLY   199     -25.821   10.971   10.816  1.00 28.98      A
ATOM    801  O    GLY   199     -26.084   12.151   10.797  1.00 31.05      A
ATOM    802  N    ARG   200     -24.898   10.464   10.001  1.00 30.15      A
ATOM    803  H    ARG   200     -24.629    9.519   10.165  1.00 15.00      A
ATOM    804  CA   ARG   200     -24.140   11.384    9.166  1.00 28.98      A
ATOM    805  CB   ARG   200     -22.749   11.590    9.783  1.00 33.16      A
ATOM    806  CG   ARG   200     -22.739   12.290   11.162  1.00 38.34      A
ATOM    807  CD   ARG   200     -21.327   12.530   11.705  1.00 42.14      A
ATOM    808  NE   ARG   200     -21.292   12.875   13.131  1.00 43.64      A
ATOM    809  HE   ARG   200     -21.327   13.831   13.424  1.00 15.00      A
ATOM    810  CZ   ARG   200     -21.138   11.896   14.051  1.00 46.40      A
ATOM    811  NH1  ARG   200     -21.219   10.603   13.733  1.00 46.31      A
ATOM    812  HH11 ARG   200     -21.104    9.910   14.445  1.00 15.00      A
ATOM    813  HH12 ARG   200     -21.394   10.320   12.789  1.00 15.00      A
ATOM    814  NH2  ARG   200     -20.901   12.226   15.311  1.00 46.65      A
ATOM    815  HH21 ARG   200     -20.847   13.193   15.566  1.00 15.00      A
ATOM    816  HH22 ARG   200     -20.785   11.510   16.002  1.00 15.00      A
ATOM    817  C    ARG   200     -24.084   10.967    7.710  1.00 27.77      A
ATOM    818  O    ARG   200     -24.264    9.791    7.449  1.00 28.21      A
ATOM    819  N    PHE   201     -23.853   11.926    6.792  1.00 30.83      A
ATOM    820  H    PHE   201     -23.513   12.821    7.126  1.00 15.00      A
ATOM    821  CA   PHE   201     -24.016   11.708    5.339  1.00 34.17      A
ATOM    822  CB   PHE   201     -23.851   12.996    4.572  1.00 31.58      A
ATOM    823  CG   PHE   201     -25.154   13.730    4.614  1.00 34.85      A
ATOM    824  CD1  PHE   201     -25.174   15.062    5.081  1.00 37.56      A
ATOM    825  CD2  PHE   201     -26.335   13.081    4.190  1.00 37.89      A
ATOM    826  CE1  PHE   201     -26.397   15.749    5.182  1.00 36.91      A
ATOM    827  CE2  PHE   201     -27.566   13.762    4.280  1.00 38.98      A
ATOM    828  CZ   PHE   201     -27.572   15.065    4.815  1.00 37.61      A
ATOM    829  C    PHE   201     -23.277   10.605    4.545  1.00 39.40      A
ATOM    830  O    PHE   201     -23.853   10.034    3.604  1.00 45.71      A
ATOM    831  N    GLU   202     -22.031   10.316    5.034  1.00 35.75      A
ATOM    832  H    GLU   202     -21.878   10.753    5.925  1.00 15.00      A
ATOM    833  CA   GLU   202     -20.964    9.564    4.318  1.00 34.52      A
ATOM    834  CB   GLU   202     -21.295    8.540    3.234  1.00 33.66      A
ATOM    835  CG   GLU   202     -21.924    7.245    3.713  1.00 40.61      A
ATOM    836  CD   GLU   202     -22.647    6.505    2.561  1.00 46.12      A
ATOM    837  OE1  GLU   202     -23.461    5.613    2.886  1.00 46.89      A
ATOM    838  OE2  GLU   202     -22.417    6.814    1.370  1.00 45.63      A
ATOM    839  C    GLU   202     -19.924   10.450    3.717  1.00 29.99      A
```

FIG. 170

| | | | | | | | | | |
|---|---|---|---|---|---|---|---|---|---|
| ATOM | 840 | O | GLU | 202 | -20.137 | 11.567 | 3.300 | 1.00 30.76 | A |
| ATOM | 841 | N | ARG | 203 | -18.728 | 9.897 | 3.856 | 1.00 26.88 | A |
| ATOM | 842 | H | ARG | 203 | -18.690 | 8.998 | 4.285 | 1.00 15.00 | A |
| ATOM | 843 | CA | ARG | 203 | -17.539 | 10.603 | 3.358 | 1.00 21.88 | A |
| ATOM | 844 | CB | ARG | 203 | -16.819 | 11.410 | 4.457 | 1.00 27.07 | A |
| ATOM | 845 | CG | ARG | 203 | -17.681 | 12.187 | 5.467 | 1.00 37.32 | A |
| ATOM | 846 | CD | ARG | 203 | -16.894 | 13.213 | 6.339 | 1.00 48.09 | A |
| ATOM | 847 | NE | ARG | 203 | -15.911 | 12.667 | 7.308 | 1.00 56.90 | A |
| ATOM | 848 | HE | ARG | 203 | -16.240 | 12.433 | 8.223 | 1.00 15.00 | A |
| ATOM | 849 | CZ | ARG | 203 | -14.572 | 12.475 | 7.001 | 1.00 66.77 | A |
| ATOM | 850 | NH1 | ARG | 203 | -13.702 | 12.002 | 7.911 | 1.00 68.44 | A |
| ATOM | 851 | HH11 | ARG | 203 | -12.745 | 11.829 | 7.666 | 1.00 15.00 | A |
| ATOM | 852 | HH12 | ARG | 203 | -14.016 | 11.822 | 8.845 | 1.00 15.00 | A |
| ATOM | 853 | NH2 | ARG | 203 | -14.084 | 12.716 | 5.766 | 1.00 67.68 | A |
| ATOM | 854 | HH21 | ARG | 203 | -14.670 | 13.108 | 5.060 | 1.00 15.00 | A |
| ATOM | 855 | HH22 | ARG | 203 | -13.143 | 12.499 | 5.544 | 1.00 15.00 | A |
| ATOM | 856 | C | ARG | 203 | -16.517 | 9.633 | 2.678 | 1.00 17.71 | A |
| ATOM | 857 | O | ARG | 203 | -16.375 | 8.418 | 2.931 | 1.00 7.69 | A |
| ATOM | 858 | N | ILE | 204 | -15.789 | 10.253 | 1.791 | 1.00 14.42 | A |
| ATOM | 859 | H | ILE | 204 | -15.915 | 11.228 | 1.561 | 1.00 15.00 | A |
| ATOM | 860 | CA | ILE | 204 | -14.662 | 9.482 | 1.353 | 1.00 18.32 | A |
| ATOM | 861 | CB | ILE | 204 | -14.520 | 9.392 | -0.231 | 1.00 24.52 | A |
| ATOM | 862 | CG2 | ILE | 204 | -15.820 | 9.529 | -1.069 | 1.00 21.85 | A |
| ATOM | 863 | CG1 | ILE | 204 | -13.439 | 10.195 | -0.949 | 1.00 26.35 | A |
| ATOM | 864 | CD1 | ILE | 204 | -13.992 | 11.231 | -1.961 | 1.00 36.33 | A |
| ATOM | 865 | C | ILE | 204 | -13.387 | 9.819 | 2.153 | 1.00 16.58 | A |
| ATOM | 866 | O | ILE | 204 | -13.070 | 10.956 | 2.457 | 1.00 18.63 | A |
| ATOM | 867 | N | LEU | 205 | -12.718 | 8.725 | 2.571 | 1.00 13.32 | A |
| ATOM | 868 | H | LEU | 205 | -13.142 | 7.853 | 2.321 | 1.00 15.00 | A |
| ATOM | 869 | CA | LEU | 205 | -11.467 | 8.829 | 3.322 | 1.00 10.01 | A |
| ATOM | 870 | CB | LEU | 205 | -11.440 | 7.688 | 4.382 | 1.00 6.66 | A |
| ATOM | 871 | CG | LEU | 205 | -12.571 | 7.727 | 5.441 | 1.00 7.99 | A |
| ATOM | 872 | CD1 | LEU | 205 | -12.722 | 9.088 | 6.089 | 1.00 8.78 | A |
| ATOM | 873 | CD2 | LEU | 205 | -12.419 | 6.720 | 6.582 | 1.00 8.08 | A |
| ATOM | 874 | C | LEU | 205 | -10.268 | 8.811 | 2.377 | 1.00 9.75 | A |
| ATOM | 875 | O | LEU | 205 | -9.416 | 9.655 | 2.320 | 1.00 10.25 | A |
| ATOM | 876 | N | LEU | 206 | -10.252 | 7.769 | 1.562 | 1.00 10.28 | A |
| ATOM | 877 | H | LEU | 206 | -10.991 | 7.119 | 1.684 | 1.00 15.00 | A |
| ATOM | 878 | CA | LEU | 206 | -9.166 | 7.555 | 0.610 | 1.00 10.02 | A |
| ATOM | 879 | CB | LEU | 206 | -8.249 | 6.384 | 0.990 | 1.00 11.94 | A |
| ATOM | 880 | CG | LEU | 206 | -7.001 | 6.527 | 1.859 | 1.00 14.40 | A |
| ATOM | 881 | CD1 | LEU | 206 | -7.094 | 5.595 | 3.074 | 1.00 14.49 | A |
| ATOM | 882 | CD2 | LEU | 206 | -6.531 | 7.958 | 2.151 | 1.00 8.78 | A |
| ATOM | 883 | C | LEU | 206 | -9.756 | 7.071 | -0.697 | 1.00 11.91 | A |
| ATOM | 884 | O | LEU | 206 | -10.792 | 6.406 | -0.778 | 1.00 10.67 | A |
| ATOM | 885 | N | ARG | 207 | -9.005 | 7.428 | -1.720 | 1.00 8.06 | A |
| ATOM | 886 | H | ARG | 207 | -8.196 | 7.992 | -1.553 | 1.00 15.00 | A |
| ATOM | 887 | CA | ARG | 207 | -9.309 | 6.823 | -2.992 | 1.00 10.45 | A |
| ATOM | 888 | CB | ARG | 207 | -9.974 | 7.790 | -3.904 | 1.00 8.71 | A |
| ATOM | 889 | CG | ARG | 207 | -11.258 | 8.270 | -3.357 | 1.00 15.68 | A |
| ATOM | 890 | CD | ARG | 207 | -11.652 | 9.459 | -4.163 | 1.00 22.25 | A |
| ATOM | 891 | NE | ARG | 207 | -12.670 | 9.192 | -5.171 | 1.00 29.59 | A |
| ATOM | 892 | HE | ARG | 207 | -13.115 | 8.300 | -5.249 | 1.00 15.00 | A |
| ATOM | 893 | CZ | ARG | 207 | -13.063 | 10.272 | -5.919 | 1.00 40.09 | A |
| ATOM | 894 | NH1 | ARG | 207 | -12.482 | 11.498 | -5.813 | 1.00 36.32 | A |
| ATOM | 895 | HH11 | ARG | 207 | -12.813 | 12.246 | -6.391 | 1.00 15.00 | A |
| ATOM | 896 | HH12 | ARG | 207 | -11.737 | 11.651 | -5.165 | 1.00 15.00 | A |
| ATOM | 897 | NH2 | ARG | 207 | -14.067 | 10.111 | -6.773 | 1.00 40.86 | A |
| ATOM | 898 | HH21 | ARG | 207 | -14.392 | 10.877 | -7.329 | 1.00 15.00 | A |
| ATOM | 899 | HH22 | ARG | 207 | -14.498 | 9.207 | -6.853 | 1.00 15.00 | A |

FIG. 17P

| | | | | | | | | | | |
|---|---|---|---|---|---|---|---|---|---|---|
| ATOM | 900 | C | ARG | 207 | -8.044 | 6.456 | -3.741 | 1.00 | 12.59 | A |
| ATOM | 901 | O | ARG | 207 | -7.053 | 7.150 | -3.787 | 1.00 | 15.58 | A |
| ATOM | 902 | N | ALA | 208 | -8.096 | 5.358 | -4.465 | 1.00 | 17.06 | A |
| ATOM | 903 | H | ALA | 208 | -8.879 | 4.758 | -4.355 | 1.00 | 15.00 | A |
| ATOM | 904 | CA | ALA | 208 | -7.025 | 5.128 | -5.465 | 1.00 | 17.00 | A |
| ATOM | 905 | CB | ALA | 208 | -6.052 | 4.020 | -5.072 | 1.00 | 14.69 | A |
| ATOM | 906 | C | ALA | 208 | -7.544 | 4.830 | -6.854 | 1.00 | 20.46 | A |
| ATOM | 907 | O | ALA | 208 | -8.438 | 4.020 | -7.057 | 1.00 | 21.89 | A |
| ATOM | 908 | N | ALA | 209 | -6.986 | 5.586 | -7.808 | 1.00 | 26.22 | A |
| ATOM | 909 | H | ALA | 209 | -6.280 | 6.235 | -7.533 | 1.00 | 15.00 | A |
| ATOM | 910 | CA | ALA | 209 | -7.253 | 5.208 | -9.196 | 1.00 | 28.06 | A |
| ATOM | 911 | CB | ALA | 209 | -7.702 | 6.380 | -10.069 | 1.00 | 27.10 | A |
| ATOM | 912 | C | ALA | 209 | -6.075 | 4.461 | -9.832 | 1.00 | 32.54 | A |
| ATOM | 913 | O | ALA | 209 | -4.895 | 4.726 | -9.593 | 1.00 | 33.00 | A |
| ATOM | 914 | N | ASN | 210 | -6.502 | 3.491 | -10.634 | 1.00 | 32.11 | A |
| ATOM | 915 | H | ASN | 210 | -7.466 | 3.249 | -10.531 | 1.00 | 15.00 | A |
| ATOM | 916 | CA | ASN | 210 | -5.674 | 2.893 | -11.662 | 1.00 | 36.00 | A |
| ATOM | 917 | CB | ASN | 210 | -5.366 | 1.446 | -11.355 | 1.00 | 39.53 | A |
| ATOM | 918 | CG | ASN | 210 | -4.463 | 1.366 | -10.154 | 1.00 | 42.59 | A |
| ATOM | 919 | OD1 | ASN | 210 | -4.285 | 2.273 | -9.342 | 1.00 | 39.26 | A |
| ATOM | 920 | ND2 | ASN | 210 | -3.951 | 0.165 | -10.055 | 1.00 | 41.77 | A |
| ATOM | 921 | HD21 | ASN | 210 | -3.990 | -0.479 | -10.817 | 1.00 | 15.00 | A |
| ATOM | 922 | HD22 | ASN | 210 | -3.364 | -0.081 | -9.279 | 1.00 | 15.00 | A |
| ATOM | 923 | C | ASN | 210 | -6.299 | 2.931 | -13.043 | 1.00 | 36.95 | A |
| ATOM | 924 | O | ASN | 210 | -7.492 | 2.752 | -13.259 | 1.00 | 36.93 | A |
| ATOM | 925 | N | THR | 211 | -5.447 | 3.168 | -14.013 | 1.00 | 37.83 | A |
| ATOM | 926 | H | THR | 211 | -4.484 | 3.377 | -13.821 | 1.00 | 15.00 | A |
| ATOM | 927 | CA | THR | 211 | -6.119 | 3.224 | -15.314 | 1.00 | 41.27 | A |
| ATOM | 928 | CB | THR | 211 | -5.325 | 4.158 | -16.268 | 1.00 | 44.53 | A |
| ATOM | 929 | OG1 | THR | 211 | -6.076 | 4.506 | -17.438 | 1.00 | 49.34 | A |
| ATOM | 930 | HG1 | THR | 211 | -6.032 | 5.493 | -17.508 | 1.00 | 15.00 | A |
| ATOM | 931 | CG2 | THR | 211 | -3.926 | 3.604 | -16.581 | 1.00 | 46.08 | A |
| ATOM | 932 | C | THR | 211 | -6.434 | 1.833 | -15.878 | 1.00 | 39.17 | A |
| ATOM | 933 | O | THR | 211 | -5.822 | 0.863 | -15.475 | 1.00 | 36.48 | A |
| ATOM | 934 | N | HIS | 212 | -7.416 | 1.718 | -16.789 | 1.00 | 37.14 | A |
| ATOM | 935 | H | HIS | 212 | -8.106 | 2.438 | -16.878 | 1.00 | 15.00 | A |
| ATOM | 936 | CA | HIS | 212 | -7.294 | 0.454 | -17.529 | 1.00 | 33.23 | A |
| ATOM | 937 | CB | HIS | 212 | -8.680 | -0.012 | -18.082 | 1.00 | 27.73 | A |
| ATOM | 938 | CG | HIS | 212 | -9.856 | 0.060 | -17.111 | 1.00 | 24.58 | A |
| ATOM | 939 | ND1 | HIS | 212 | -10.862 | 0.967 | -17.161 | 1.00 | 24.59 | A |
| ATOM | 940 | HD1 | HIS | 212 | -11.000 | 1.702 | -17.794 | 1.00 | 15.00 | A |
| ATOM | 941 | CD2 | HIS | 212 | -10.049 | -0.723 | -15.985 | 1.00 | 20.65 | A |
| ATOM | 942 | NE2 | HIS | 212 | -11.154 | -0.265 | -15.383 | 1.00 | 24.01 | A |
| ATOM | 943 | CE1 | HIS | 212 | -11.665 | 0.780 | -16.092 | 1.00 | 17.59 | A |
| ATOM | 944 | C | HIS | 212 | -6.257 | 0.633 | -18.683 | 1.00 | 38.31 | A |
| ATOM | 945 | O | HIS | 212 | -5.363 | -0.132 | -18.923 | 1.00 | 33.92 | A |
| ATOM | 946 | N | SER | 213 | -6.444 | 1.737 | -19.443 | 1.00 | 46.63 | A |
| ATOM | 947 | H | SER | 213 | -7.156 | 2.323 | -19.055 | 1.00 | 15.00 | A |
| ATOM | 948 | CA | SER | 213 | -5.705 | 2.177 | -20.675 | 1.00 | 53.91 | A |
| ATOM | 949 | CB | SER | 213 | -4.272 | 2.704 | -20.400 | 1.00 | 52.61 | A |
| ATOM | 950 | OG | SER | 213 | -3.266 | 1.697 | -20.547 | 1.00 | 53.97 | A |
| ATOM | 951 | HG | SER | 213 | -3.363 | 1.064 | -19.823 | 1.00 | 15.00 | A |
| ATOM | 952 | C | SER | 213 | -5.844 | 1.508 | -22.097 | 1.00 | 60.03 | A |
| ATOM | 953 | O | SER | 213 | -5.005 | 0.811 | -22.682 | 1.00 | 61.19 | A |
| ATOM | 954 | N | SER | 214 | -7.043 | 1.803 | -22.686 | 1.00 | 64.96 | A |
| ATOM | 955 | H | SER | 214 | -7.705 | 2.322 | -22.146 | 1.00 | 15.00 | A |
| ATOM | 956 | CA | SER | 214 | -7.463 | 1.456 | -24.094 | 1.00 | 69.62 | A |
| ATOM | 957 | CB | SER | 214 | 8.727 | 2.218 | -24.495 | 1.00 | 67.82 | A |
| ATOM | 958 | OG | SER | 214 | -9.563 | 2.257 | -23.336 | 1.00 | 67.64 | A |
| ATOM | 959 | HG | SER | 214 | -10.468 | 2.398 | -23.623 | 1.00 | 15.00 | A |

FIG.17Q

| ATOM | 960 | C | SER | 214 | -6.518 | 1.587 | -25.300 | 1.00 | 72.08 | A |
|---|---|---|---|---|---|---|---|---|---|---|
| ATOM | 961 | O | SER | 214 | -6.102 | 2.683 | -25.686 | 1.00 | 73.45 | A |
| ATOM | 962 | N | ALA | 215 | -6.175 | 0.409 | -25.899 | 1.00 | 73.38 | A |
| ATOM | 963 | H | ALA | 215 | -5.456 | 0.596 | -26.565 | 1.00 | 15.00 | A |
| ATOM | 964 | CA | ALA | 215 | -6.858 | -0.915 | -25.753 | 1.00 | 72.62 | A |
| ATOM | 965 | CB | ALA | 215 | -7.199 | -1.505 | -27.138 | 1.00 | 73.08 | A |
| ATOM | 966 | C | ALA | 215 | -6.331 | -2.148 | -24.983 | 1.00 | 72.11 | A |
| ATOM | 967 | O | ALA | 215 | -7.020 | -3.161 | -25.069 | 1.00 | 72.74 | A |
| ATOM | 968 | N | LYS | 216 | -5.153 | -2.076 | -24.282 | 1.00 | 70.17 | A |
| ATOM | 969 | H | LYS | 216 | -4.747 | -1.165 | -24.199 | 1.00 | 15.00 | A |
| ATOM | 970 | CA | LYS | 216 | -4.482 | -3.256 | -23.626 | 1.00 | 67.38 | A |
| ATOM | 971 | CB | LYS | 216 | -3.458 | -2.691 | -22.648 | 1.00 | 65.30 | A |
| ATOM | 972 | CG | LYS | 216 | -2.217 | -2.107 | -23.321 | 1.00 | 66.86 | A |
| ATOM | 973 | CD | LYS | 216 | -1.419 | -3.149 | -24.134 | 1.00 | 68.81 | A |
| ATOM | 974 | CE | LYS | 216 | -0.082 | -2.674 | -24.740 | 1.00 | 67.51 | A |
| ATOM | 975 | NZ | LYS | 216 | 0.483 | -3.722 | -25.598 | 1.00 | 67.80 | A |
| ATOM | 976 | HZ1 | LYS | 216 | 0.620 | -4.590 | -25.041 | 1.00 | 15.00 | A |
| ATOM | 977 | HZ2 | LYS | 216 | -0.168 | -3.914 | -26.385 | 1.00 | 15.00 | A |
| ATOM | 978 | HZ3 | LYS | 216 | 1.401 | -3.406 | -25.973 | 1.00 | 15.00 | A |
| ATOM | 979 | C | LYS | 216 | -5.321 | -4.441 | -22.993 | 1.00 | 66.99 | A |
| ATOM | 980 | O | LYS | 216 | -6.462 | -4.266 | -22.575 | 1.00 | 69.90 | A |
| ATOM | 981 | N | PRO | 217 | -4.835 | -5.724 | -22.952 | 1.00 | 65.06 | A |
| ATOM | 982 | CD | PRO | 217 | -3.525 | -6.262 | -23.308 | 1.00 | 67.91 | A |
| ATOM | 983 | CA | PRO | 217 | -5.792 | -6.827 | -22.626 | 1.00 | 62.80 | A |
| ATOM | 984 | CB | PRO | 217 | -5.285 | -8.004 | -23.464 | 1.00 | 64.33 | A |
| ATOM | 985 | CG | PRO | 217 | -3.755 | -7.799 | -23.338 | 1.00 | 69.63 | A |
| ATOM | 986 | C | PRO | 217 | -5.837 | -7.237 | -21.150 | 1.00 | 59.77 | A |
| ATOM | 987 | O | PRO | 217 | -4.747 | -7.318 | -20.589 | 1.00 | 58.81 | A |
| ATOM | 988 | N | CYS | 218 | -7.115 | -7.516 | -20.627 | 1.00 | 55.45 | A |
| ATOM | 989 | H | CYS | 218 | -7.874 | -7.287 | -21.233 | 1.00 | 15.00 | A |
| ATOM | 990 | CA | CYS | 218 | -7.433 | -7.929 | -19.210 | 1.00 | 46.55 | A |
| ATOM | 991 | CB | CYS | 218 | -8.105 | -9.289 | -19.079 | 1.00 | 44.69 | A |
| ATOM | 992 | SG | CYS | 218 | -8.855 | -9.822 | -17.460 | 1.00 | 43.11 | A |
| ATOM | 993 | C | CYS | 218 | -6.265 | -7.994 | -18.263 | 1.00 | 43.24 | A |
| ATOM | 994 | O | CYS | 218 | -5.720 | -9.026 | -17.959 | 1.00 | 44.68 | A |
| ATOM | 995 | N | GLY | 219 | -5.853 | -6.820 | -17.876 | 1.00 | 40.28 | A |
| ATOM | 996 | H | GLY | 219 | -6.328 | -5.961 | -18.059 | 1.00 | 15.00 | A |
| ATOM | 997 | CA | GLY | 219 | -4.659 | -6.828 | -17.070 | 1.00 | 36.27 | A |
| ATOM | 998 | C | GLY | 219 | -5.017 | -7.080 | -15.643 | 1.00 | 33.86 | A |
| ATOM | 999 | O | GLY | 219 | -5.906 | -6.452 | -15.097 | 1.00 | 34.90 | A |
| ATOM | 1000 | N | GLN | 220 | -4.313 | -7.996 | -15.023 | 1.00 | 33.15 | A |
| ATOM | 1001 | H | GLN | 220 | -3.835 | -8.684 | -15.580 | 1.00 | 15.00 | A |
| ATOM | 1002 | CA | GLN | 220 | -4.448 | -7.929 | -13.578 | 1.00 | 29.92 | A |
| ATOM | 1003 | CB | GLN | 220 | -4.298 | -9.282 | -12.936 | 1.00 | 27.81 | A |
| ATOM | 1004 | CG | GLN | 220 | -5.380 | -9.340 | -11.883 | 1.00 | 30.94 | A |
| ATOM | 1005 | CD | GLN | 220 | -5.285 | -10.631 | -11.132 | 1.00 | 36.37 | A |
| ATOM | 1006 | OE1 | GLN | 220 | -4.216 | -10.969 | -10.661 | 1.00 | 38.47 | A |
| ATOM | 1007 | NE2 | GLN | 220 | -6.425 | -11.296 | -10.977 | 1.00 | 37.61 | A |
| ATOM | 1008 | HE21 | GLN | 220 | -6.295 | -12.235 | -10.667 | 1.00 | 15.00 | A |
| ATOM | 1009 | HE22 | GLN | 220 | -7.373 | -11.036 | -11.200 | 1.00 | 15.00 | A |
| ATOM | 1010 | C | GLN | 220 | -3.666 | -6.845 | -12.859 | 1.00 | 27.48 | A |
| ATOM | 1011 | O | GLN | 220 | -2.461 | -6.694 | -12.999 | 1.00 | 27.61 | A |
| ATOM | 1012 | N | GLN | 221 | -4.438 | -6.040 | -12.110 | 1.00 | 25.10 | A |
| ATOM | 1013 | H | GLN | 221 | -5.433 | -6.174 | -12.143 | 1.00 | 15.00 | A |
| ATOM | 1014 | CA | GLN | 221 | -3.803 | -4.929 | -11.387 | 1.00 | 22.41 | A |
| ATOM | 1015 | CB | GLN | 221 | -4.077 | -3.528 | -11.949 | 1.00 | 22.12 | A |
| ATOM | 1016 | CG | GLN | 221 | -3.284 | -3.029 | -13.163 | 1.00 | 32.16 | A |
| ATOM | 1017 | CD | GLN | 221 | -3.795 | -1.637 | -13.405 | 1.00 | 34.69 | A |
| ATOM | 1018 | OE1 | GLN | 221 | -3.746 | -0.763 | -12.558 | 1.00 | 42.12 | A |
| ATOM | 1019 | NE2 | GLN | 221 | -4.648 | -1.507 | -14.398 | 1.00 | 34.93 | A |

FIG. 17R

| | | | | | | | | | |
|---|---|---|---|---|---|---|---|---|---|
| ATOM | 1020 | HE21 | GLN | 221 | -4.981 | -2.187 | -15.042 | 1.00 15.00 | A |
| ATOM | 1021 | HE22 | GLN | 221 | -4.844 | -0.551 | -14.575 | 1.00 15.00 | A |
| ATOM | 1022 | C | GLN | 221 | -4.227 | -4.913 | -9.948 | 1.00 19.54 | A |
| ATOM | 1023 | O | GLN | 221 | -5.300 | -5.381 | -9.611 | 1.00 19.46 | A |
| ATOM | 1024 | N | SER | 222 | -3.374 | -4.330 | -9.123 | 1.00 19.12 | A |
| ATOM | 1025 | H | SER | 222 | -2.442 | -4.098 | -9.441 | 1.00 15.00 | A |
| ATOM | 1026 | CA | SER | 222 | -3.851 | -4.120 | -7.752 | 1.00 19.45 | A |
| ATOM | 1027 | CB | SER | 222 | -3.104 | -4.947 | -6.691 | 1.00 19.99 | A |
| ATOM | 1028 | OG | SER | 222 | -3.096 | -6.339 | -7.053 | 1.00 24.64 | A |
| ATOM | 1029 | HG | SER | 222 | -2.651 | -6.336 | -7.904 | 1.00 15.00 | A |
| ATOM | 1030 | C | SER | 222 | -3.731 | -2.688 | -7.330 | 1.00 24.09 | A |
| ATOM | 1031 | O | SER | 222 | -2.992 | -1.929 | -7.944 | 1.00 29.41 | A |
| ATOM | 1032 | N | ILE | 223 | -4.534 | -2.386 | -6.283 | 1.00 22.81 | A |
| ATOM | 1033 | H | ILE | 223 | -5.172 | -3.127 | -6.074 | 1.00 15.00 | A |
| ATOM | 1034 | CA | ILE | 223 | -4.567 | -1.122 | -5.530 | 1.00 21.06 | A |
| ATOM | 1035 | CB | ILE | 223 | -5.970 | -0.490 | -5.852 | 1.00 19.87 | A |
| ATOM | 1036 | CG2 | ILE | 223 | -6.564 | 0.315 | -4.673 | 1.00 16.59 | A |
| ATOM | 1037 | CG1 | ILE | 223 | -5.911 | 0.278 | -7.188 | 1.00 15.22 | A |
| ATOM | 1038 | CD1 | ILE | 223 | -7.229 | 0.868 | -7.709 | 1.00 20.54 | A |
| ATOM | 1039 | C | ILE | 223 | -4.367 | -1.446 | -4.007 | 1.00 21.62 | A |
| ATOM | 1040 | O | ILE | 223 | -5.098 | -2.269 | -3.444 | 1.00 19.58 | A |
| ATOM | 1041 | N | HIS | 224 | -3.429 | -0.767 | -3.340 | 1.00 19.73 | A |
| ATOM | 1042 | H | HIS | 224 | -2.794 | -0.230 | -3.899 | 1.00 15.00 | A |
| ATOM | 1043 | CA | HIS | 224 | -3.497 | -0.671 | -1.858 | 1.00 16.45 | A |
| ATOM | 1044 | CB | HIS | 224 | -2.164 | -1.183 | -1.227 | 1.00 18.74 | A |
| ATOM | 1045 | CG | HIS | 224 | -2.182 | -1.442 | 0.296 | 1.00 14.92 | A |
| ATOM | 1046 | ND1 | HIS | 224 | -2.479 | -2.628 | 0.682 | 1.00 15.33 | A |
| ATOM | 1047 | HD1 | HIS | 224 | -2.667 | -3.515 | 0.505 | 1.00 15.00 | A |
| ATOM | 1048 | CD2 | HIS | 224 | -1.964 | -0.524 | 1.310 | 1.00 13.79 | A |
| ATOM | 1049 | NE2 | HIS | 224 | -2.137 | -1.127 | 2.517 | 1.00 10.52 | A |
| ATOM | 1050 | CE1 | HIS | 224 | -2.458 | -2.411 | 2.232 | 1.00 11.70 | A |
| ATOM | 1051 | C | HIS | 224 | -3.914 | 0.699 | -1.284 | 1.00 15.18 | A |
| ATOM | 1052 | O | HIS | 224 | -3.338 | 1.732 | -1.520 | 1.00 14.36 | A |
| ATOM | 1053 | N | LEU | 225 | -4.970 | 0.673 | -0.468 | 1.00 16.85 | A |
| ATOM | 1054 | H | LEU | 225 | -5.317 | -0.238 | -0.252 | 1.00 15.00 | A |
| ATOM | 1055 | CA | LEU | 225 | -5.395 | 1.885 | 0.256 | 1.00 15.55 | A |
| ATOM | 1056 | CB | LEU | 225 | -6.927 | 2.082 | 0.208 | 1.00 17.15 | A |
| ATOM | 1057 | CG | LEU | 225 | -7.495 | 2.456 | -1.154 | 1.00 18.03 | A |
| ATOM | 1058 | CD1 | LEU | 225 | -6.792 | 3.659 | -1.774 | 1.00 19.34 | A |
| ATOM | 1059 | CD2 | LEU | 225 | -8.994 | 2.659 | -1.098 | 1.00 13.66 | A |
| ATOM | 1060 | C | LEU | 225 | -5.074 | 1.758 | 1.739 | 1.00 14.77 | A |
| ATOM | 1061 | O | LEU | 225 | -5.347 | 0.726 | 2.345 | 1.00 12.20 | A |
| ATOM | 1062 | N | GLY | 226 | -4.544 | 2.829 | 2.344 | 1.00 18.04 | A |
| ATOM | 1063 | H | GLY | 226 | -4.218 | 3.616 | 1.813 | 1.00 15.00 | A |
| ATOM | 1064 | CA | GLY | 226 | -4.541 | 2.833 | 3.841 | 1.00 18.37 | A |
| ATOM | 1065 | C | GLY | 226 | -4.193 | 4.171 | 4.544 | 1.00 17.08 | A |
| ATOM | 1066 | O | GLY | 226 | -3.389 | 4.906 | 4.055 | 1.00 13.75 | A |
| ATOM | 1067 | N | GLY | 227 | -4.781 | 4.457 | 5.725 | 1.00 16.30 | A |
| ATOM | 1068 | H | GLY | 227 | -5.434 | 3.771 | 6.036 | 1.00 15.00 | A |
| ATOM | 1069 | CA | GLY | 227 | -4.379 | 5.649 | 6.490 | 1.00 8.52 | A |
| ATOM | 1070 | C | GLY | 227 | -4.935 | 5.631 | 7.959 | 1.00 12.75 | A |
| ATOM | 1071 | O | GLY | 227 | -5.651 | 4.748 | 8.466 | 1.00 10.57 | A |
| ATOM | 1072 | N | VAL | 228 | -4.588 | 6.698 | 8.675 | 1.00 9.23 | A |
| ATOM | 1073 | H | VAL | 228 | -4.040 | 7.398 | 8.222 | 1.00 15.00 | A |
| ATOM | 1074 | CA | VAL | 228 | -5.110 | 6.818 | 10.067 | 1.00 11.74 | A |
| ATOM | 1075 | CB | VAL | 228 | -4.085 | 7.320 | 11.144 | 1.00 14.30 | A |
| ATOM | 1076 | CG1 | VAL | 228 | -2.830 | 6.445 | 11.333 | 1.00 10.73 | A |
| ATOM | 1077 | CG2 | VAL | 228 | -4.789 | 7.565 | 12.479 | 1.00 17.07 | A |
| ATOM | 1078 | C | VAL | 228 | -6.238 | 7.803 | 10.098 | 1.00 9.03 | A |
| ATOM | 1079 | O | VAL | 228 | -6.089 | 8.937 | 9.649 | 1.00 12.01 | A |

FIG. 17S

| ATOM | 1080 | N | PHE | 229 | -7.347 | 7.299 | 10.640 | 1.00 | 9.88 | A |
|---|---|---|---|---|---|---|---|---|---|---|
| ATOM | 1081 | H | PHE | 229 | -7.329 | 6.332 | 10.922 | 1.00 | 15.00 | A |
| ATOM | 1082 | CA | PHE | 229 | -8.566 | 8.106 | 10.772 | 1.00 | 11.18 | A |
| ATOM | 1083 | CB | PHE | 229 | -9.578 | 7.687 | 9.686 | 1.00 | 8.61 | A |
| ATOM | 1084 | CG | PHE | 229 | -9.063 | 7.912 | 8.233 | 1.00 | 9.40 | A |
| ATOM | 1085 | CD1 | PHE | 229 | -9.140 | 9.196 | 7.649 | 1.00 | 10.03 | A |
| ATOM | 1086 | CD2 | PHE | 229 | -8.433 | 6.883 | 7.517 | 1.00 | 6.57 | A |
| ATOM | 1087 | CE1 | PHE | 229 | -8.512 | 9.443 | 6.395 | 1.00 | 5.18 | A |
| ATOM | 1088 | CE2 | PHE | 229 | -7.771 | 7.128 | 6.282 | 1.00 | 4.26 | A |
| ATOM | 1089 | CZ | PHE | 229 | -7.813 | 8.424 | 5.731 | 1.00 | 5.71 | A |
| ATOM | 1090 | C | PHE | 229 | -9.202 | 8.014 | 12.197 | 1.00 | 14.39 | A |
| ATOM | 1091 | O | PHE | 229 | -9.116 | 7.000 | 12.870 | 1.00 | 13.92 | A |
| ATOM | 1092 | N | GLU | 230 | -9.863 | 9.064 | 12.672 | 1.00 | 17.93 | A |
| ATOM | 1093 | H | GLU | 230 | -9.912 | 9.892 | 12.113 | 1.00 | 15.00 | A |
| ATOM | 1094 | CA | GLU | 230 | -10.856 | 8.944 | 13.770 | 1.00 | 18.08 | A |
| ATOM | 1095 | CB | GLU | 230 | -11.218 | 10.303 | 14.393 | 1.00 | 16.17 | A |
| ATOM | 1096 | CG | GLU | 230 | -11.068 | 10.090 | 15.889 | 1.00 | 27.69 | A |
| ATOM | 1097 | CD | GLU | 230 | -12.314 | 10.091 | 16.805 | 1.00 | 33.06 | A |
| ATOM | 1098 | OE1 | GLU | 230 | -13.355 | 10.707 | 16.552 | 1.00 | 38.26 | A |
| ATOM | 1099 | OE2 | GLU | 230 | -12.218 | 9.477 | 17.863 | 1.00 | 38.14 | A |
| ATOM | 1100 | C | GLU | 230 | -12.225 | 8.268 | 13.453 | 1.00 | 18.70 | A |
| ATOM | 1101 | O | GLU | 230 | -12.967 | 8.519 | 12.492 | 1.00 | 21.58 | A |
| ATOM | 1102 | N | LEU | 231 | -12.542 | 7.334 | 14.361 | 1.00 | 13.79 | A |
| ATOM | 1103 | H | LEU | 231 | -11.840 | 7.125 | 15.015 | 1.00 | 15.00 | A |
| ATOM | 1104 | CA | LEU | 231 | -13.885 | 6.836 | 14.330 | 1.00 | 13.52 | A |
| ATOM | 1105 | CB | LEU | 231 | -13.954 | 5.378 | 14.002 | 1.00 | 13.90 | A |
| ATOM | 1106 | CG | LEU | 231 | -13.199 | 5.064 | 12.725 | 1.00 | 15.44 | A |
| ATOM | 1107 | CD1 | LEU | 231 | -13.781 | 5.712 | 11.436 | 1.00 | 10.24 | A |
| ATOM | 1108 | CD2 | LEU | 231 | -12.970 | 3.569 | 12.769 | 1.00 | 11.74 | A |
| ATOM | 1109 | C | LEU | 231 | -14.638 | 7.074 | 15.591 | 1.00 | 14.88 | A |
| ATOM | 1110 | O | LEU | 231 | -14.145 | 6.912 | 16.692 | 1.00 | 12.46 | A |
| ATOM | 1111 | N | GLN | 232 | -15.891 | 7.411 | 15.350 | 1.00 | 19.40 | A |
| ATOM | 1112 | H | GLN | 232 | -16.107 | 7.560 | 14.394 | 1.00 | 15.00 | A |
| ATOM | 1113 | CA | GLN | 232 | -16.920 | 7.509 | 16.389 | 1.00 | 21.07 | A |
| ATOM | 1114 | CB | GLN | 232 | -18.132 | 8.234 | 15.804 | 1.00 | 23.55 | A |
| ATOM | 1115 | CG | GLN | 232 | -17.792 | 9.709 | 15.687 | 1.00 | 28.60 | A |
| ATOM | 1116 | CD | GLN | 232 | -17.625 | 10.200 | 17.102 | 1.00 | 33.66 | A |
| ATOM | 1117 | OE1 | GLN | 232 | -18.623 | 10.472 | 17.742 | 1.00 | 38.08 | A |
| ATOM | 1118 | NE2 | GLN | 232 | -16.380 | 10.254 | 17.596 | 1.00 | 33.41 | A |
| ATOM | 1119 | HE21 | GLN | 232 | -15.596 | 10.186 | 16.972 | 1.00 | 15.00 | A |
| ATOM | 1120 | HE22 | GLN | 232 | -16.387 | 10.470 | 18.576 | 1.00 | 15.00 | A |
| ATOM | 1121 | C | GLN | 232 | -17.402 | 6.148 | 16.851 | 1.00 | 21.86 | A |
| ATOM | 1122 | O | GLN | 232 | -17.368 | 5.218 | 16.052 | 1.00 | 21.58 | A |
| ATOM | 1123 | N | PRO | 233 | -17.906 | 6.013 | 18.115 | 1.00 | 22.31 | A |
| ATOM | 1124 | CD | PRO | 233 | -17.962 | 7.033 | 19.168 | 1.00 | 21.41 | A |
| ATOM | 1125 | CA | PRO | 233 | -18.570 | 4.747 | 18.442 | 1.00 | 21.21 | A |
| ATOM | 1126 | CB | PRO | 233 | -19.013 | 4.987 | 19.866 | 1.00 | 23.88 | A |
| ATOM | 1127 | CG | PRO | 233 | -18.661 | 6.404 | 20.339 | 1.00 | 20.95 | A |
| ATOM | 1128 | C | PRO | 233 | -19.667 | 4.417 | 17.434 | 1.00 | 23.66 | A |
| ATOM | 1129 | O | PRO | 233 | -20.275 | 5.319 | 16.875 | 1.00 | 26.89 | A |
| ATOM | 1130 | N | GLY | 234 | -19.731 | 3.140 | 17.059 | 1.00 | 22.77 | A |
| ATOM | 1131 | H | GLY | 234 | -19.082 | 2.466 | 17.417 | 1.00 | 15.00 | A |
| ATOM | 1132 | CA | GLY | 234 | -20.766 | 2.767 | 16.072 | 1.00 | 19.45 | A |
| ATOM | 1133 | C | GLY | 234 | -20.545 | 3.241 | 14.625 | 1.00 | 19.67 | A |
| ATOM | 1134 | O | GLY | 234 | -21.299 | 2.980 | 13.715 | 1.00 | 23.81 | A |
| ATOM | 1135 | N | ALA | 235 | -19.405 | 3.926 | 14.368 | 1.00 | 18.89 | A |
| ATOM | 1136 | H | ALA | 235 | -19.096 | 4.485 | 15.135 | 1.00 | 15.00 | A |
| ATOM | 1137 | CA | ALA | 235 | -18.431 | 3.515 | 13.296 | 1.00 | 22.17 | A |
| ATOM | 1138 | CB | ALA | 235 | -18.193 | 2.042 | 13.039 | 1.00 | 6.68 | A |
| ATOM | 1139 | C | ALA | 235 | -18.540 | 4.160 | 11.993 | 1.00 | 21.96 | A |

FIG.17T

```
ATOM   1140  C    ALA  235   -18.486   5.385   12.100  1.00  26.42   A
ATOM   1141  N    SER  236   -18.699   3.498   10.787  1.00  20.94   A
ATOM   1142  H    SER  236   -18.824   4.326   10.254  1.00  15.00   A
ATOM   1143  CA   SER  236   -18.630   2.227    9.961  1.00  17.50   A
ATOM   1144  CB   SER  236   -19.905   1.876    9.160  1.00  14.98   A
ATOM   1145  OG   SER  236   -20.662   0.908    9.833  1.00  21.35   A
ATOM   1146  HG   SER  236   -21.599   0.910    9.647  1.00  15.00   A
ATOM   1147  C    SER  236   -17.794   2.538    8.714  1.00  13.65   A
ATOM   1148  O    SER  236   -17.939   3.614    8.131  1.00  16.29   A
ATOM   1149  N    VAL  237   -16.986   1.567    8.286  1.00  14.95   A
ATOM   1150  H    VAL  237   -16.764   0.823    8.949  1.00  15.00   A
ATOM   1151  CA   VAL  237   -16.201   1.802    7.077  1.00  11.42   A
ATOM   1152  CB   VAL  237   -14.681   2.004    7.284  1.00  12.49   A
ATOM   1153  CG1  VAL  237   -14.113   0.726    7.939  1.00  13.10   A
ATOM   1154  CG2  VAL  237   -14.254   3.396    7.846  1.00  10.27   A
ATOM   1155  C    VAL  237   -16.468   0.746    6.035  1.00   8.76   A
ATOM   1156  O    VAL  237   -16.827  -0.363    6.341  1.00  12.84   A
ATOM   1157  N    PHE  238   -16.354   1.158    4.773  1.00  12.45   A
ATOM   1158  H    PHE  238   -16.139   2.128    4.652  1.00  15.00   A
ATOM   1159  CA   PHE  238   -16.521   0.213    3.653  1.00  11.21   A
ATOM   1160  CB   PHE  238   -18.013   0.137    3.322  1.00  13.00   A
ATOM   1161  CG   PHE  238   -18.634   1.468    2.899  1.00  12.17   A
ATOM   1162  CD1  PHE  238   -18.763   1.812    1.518  1.00  12.94   A
ATOM   1163  CD2  PHE  238   -19.135   2.332    3.887  1.00  10.55   A
ATOM   1164  CE1  PHE  238   -19.407   3.010    1.092  1.00  14.01   A
ATOM   1165  CE2  PHE  238   -19.786   3.504    3.470  1.00  12.74   A
ATOM   1166  CZ   PHE  238   -19.917   3.836    2.100  1.00  13.17   A
ATOM   1167  C    PHE  238   -15.725   0.582    2.379  1.00  11.20   A
ATOM   1168  O    PHE  238   -15.137   1.638    2.267  1.00   8.73   A
ATOM   1169  N    VAL  239   -15.726  -0.300    1.383  1.00  14.34   A
ATOM   1170  H    VAL  239   -16.187  -1.170    1.523  1.00  15.00   A
ATOM   1171  CA   VAL  239   -14.982   0.027    0.154  1.00  14.65   A
ATOM   1172  CB   VAL  239   -13.900  -1.043   -0.162  1.00  14.09   A
ATOM   1173  CG1  VAL  239   -13.004  -1.318    1.038  1.00  14.55   A
ATOM   1174  CG2  VAL  239   -13.064  -0.594   -1.361  1.00  14.74   A
ATOM   1175  C    VAL  239   -15.930   0.081   -1.043  1.00  18.32   A
ATOM   1176  O    VAL  239   -16.558  -0.903   -1.369  1.00  18.99   A
ATOM   1177  N    ASN  240   -16.000   1.207   -1.707  1.00  19.26   A
ATOM   1178  H    ASN  240   -15.420   1.947   -1.383  1.00  15.00   A
ATOM   1179  CA   ASN  240   -16.613   1.355   -3.031  1.00  21.66   A
ATOM   1180  CB   ASN  240   -16.850   2.856   -3.095  1.00  24.58   A
ATOM   1181  CG   ASN  240   -18.167   3.077   -3.708  1.00  29.09   A
ATOM   1182  OD1  ASN  240   -18.948   2.123   -3.740  1.00  35.44   A
ATOM   1183  ND2  ASN  240   -18.293   4.331   -4.166  1.00  34.71   A
ATOM   1184  HD21 ASN  240   -19.149   4.489   -4.657  1.00  15.00   A
ATOM   1185  C    ASN  240   -15.669   0.950   -4.184  1.00  20.96   A
ATOM   1186  O    ASN  240   -14.473   1.128   -4.058  1.00  20.99   A
ATOM   1187  N    VAL  241   -16.189   0.383   -5.275  1.00  21.52   A
ATOM   1188  H    VAL  241   -17.182   0.230   -5.295  1.00  15.00   A
ATOM   1189  CA   VAL  241   -15.387   0.439   -6.516  1.00  20.56   A
ATOM   1190  CB   VAL  241   -14.581  -0.850   -6.849  1.00  18.02   A
ATOM   1191  CG1  VAL  241   -15.501  -2.058   -7.063  1.00  15.06   A
ATOM   1192  CG2  VAL  241   -13.597  -1.259   -5.764  1.00  20.05   A
ATOM   1193  C    VAL  241   -16.253   0.758   -7.741  1.00  18.88   A
ATOM   1194  O    VAL  241   -17.441   0.500   -7.819  1.00  18.63   A
ATOM   1195  N    THR  242   -15.541   1.162   -8.762  1.00  21.24   A
ATOM   1196  H    THR  242   -14.704   1.653   -8.486  1.00  15.00   A
ATOM   1197  CA   THR  242   -16.246   1.476  -10.031  1.00  20.63   A
ATOM   1198  CB   THR  242   -15.342   2.269  -10.981  1.00  15.80   A
ATOM   1199  CG1  THR  242   -14.035   1.663  -10.953  1.00  17.72   A
```

FIG.17U

| | | | | | | | | | | |
|---|---|---|---|---|---|---|---|---|---|---|
| ATOM | 1200 | HG1 | THR | 242 | -13.721 | 1.969 | -11.812 | 1.00 | 15.00 | A |
| ATOM | 1201 | CG2 | THR | 242 | -15.238 | 3.732 | -10.650 | 1.00 | 15.04 | A |
| ATOM | 1202 | C | THR | 242 | -16.755 | 0.240 | -10.783 | 1.00 | 18.92 | A |
| ATOM | 1203 | O | THR | 242 | -17.846 | 0.198 | -11.297 | 1.00 | 21.26 | A |
| ATOM | 1204 | N | ASP | 243 | -15.923 | -0.806 | -10.718 | 1.00 | 20.98 | A |
| ATOM | 1205 | H | ASP | 243 | -15.087 | -0.580 | -10.221 | 1.00 | 15.00 | A |
| ATOM | 1206 | CA | ASP | 243 | -16.092 | -1.977 | -11.628 | 1.00 | 21.28 | A |
| ATOM | 1207 | CB | ASP | 243 | -14.905 | -2.126 | -12.594 | 1.00 | 22.05 | A |
| ATOM | 1208 | CG | ASP | 243 | -14.932 | -0.954 | -13.492 | 1.00 | 28.23 | A |
| ATOM | 1209 | OD1 | ASP | 243 | -14.314 | 0.051 | -13.115 | 1.00 | 28.43 | A |
| ATOM | 1210 | OD2 | ASP | 243 | -15.588 | -1.033 | -14.535 | 1.00 | 33.00 | A |
| ATOM | 1211 | C | ASP | 243 | -16.123 | -3.308 | -10.923 | 1.00 | 20.38 | A |
| ATOM | 1212 | O | ASP | 243 | -15.148 | -4.072 | -10.967 | 1.00 | 20.43 | A |
| ATOM | 1213 | N | PRO | 244 | -17.204 | -3.553 | -10.154 | 1.00 | 19.92 | A |
| ATOM | 1214 | CD | PRO | 244 | -18.481 | -2.871 | -10.071 | 1.00 | 16.83 | A |
| ATOM | 1215 | CA | PRO | 244 | -17.120 | -4.706 | -9.269 | 1.00 | 19.13 | A |
| ATOM | 1216 | CB | PRO | 244 | -18.293 | -4.535 | -8.275 | 1.00 | 15.33 | A |
| ATOM | 1217 | CG | PRO | 244 | -18.890 | -3.174 | -8.634 | 1.00 | 15.21 | A |
| ATOM | 1218 | C | PRO | 244 | -16.975 | -6.034 | -9.974 | 1.00 | 19.29 | A |
| ATOM | 1219 | O | PRO | 244 | -16.194 | -6.859 | -9.548 | 1.00 | 23.48 | A |
| ATOM | 1220 | N | SER | 245 | -17.581 | -6.163 | -11.150 | 1.00 | 22.60 | A |
| ATOM | 1221 | H | SER | 245 | -18.220 | -5.459 | -11.473 | 1.00 | 15.00 | A |
| ATOM | 1222 | CA | SER | 245 | -17.414 | -7.429 | -11.942 | 1.00 | 25.50 | A |
| ATOM | 1223 | CB | SER | 245 | -18.256 | -7.369 | -13.234 | 1.00 | 21.36 | A |
| ATOM | 1224 | OG | SER | 245 | -19.667 | -7.567 | -12.981 | 1.00 | 38.26 | A |
| ATOM | 1225 | HG | SER | 245 | -19.848 | -7.390 | -12.038 | 1.00 | 15.00 | A |
| ATOM | 1226 | C | SER | 245 | -15.955 | -7.776 | -12.328 | 1.00 | 24.14 | A |
| ATOM | 1227 | O | SER | 245 | -15.477 | -8.859 | -12.623 | 1.00 | 24.84 | A |
| ATOM | 1228 | N | GLN | 246 | -15.177 | -6.689 | -12.385 | 1.00 | 28.52 | A |
| ATOM | 1229 | H | GLN | 246 | -15.638 | -5.804 | -12.265 | 1.00 | 15.00 | A |
| ATOM | 1230 | CA | GLN | 246 | -13.743 | -6.923 | -12.590 | 1.00 | 26.45 | A |
| ATOM | 1231 | CB | GLN | 246 | -13.144 | -5.645 | -13.233 | 1.00 | 29.90 | A |
| ATOM | 1232 | CG | GLN | 246 | -13.403 | -5.435 | -14.758 | 1.00 | 26.84 | A |
| ATOM | 1233 | CD | GLN | 246 | -14.862 | -5.341 | -15.129 | 1.00 | 21.60 | A |
| ATOM | 1234 | OE1 | GLN | 246 | -15.538 | -4.503 | -14.616 | 1.00 | 24.20 | A |
| ATOM | 1235 | NE2 | GLN | 246 | -15.334 | -6.234 | -15.975 | 1.00 | 26.15 | A |
| ATOM | 1236 | HE21 | GLN | 246 | -14.763 | -6.924 | -16.423 | 1.00 | 15.00 | A |
| ATOM | 1237 | HE22 | GLN | 246 | -16.320 | -6.119 | -16.084 | 1.00 | 15.00 | A |
| ATOM | 1238 | C | GLN | 246 | -12.936 | -7.372 | -11.363 | 1.00 | 27.14 | A |
| ATOM | 1239 | O | GLN | 246 | -11.721 | -7.570 | -11.454 | 1.00 | 25.73 | A |
| ATOM | 1240 | N | VAL | 247 | -13.615 | -7.395 | -10.196 | 1.00 | 23.70 | A |
| ATOM | 1241 | H | VAL | 247 | -14.600 | -7.594 | -10.146 | 1.00 | 15.00 | A |
| ATOM | 1242 | CA | VAL | 247 | -12.728 | -7.569 | -9.097 | 1.00 | 21.91 | A |
| ATOM | 1243 | CB | VAL | 247 | -13.156 | -6.814 | -7.859 | 1.00 | 21.59 | A |
| ATOM | 1244 | CG1 | VAL | 247 | -14.027 | -7.616 | -6.962 | 1.00 | 24.52 | A |
| ATOM | 1245 | CG2 | VAL | 247 | -13.680 | -5.409 | -8.167 | 1.00 | 21.61 | A |
| ATOM | 1246 | C | VAL | 247 | -12.258 | -8.998 | -8.910 | 1.00 | 21.55 | A |
| ATOM | 1247 | O | VAL | 247 | -12.946 | -9.912 | -9.251 | 1.00 | 19.53 | A |
| ATOM | 1248 | N | SER | 248 | -11.000 | -9.152 | -8.444 | 1.00 | 21.31 | A |
| ATOM | 1249 | H | SER | 248 | -10.558 | -8.342 | -8.070 | 1.00 | 15.00 | A |
| ATOM | 1250 | CA | SER | 248 | -10.414 | -10.499 | -8.327 | 1.00 | 21.97 | A |
| ATOM | 1251 | CB | SER | 248 | -8.939 | -10.571 | -8.828 | 1.00 | 23.61 | A |
| ATOM | 1252 | OG | SER | 248 | -8.860 | -9.952 | -10.128 | 1.00 | 20.21 | A |
| ATOM | 1253 | HG | SER | 248 | -9.752 | -10.027 | -10.496 | 1.00 | 15.00 | A |
| ATOM | 1254 | C | SER | 248 | -10.538 | -11.076 | -6.946 | 1.00 | 19.28 | A |
| ATOM | 1255 | O | SER | 248 | -10.048 | -10.409 | -6.052 | 1.00 | 20.64 | A |
| ATOM | 1256 | N | HIS | 249 | -11.269 | -12.204 | -6.814 | 1.00 | 18.72 | A |
| ATOM | 1257 | H | HIS | 249 | -11.284 | -12.753 | -7.674 | 1.00 | 15.00 | A |
| ATOM | 1258 | CA | HIS | 249 | -11.640 | -12.673 | -5.478 | 1.00 | 17.22 | A |
| ATOM | 1259 | CB | HIS | 249 | -13.080 | -13.152 | -5.484 | 1.00 | 13.10 | A |

FIG.17V

| | | | | | | | | | |
|---|---|---|---|---|---|---|---|---|---|
| ATOM | 1260 | CG | HIS | 249 | -13.919 | -11.905 | -5.550 | 1.00 10.13 | A |
| ATOM | 1261 | ND1 | HIS | 249 | -14.137 | -11.129 | -4.486 | 1.00 13.47 | A |
| ATOM | 1262 | HD1 | HIS | 249 | -13.720 | -11.294 | -3.611 | 1.00 15.00 | A |
| ATOM | 1263 | CD2 | HIS | 249 | -14.662 | -11.414 | -6.610 | 1.00 10.62 | A |
| ATOM | 1264 | NE2 | HIS | 249 | -15.317 | -10.347 | -6.134 | 1.00 15.51 | A |
| ATOM | 1265 | CE1 | HIS | 249 | -15.018 | -10.142 | -4.821 | 1.00 12.36 | A |
| ATOM | 1266 | C | HIS | 249 | -10.701 | -13.683 | -4.858 | 1.00 23.58 | A |
| ATOM | 1267 | O | HIS | 249 | -11.103 | -14.729 | -4.359 | 1.00 21.98 | A |
| ATOM | 1268 | N | GLY | 250 | -9.398 | -13.258 | -4.878 | 1.00 29.10 | A |
| ATOM | 1269 | H | GLY | 250 | -9.252 | -12.351 | -5.253 | 1.00 15.00 | A |
| ATOM | 1270 | CA | GLY | 250 | -8.410 | -14.041 | -4.115 | 1.00 24.27 | A |
| ATOM | 1271 | C | GLY | 250 | -8.336 | -15.372 | -4.743 | 1.00 25.93 | A |
| ATOM | 1272 | O | GLY | 250 | -8.940 | -15.520 | -5.795 | 1.00 29.26 | A |
| ATOM | 1273 | N | THR | 251 | -7.594 | -16.302 | -4.127 | 1.00 22.38 | A |
| ATOM | 1274 | H | THR | 251 | -7.485 | -17.038 | -4.804 | 1.00 15.00 | A |
| ATOM | 1275 | CA | THR | 251 | -7.111 | -16.139 | -2.725 | 1.00 21.12 | A |
| ATOM | 1276 | CB | THR | 251 | -6.988 | -17.525 | -1.933 | 1.00 24.76 | A |
| ATOM | 1277 | OG1 | THR | 251 | -5.877 | -17.641 | -0.981 | 1.00 22.90 | A |
| ATOM | 1278 | HG1 | THR | 251 | -6.063 | -18.366 | -0.381 | 1.00 15.00 | A |
| ATOM | 1279 | CG2 | THR | 251 | -6.968 | -18.722 | -2.890 | 1.00 22.77 | A |
| ATOM | 1280 | C | THR | 251 | -5.952 | -15.158 | -2.473 | 1.00 17.96 | A |
| ATOM | 1281 | O | THR | 251 | -4.969 | -15.043 | -3.213 | 1.00 12.30 | A |
| ATOM | 1282 | N | GLY | 252 | -6.241 | -14.367 | -1.419 | 1.00 16.85 | A |
| ATOM | 1283 | H | GLY | 252 | -7.093 | -14.432 | -0.862 | 1.00 15.00 | A |
| ATOM | 1284 | CA | GLY | 252 | -5.277 | -13.375 | -0.928 | 1.00 13.16 | A |
| ATOM | 1285 | C | GLY | 252 | -5.357 | -12.058 | -1.670 | 1.00 15.51 | A |
| ATOM | 1286 | O | GLY | 252 | -4.580 | -11.168 | -1.439 | 1.00 15.18 | A |
| ATOM | 1287 | N | PHE | 253 | -6.189 | -12.063 | -2.744 | 1.00 16.66 | A |
| ATOM | 1288 | H | PHE | 253 | -6.868 | -12.805 | -2.761 | 1.00 15.00 | A |
| ATOM | 1289 | CA | PHE | 253 | -6.110 | -10.892 | -3.651 | 1.00 15.77 | A |
| ATOM | 1290 | CB | PHE | 253 | -6.649 | -11.216 | -5.100 | 1.00 17.11 | A |
| ATOM | 1291 | CG | PHE | 253 | -5.595 | -11.840 | -5.994 | 1.00 11.82 | A |
| ATOM | 1292 | CD1 | PHE | 253 | -4.385 | -11.175 | -6.231 | 1.00 13.69 | A |
| ATOM | 1293 | CD2 | PHE | 253 | -5.845 | -13.089 | -6.558 | 1.00 18.59 | A |
| ATOM | 1294 | CE1 | PHE | 253 | -3.364 | -11.771 | -6.993 | 1.00 14.39 | A |
| ATOM | 1295 | CE2 | PHE | 253 | -4.840 | -13.680 | -7.363 | 1.00 21.37 | A |
| ATOM | 1296 | CZ | PHE | 253 | -3.612 | -13.014 | -7.562 | 1.00 15.72 | A |
| ATOM | 1297 | C | PHE | 253 | -6.740 | -9.599 | -3.147 | 1.00 13.88 | A |
| ATOM | 1298 | O | PHE | 253 | -6.347 | -8.477 | -3.453 | 1.00 14.27 | A |
| ATOM | 1299 | N | THR | 254 | -7.865 | -9.837 | -2.502 | 1.00 14.00 | A |
| ATOM | 1300 | H | THR | 254 | -8.079 | -10.748 | -2.124 | 1.00 15.00 | A |
| ATOM | 1301 | CA | THR | 254 | -8.741 | -8.681 | -2.185 | 1.00 14.09 | A |
| ATOM | 1302 | CB | THR | 254 | -9.908 | -8.469 | -3.201 | 1.00 11.66 | A |
| ATOM | 1303 | OG1 | THR | 254 | -9.414 | -8.325 | -4.536 | 1.00 13.08 | A |
| ATOM | 1304 | HG1 | THR | 254 | -9.826 | -9.054 | -4.992 | 1.00 15.00 | A |
| ATOM | 1305 | CG2 | THR | 254 | -10.882 | -7.321 | -2.885 | 1.00 13.78 | A |
| ATOM | 1306 | C | THR | 254 | -9.270 | -8.779 | -0.738 | 1.00 12.36 | A |
| ATOM | 1307 | O | THR | 254 | -9.906 | -9.695 | -0.240 | 1.00 14.54 | A |
| ATOM | 1308 | N | SER | 255 | -9.007 | -7.683 | -0.027 | 1.00 13.42 | A |
| ATOM | 1309 | H | SER | 255 | -8.425 | -7.021 | -0.490 | 1.00 15.00 | A |
| ATOM | 1310 | CA | SER | 255 | -9.032 | -7.725 | 1.431 | 1.00 7.59 | A |
| ATOM | 1311 | CB | SER | 255 | -7.793 | -8.466 | 1.976 | 1.00 6.39 | A |
| ATOM | 1312 | OG | SER | 255 | -6.704 | -7.560 | 2.041 | 1.00 9.69 | A |
| ATOM | 1313 | HG | SER | 255 | -5.920 | -8.031 | 1.741 | 1.00 15.00 | A |
| ATOM | 1314 | C | SER | 255 | -9.248 | -6.341 | 2.085 | 1.00 10.05 | A |
| ATOM | 1315 | O | SER | 255 | -9.191 | -5.254 | 1.492 | 1.00 15.21 | A |
| ATOM | 1316 | N | PHE | 256 | -9.653 | -6.385 | 3.369 | 1.00 8.54 | A |
| ATOM | 1317 | H | PHE | 256 | -9.700 | -7.323 | 3.733 | 1.00 15.00 | A |
| ATOM | 1318 | CA | PHE | 256 | -10.114 | -5.168 | 4.035 | 1.00 7.94 | A |
| ATOM | 1319 | CB | PHE | 256 | -11.605 | -5.009 | 3.679 | 1.00 11.65 | A |

FIG.17W

| | | | | | | | | | |
|---|---|---|---|---|---|---|---|---|---|
| ATOM | 1320 | CG | PHE | 256 | -12.376 | -3.824 | 4.235 | 1.00 | 8.72 | A |
| ATOM | 1321 | CD1 | PHE | 256 | -11.766 | -2.570 | 4.533 | 1.00 | 11.20 | A |
| ATOM | 1322 | CD2 | PHE | 256 | -13.756 | -3.976 | 4.327 | 1.09 | 6.12 | A |
| ATOM | 1323 | CE1 | PHE | 256 | -12.503 | -1.490 | 5.034 | 1.00 | 11.49 | A |
| ATOM | 1324 | CE2 | PHE | 256 | -14.514 | -2.849 | 4.734 | 1.00 | 6.86 | A |
| ATOM | 1325 | CZ | PHE | 256 | -13.862 | -1.657 | 5.211 | 1.00 | 9.27 | A |
| ATOM | 1326 | C | PHE | 256 | -9.933 | -5.268 | 5.560 | 1.00 | 11.92 | A |
| ATOM | 1327 | O | PHE | 256 | -10.195 | -6.290 | 6.177 | 1.00 | 9.43 | A |
| ATOM | 1328 | N | GLY | 257 | -9.420 | -4.207 | 6.169 | 1.00 | 10.57 | A |
| ATOM | 1329 | H | GLY | 257 | -9.217 | -3.365 | 5.653 | 1.00 | 15.00 | A |
| ATOM | 1330 | CA | GLY | 257 | -9.368 | -4.406 | 7.612 | 1.00 | 11.26 | A |
| ATOM | 1331 | C | GLY | 257 | -8.965 | -3.122 | 8.287 | 1.00 | 11.14 | A |
| ATOM | 1332 | O | GLY | 257 | -8.916 | -2.068 | 7.679 | 1.00 | 10.81 | A |
| ATOM | 1333 | N | LEU | 258 | -8.688 | -3.277 | 9.565 | 1.00 | 12.61 | A |
| ATOM | 1334 | H | LEU | 258 | -8.776 | -4.204 | 9.943 | 1.00 | 15.00 | A |
| ATOM | 1335 | CA | LEU | 258 | -8.434 | -2.098 | 10.426 | 1.00 | 14.72 | A |
| ATOM | 1336 | CB | LEU | 258 | -9.751 | -1.212 | 10.704 | 1.00 | 14.67 | A |
| ATOM | 1337 | CG | LEU | 258 | -10.991 | -1.863 | 11.379 | 1.00 | 18.02 | A |
| ATOM | 1338 | CD1 | LEU | 258 | -12.317 | -1.125 | 11.094 | 1.00 | 15.05 | A |
| ATOM | 1339 | CD2 | LEU | 258 | -10.743 | -2.047 | 12.905 | 1.00 | 15.42 | A |
| ATOM | 1340 | C | LEU | 258 | -7.737 | -2.525 | 11.709 | 1.00 | 11.84 | A |
| ATOM | 1341 | O | LEU | 258 | -7.851 | -3.690 | 12.096 | 1.00 | 7.91 | A |
| ATOM | 1342 | N | LEU | 259 | -7.058 | -1.537 | 12.343 | 1.00 | 11.64 | A |
| ATOM | 1343 | H | LEU | 259 | -6.883 | -0.685 | 11.844 | 1.00 | 15.00 | A |
| ATOM | 1344 | CA | LEU | 259 | -6.581 | -1.780 | 13.714 | 1.00 | 9.53 | A |
| ATOM | 1345 | CB | LEU | 259 | -5.155 | -2.417 | 13.831 | 1.00 | 7.40 | A |
| ATOM | 1346 | CG | LEU | 259 | -4.194 | -1.621 | 12.931 | 1.00 | 11.40 | A |
| ATOM | 1347 | CD1 | LEU | 259 | -3.355 | -2.412 | 11.926 | 1.00 | 7.83 | A |
| ATOM | 1348 | CD2 | LEU | 259 | -3.379 | -0.670 | 13.808 | 1.00 | 13.30 | A |
| ATOM | 1349 | C | LEU | 259 | -6.652 | -0.497 | 14.531 | 1.00 | 10.40 | A |
| ATOM | 1350 | O | LEU | 259 | -6.202 | 0.556 | 14.082 | 1.00 | 9.73 | A |
| ATOM | 1351 | N | LYS | 260 | -7.193 | -0.629 | 15.762 | 1.00 | 12.00 | A |
| ATOM | 1352 | H | LYS | 260 | -7.395 | -1.553 | 16.115 | 1.00 | 15.00 | A |
| ATOM | 1353 | CA | LYS | 260 | -7.069 | 0.521 | 16.693 | 1.00 | 13.51 | A |
| ATOM | 1354 | CB | LYS | 260 | -8.014 | 0.312 | 17.885 | 1.00 | 13.49 | A |
| ATOM | 1355 | CG | LYS | 260 | -8.378 | 1.656 | 18.521 | 1.00 | 17.16 | A |
| ATOM | 1356 | CD | LYS | 260 | -9.435 | 1.456 | 19.596 | 1.00 | 12.01 | A |
| ATOM | 1357 | CE | LYS | 260 | -10.151 | 2.681 | 20.121 | 1.00 | 11.41 | A |
| ATOM | 1358 | NZ | LYS | 260 | -9.175 | 3.595 | 20.697 | 1.00 | 13.33 | A |
| ATOM | 1359 | HZ1 | LYS | 260 | -8.534 | 3.932 | 19.954 | 1.00 | 15.00 | A |
| ATOM | 1360 | HZ2 | LYS | 260 | -9.693 | 4.404 | 21.095 | 1.00 | 15.00 | A |
| ATOM | 1361 | HZ3 | LYS | 260 | -8.638 | 3.136 | 21.458 | 1.00 | 15.00 | A |
| ATOM | 1362 | C | LYS | 260 | -5.648 | 0.921 | 17.125 | 1.00 | 16.54 | A |
| ATOM | 1363 | O | LYS | 260 | -4.828 | 0.112 | 17.481 | 1.00 | 15.61 | A |
| ATOM | 1364 | N | LEU | 261 | -5.353 | 2.199 | 17.015 | 1.00 | 14.78 | A |
| ATOM | 1365 | H | LEU | 261 | -6.089 | 2.838 | 16.856 | 1.00 | 15.00 | A |
| ATOM | 1366 | CB | LEU | 261 | -3.705 | 4.005 | 17.185 | 1.00 | 19.53 | A |
| ATOM | 1367 | CG | LEU | 261 | -3.177 | 4.309 | 15.787 | 1.00 | 16.82 | A |
| ATOM | 1368 | CD1 | LEU | 261 | -3.010 | 5.779 | 15.767 | 1.00 | 12.45 | A |
| ATOM | 1369 | CD2 | LEU | 261 | -4.010 | 3.906 | 14.577 | 1.00 | 18.20 | A |
| ATOM | 1370 | C | LEU | 261 | -4.243 | 2.667 | 19.225 | 1.00 | 20.80 | A |
| ATOM | 1371 | OCT1 | LEU | 261 | -5.363 | 2.741 | 19.746 | 1.00 | 22.59 | A |
| ATOM | 1372 | OCT2 | LEU | 261 | -3.221 | 2.696 | 19.913 | 1.00 | 26.97 | A |
| ATOM | 1373 | CA | LEU | 261 | -4.122 | 2.604 | 17.684 | 1.00 | 18.13 | A |
| ATOM | 1374 | O | HOH | 501 | -20.040 | 9.837 | 7.596 | 1.00 | 16.33 | W |
| ATOM | 1375 | H1 | HOH | 501 | -19.411 | 10.547 | 7.803 | 1.00 | 10.00 | W |
| ATOM | 1376 | H2 | HOH | 501 | -19.615 | 9.317 | 6.900 | 1.00 | 10.00 | W |
| ATOM | 1377 | O | HOH | 502 | -9.727 | 11.545 | 10.743 | 1.00 | 10.94 | W |
| ATOM | 1378 | H1 | HOH | 502 | -10.039 | 11.934 | 9.919 | 1.00 | 15.00 | W |
| ATOM | 1379 | H2 | HOH | 502 | -10.233 | 12.125 | 11.315 | 1.00 | 15.00 | W |

FIG.17X

```
ATOM   1380  O   HOH  503    -8.158   13.188   13.681  1.00  30.64   W
ATOM   1381  H1  HOH  503    -8.715   12.529   13.277  1.00  15.00   W
ATOM   1382  H2  HOH  503    -8.700   13.944   13.574  1.00  15.00   W
ATOM   1383  O   HOH  504   -16.772    8.440   12.789  1.00  10.00   W
ATOM   1384  H1  HOH  504   -17.194    9.259   12.886  1.00  10.00   W
ATOM   1385  H2  HOH  504   -15.921    8.763   12.582  1.00  10.00   W
ATOM   1386  O   HOH  505   -25.173    7.297    7.925  1.00  47.03   W
ATOM   1387  H1  HOH  505   -24.690    8.064    8.239  1.00  10.00   W
ATOM   1388  H2  HOH  505   -25.990    7.684    7.583  1.00  10.00   W
ATOM   1389  O   HOH  506   -23.612   14.949   13.859  1.00  36.14   W
ATOM   1390  H1  HOH  506   -24.160   15.702   13.605  1.00  10.00   W
ATOM   1391  H2  HOH  506   -23.282   15.191   14.748  1.00  10.00   W
ATOM   1392  O   HOH  507   -17.329   -8.460   -7.186  1.00  34.02   W
ATOM   1393  O   HOH  508   -18.687   -7.253   -3.843  1.00  63.14   W
ATOM   1394  O   HOH  509    -7.157   11.327    3.239  1.00  22.26   W
ATOM   1395  O   HOH  510   -19.322    7.486   -2.227  1.00  37.69   W
ATOM   1396  O   HOH  511   -14.645   -7.711   -1.931  1.00  26.48   W
ATOM   1397  O   HOH  512   -18.377   -9.754   12.556  1.00  24.86   W
ATOM   1398  O   HOH  513     0.030    0.048  -13.455  1.00  26.05   W
ATOM   1399  O   HOH  514    -8.938    5.945   22.862  1.00  34.39   W
ATOM   1400  O   HOH  515   -29.446   -4.922   -7.247  1.00  41.61   W
ATOM   1401  O   HOH  516   -12.982   10.220   10.038  1.00  47.16   W
ATOM   1402  O   HOH  517   -21.797   -9.377    7.242  1.00  60.65   W
ATOM   1403  O   HOH  518    -7.867    8.165   19.484  1.00  40.46   W
ATOM   1404  O   HOH  520   -15.588  -14.701   14.628  1.00  63.80   W
ATOM   1405  O   HOH  521   -21.844    7.778   20.415  1.00  35.72   W
ATOM   1406  O   HOH  522    -6.555   -3.308  -15.790  1.00  33.63   W
ATOM   1407  O   HOH  523    -9.046  -13.476   -8.051  1.00  44.08   W
ATOM   1408  O   HOH  524   -17.413   -9.311   17.071  1.00  34.06   W
ATOM   1409  O   HOH  525   -23.838    4.781   19.884  1.00  37.99   W
ATOM   1410  O   HOH  526   -26.323   15.525   10.379  1.00  72.49   W
ATOM   1411  O   HOH  527    -3.167  -13.749  -10.820  1.00  43.99   W
ATOM   1412  O   HOH  528    -0.470    2.513   17.943  1.00  63.68   W
ATOM   1413  O   HOH  529    -5.580  -12.778  -14.864  1.00  47.52   W
ATOM   1414  O   HOH  530    -2.641    7.004    2.495  1.00  18.07   W
ATOM   1415  O   HOH  531    -6.472   12.847    0.156  1.00  24.96   W
ATOM   1416  O   HOH  532   -10.363  -16.426   -0.360  1.00  63.56   W
ATOM   1417  O   HOH  533    -1.378  -17.183  -13.053  1.00  67.67   W
ATOM   1418  O   HOH  534    -4.774    9.073   -0.651  1.00  23.36   W
ATOM   1419  O   HOH  535   -18.917  -13.857    6.913  1.00  32.28   W
ATOM   1420  O   HOH  536   -23.062    3.270    0.454  1.00  52.03   W
ATOM   1421  O   HOH  537   -25.906    9.022   16.986  1.00  44.75   W
ATOM   1422  O   HOH  538   -21.729   16.972   17.027  1.00  53.12   W
ATOM   1423  O   HOH  539    -9.034   11.806   17.034  1.00  70.90   W
ATOM   1424  O   HOH  540   -10.938  -13.296   15.207  1.00  35.65   W
ATOM   1425  O   HOH  541    -6.068   13.255   17.989  1.00  67.36   W
ATOM   1426  O   HOH  542   -20.593  -11.039   -9.003  1.00  96.30   W
ATOM   1427  O   HOH  543   -15.326   13.397    1.269  1.00  35.72   W
ATOM   1428  O   HOH  544   -24.591   -7.285   -2.353  1.00  43.42   W
ATOM   1429  O   HOH  545   -25.859   -2.656  -15.747  1.00  53.56   W
ATOM   1430  O   HOH  546   -23.074   -1.533   11.026  1.00  56.44   W
ATOM   1431  O   HOH  548    -8.941  -12.649  -12.394  1.00  64.34   W
ATOM   1432  O   HOH  549   -14.150    6.038  -12.250  1.00  41.38   W
ATOM   1433  O   HOH  550   -14.274   -0.613   18.441  1.00  56.17   W
ATOM   1434  O   HOH  551   -12.241  -19.609    8.637  1.00  80.90   W
ATOM   1435  O   HOH  552   -10.316   15.578   10.166  1.00  39.58   W
ATOM   1436  O   HOH  553   -15.367   10.941   14.659  1.00  40.40   W
ATOM   1437  O   HOH  554    -2.322    1.830   -5.294  1.00  33.65   W
ATOM   1438  O   HOH  555   -22.393  -14.875   -4.217  1.00  52.40   W
ATOM   1439  O   HOH  556   -22.120   14.279    7.169  1.00  38.55   W
```

FIG.17Y

```
ATOM   1440  O   HOH  557   -28.833    6.135    9.560  1.00  37.40    W
ATOM   1441  O   HOH  558    -5.554  -16.509   13.192  1.00  88.88    W
ATOM   1442  O   HOH  559   -22.996   12.522    1.162  1.00  63.77    W
ATOM   1443  O   HOH  560   -13.764    2.268  -14.743  1.00  27.47    W
ATOM   1444  O   HOH  561   -15.556    7.750   -5.628  1.00  75.88    W
ATOM   1445  O   HOH  562    -1.970  -15.363  -17.719  1.00  76.30    W
ATOM   1446  O   HOH  563   -18.939   -0.335  -13.842  1.00  48.39    W
ATOM   1447  O   HOH  564   -12.619   14.760   -6.974  1.00 100.59    W
ATOM   1448  O   HOH  565    -9.491   18.046   13.682  1.00  87.45    W
ATOM   1449  O   HOH  566   -11.655  -11.140   22.481  1.00  28.88    W
ATOM   1450  O   HOH  567   -24.072   -3.264   -0.332  1.00  35.13    W
ATOM   1451  O   HOH  568   -27.455    0.119   -7.117  1.00  71.07    W
ATOM   1452  O   HOH  569   -14.604    3.516   -6.119  1.00  59.45    W
ATOM   1453  O   HOH  570    -2.635   -9.566  -16.973  1.00  59.09    W
ATOM   1454  O   HOH  571   -18.841    4.066   -7.543  1.00  34.10    W
ATOM   1455  O   HOH  572   -24.996    1.301   17.953  1.00  70.45    W
ATOM   1456  O   HOH  573   -14.666   16.471    8.995  1.00  62.77    W
ATOM   1457  O   HOH  574   -14.786    1.426   10.949  1.00  82.68    W
ATOM   1458  O   HOH  575   -16.584  -14.717   -4.352  1.00  29.09    W
ATOM   1459  O   HOH  576   -16.273   -4.590    6.109  1.00 104.64    W
ATOM   1460  O   HOH  577   -25.471   -0.127   -2.510  1.00  62.74    W
ATOM   1461  O   HOH  578    -7.334  -17.173   19.514  1.00  89.62    W
ATOM   1462  O   HOH  579   -21.060   14.259   19.996  1.00  69.59    W
ATOM   1463  O   HOH  580   -19.286    4.057  -12.816  1.00  60.37    W
ATOM   1464  O   HOH  581   -22.445  -15.840    0.317  1.00  58.24    W
ATOM   1465  O   HOH  582   -22.434  -10.539   12.489  1.00  70.25    W
ATOM   1466  O   HOH  583   -21.327    3.668   -2.500  1.00  39.32    W
ATOM   1467  O   HOH  584   -25.325    5.247   16.919  1.00  41.31    W
ATOM   1468  O   HOH  585   -24.945  -10.718   -2.375  1.00  38.85    W
ATOM   1469  O   HOH  586   -24.342  -13.003    1.927  1.00  70.58    W
ATOM   1470  O   HOH  587   -18.020   11.871   11.358  1.00  64.47    W
ATOM   1471  O   HOH  588   -27.135    6.965   13.151  1.00  53.96    W
ATOM   1472  O   HOH  589   -14.982  -16.230   -2.494  1.00  30.24    W
ATOM   1473  O   HOH  590    -5.646   14.418   -2.232  1.00  41.78    W
ATOM   1474  O   HOH  591    -2.745   -0.153  -17.104  1.00  55.19    W
ATOM   1475  O   HOH  592    -3.397   -7.012   22.477  1.00  59.46    W
ATOM   1476  O   HOH  593   -32.916   -4.705   -4.143  1.00  51.88    W
ATOM   1477  O   HOH  594   -10.913  -18.855   -3.503  1.00  42.29    W
ATOM   1478  O   HOH  595   -24.157    1.821   -6.165  1.00  47.43    W
END
```

THERAPEUTIC APPLICATIONS FOR THE ANTI-T-BAM (CD40-L) MONOCLONAL ANTIBODY 5C8 IN THE TREATMENT OF REPERFUSION INJURY IN NON-TRANSPLANT RECIPIENTS

This application is a continuation-in-part of U.S. application Ser. No. 08/567,391, filed Dec. 1, 1995 and Ser. No. 08/566,258, filed Dec. 1, 1995, both abandoned, the contents of which are hereby incorporated by reference into the present application.

The invention disclosed herein was made with Government support under NIH Grant Nos. K08-AR-01904, RO1-CA55713, RO1-AI-28367, RO1-AI-14969, HL21006, HL42833, HL50629, and RO1-AI-14969 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found in the text or at the end of this application, preceding the sequence listing and claims.

BACKGROUND OF THE INVENTION

CD40 is a 50 kDa cell surface molecule originally described as being expressed on B cells and some epithelial carcinomas (1, 2). CD40 interacts with CD40L (T-BAM, gp39, TRAP), a 30 kDa cell surface molecule transiently expressed on activated $CD4^+$ T cells (3–8). CD40L-CD40 interactions have been extensively studied in the context of T cell-B cell interactions. CD40 ligation plays key roles in B cell activation, proliferation, differentiation, Ig production and rescue from apoptotic signals (9–11). The critical in vivo role of CD40 ligation in B cell differentiation is highlighted by the hyper-IgM syndrome, a humoral immunodeficiency due to mutations in the gene encoding CD40L (12–16). Murine CD40 (17) or CD40L (18) "knockouts" have similar phenotypes to patients with the hyper-IgM syndrome.

Interestingly, recent studies indicate that CD40 expression has a broader cellular distribution than originally described. CD40 has been shown to be expressed on monocytes (19), dendritic cells (22), epithelium (23, 21), basophils (24), and Hodgkin's tumor cells (25). Moreover, various cytokines can regulate CD40 expression on non-B cells. CD40 expression on thymic epithelial cells is upregulated by IL-1α, TNF-α or INF-γ (21). INF-γ, in addition to IL-3 or GM-CSF, similarly upregulates CD40 expression on monocytes (19). Ligation of CD40 in the presence of INF-γ and IL-1α stimulates GM-CSF production by thymic epithelial cells (21). In addition, CD40L expressing transfectants induce tumoricidal activity by monocytes and, in the presence of INF-γ, GM-CSF or IL-3, stimulate monocytes to secrete TNF-γ, IL-6 or IL-8 (19).

CD40 is also expressed on cells found within synovial membrane (SM) in patients afflicted with rheumatoid, arthritis (RA). An immunohistological survey of cell surface molecules expressed in RA SM found that CD40 was expressed on a variety of cell types, including cells with fibroblast-like morphology (26). In this report it is shown by FACS analysis that CD40 is expressed on cultured synovial membrane (SM) fibroblasts isolated from patients with RA, non-RA inflammatory arthritis (IA) or osteoarthritis (OA). In addition, dermal fibroblasts isolated from normal donors also express CD40. Moreover, CD40 ligation by $CD40L^+$ cells induces fibroblast activation and proliferation.

Endothelial cells express surface molecules, such as CD54 (ICAM-1), CD62E (E-selectin) and CD106 (VCAM-1), that mediate adhesive interactions with leukocytes (27–35). The expression of endothelial cell surface adhesion molecules orchestrates recruitment of leukocytes to sites of inflammation and therefore is subject to tight regulation (27, 28). Resting endothelial cells express low levels of CD54 and minimal or no CD62E or CD106. Following activation with IL-1, TNFα, or LPS, endothelial cells rapidly upregulate CD54, CD62E and CD106 expression (27, 28). $CD4^+$ T cells may contribute to upregulation of endothelial cell surface adhesion molecules by inducing endothelial cells or other target cells to secrete IL-1 or TNFα (36). However, the molecular details involved in $CD4^+$ T cell-endothelial cell interactions that induce endothelial cell activation have not been completely delineated.

It can now be reported that normal human endothelial cells also express CD40 in situ and CD40L-CD40 interactions induce endothelial cell activation in vitro. Frozen sections from normal spleen, thyroid, skin, muscle, kidney, lung or umbilical cord were studied for CD40 expression by immunohistochemistry. Endothelial cells from all tissues studied express CD40 in situ. Moreover, human umbilical vein endothelial cells (HUVEC) express CD40 in vitro and rIFN-γ induces HUVEC CD40 upregulation. CD40 expression on HUVEC is functionally significant because $CD40L^+$ Jurkat T cells upregulate HUVEC CD54 (ICAM-1), CD62E (E-selectin) and CD106 (VCAM-1) expression in vitro in a manner inhibited by anti-CD40L mAb 5C8. Additionally, CD40L expressing 293 kidney cell transfectants, but not control transfectants, also upregulate CD54, CD62E and CD106 expression on HUVEC. These results demonstrate that CD40L-CD40 interactions induce endothelial cell activation in vitro. It is shown for the first time that CD40L expressed on the surface of T cells induces activation of $CD40^+$ endothelial cells and that this activation is inhibited by an anti-CD40L monoclonal antibody. Moreover, these results demonstrate a mechanism by which activated $CD4^+$ T cells augment inflammatory responses in vivo by upregulating the expression of endothelial cell surface adhesion molecules.

SUMMARY OF THE INVENTION

This invention provides a method of inhibiting activation by CD40 ligand of cells bearing CD40 on the cell surface, comprising contacting the cells with an agent capable of inhibiting interaction between CD40 ligand and the cells, in an amount effective to inhibit activation of the cells.

This invention provides a method of inhibiting activation by CD40 ligand of cells bearing CD40 on the cell surface, in a subject, comprising administering to the subject an agent capable of inhibiting interaction between CD40 ligand and the cells, in an amount effective to inhibit activation of the cells in the subject.

DESCRIPTION OF THE FIGURES

FIGS. 1A–B. CD40 expression on SM fibroblasts. Shown are FACS analyses of CD40, CD14, CD45 or MHC Class II expression, as indicated, on representative RA or OA SM adherent cells following the first passage in vitro. The X-axis represents mean fluorescence intensity (MFI) and the Y-axis represents cell number. For RA cells, the MFI of CD40 expression or isotype control mAb was 21 and 9, respectively. For OA cells, the MFI of CD40 expression or isotype control mAb was 33 and 9, respectively.

FIGS. 2A–F. CD40 expression on resting or rINF-γ stimulated dermal fibroblasts. Shown are FACS analyses of CD40, CD54 or control mAb staining, as indicated, on 3 dermal fibroblast lines. The cells were cultured in the presence or absence of rINF-γ (1000 U/ml) for 24 hours. SK.1 and SK.2 were studied following the second passage and CCD 965 SK was studied following the third passage in culture. The X-axis represents mean fluorescence intensity (MFI) and the Y-axis represents cell number. The number in the upper right hand corner of each graph indicates CD40 MFI (background subtracted).

FIG. 6A. Effect of CD40L-CD40 interactions on fibroblast IL-6 secretion. Shown are bar graphs indicating $^3$H-thymidine incorporation by the IL-6 indicator cell line B9 following the additions of supernatants (final dilution 1:60) from SM fibroblasts cultured with media alone, CD40L⁺ D1.1 cells in the presence or absence of anti-CD40L mAb 5C8 or control mAb P1.17, CD40L⁻ B2.7 cells or CD40L⁺ B2.7 transfectants. The proliferative responses of B9 cells cultured with control supernatants from D1.1 cells, B2.7 cells or CD40L⁺ B2.7 transfectants were 1136 cpm (±113), 2398 cpm (±263) and 1131 cpm (±56). Similar results were obtained with 3 additional SM fibroblast lines.

FIG. 7. Effect of CD40 ligation on SM fibroblast proliferation. Shown are bar graphs from 2 separate experiments demonstrating SM fibroblast $^3$H-thymidine incorporation following coculture in 1% FM with mitomycin-C treated CD40L- Jurkat B2.7 cells or CD40L⁺ Jurkat B2.7 transfectants for 48 hours. Where indicated, CD40L⁺ Jurkat B2.7 transfectants were pretreated with anti-CD40L mAb 5C8 (5 μg/ml) or P1.17 control mAb (5 μg/ml) prior to the addition to fibroblasts. In the experiment studying RA.5 proliferation, the proliferation of CD40L⁻ Jurkat B2.7 cells or CD40L⁺ Jurkat B2.7 transfectants was 51±7 cpm and 39±3 cpm, respectively. In the experiment studying OA.6 proliferation, the proliferation of CD40L⁻ Jurkat B2.7 cells or CD40L⁺ Jurkat B2.7 transfectants was 243±5 cpm and 453±95 cpm, respectively. Background proliferation is subtracted in coculture experiments. Also shown are the proliferative responses of fibroblasts following culture in 1% FM or 10% FM. Similar results were obtained in 3 additional experiments. Error bars show observed error.

FIGS. 15A–L. Effect of CD40L expressing 293 kidney cell transfectants on HUVEC CD54, CD62E and CD106 expression. Shown are two-color contour graphs demonstrating the effects on HUVEC CD54, CD62E and CD106 expression following culture with media, CD40L+ Jurkat D1.1 cells, CD8+ 293 kidney cell transfectants or CD40L− 293 kidney cell transfectants for 6 hours. The X-axis demonstrates UEA-1 expression and the Y-axis demonstrates CD54 (left panel), CD106 (middle panel) or CD62E (right panel) expression. The numbers in the upper right hand corner of each graph indicates the percentage of UEA-1+ cells expressing CD54, CD106 or CD62E, as indicated (background staining of control mAb is subtracted for each value). Shown is representative of 3 similar experiments with different HUVEC lines.

FIG. 16A. Kinetic analysis of CD40L induced HUVEC CD54, CD62E and CD106 upregulation. Shown are the percentage of HUVEC expressing CD54, CD62E, or CD106 following culture with CD40L+ Jurkat D1.1 cells for 6 or 24 hours. The percentage of HUVEC expressing CD54, CD62E or CD106 was determined by two-color FACS analysis (background staining of control mAb is subtracted for each value). Shown is representative of 3 similar experiments with different HUVEC lines.

FIGS. 17A–Y: Atomic coordinates of crystal structure of soluble extracellular fragment of human CD40L containing residues Gly116-Leu261 of SEQ ID NO:1 (in Brookhaven Protein Data Bank format).

DETAILED DESCRIPTION

Figure 3:
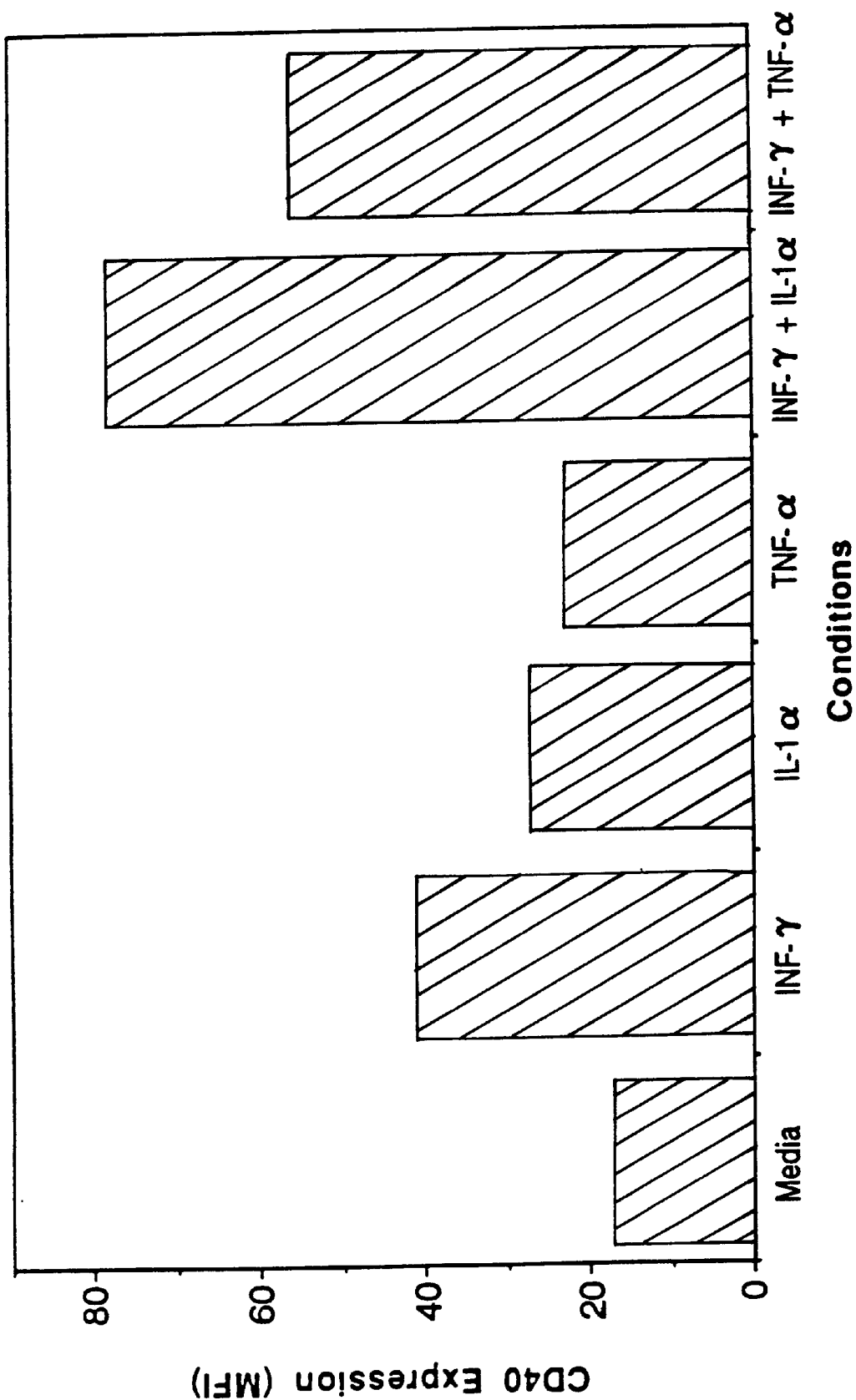
FIG. 3. Cytokine regulation of SM fibroblast CD40 expression. Shown is a bar graph representing CD40 mean fluorescence intensity (MFI) on a SM fibroblast line (OA.3) following co-culture with rINF-γ (1000 U/ml), rIL-1α (10 pg/ml), rTNF-α (200 U/ml) or combinations of cytokines, as indicated. CD40 expression was determined by FACS analysis and background staining with a control mAb is subtracted for each value. The experiment shown is representative of 3 similar experiments performed.
Figure 4A:
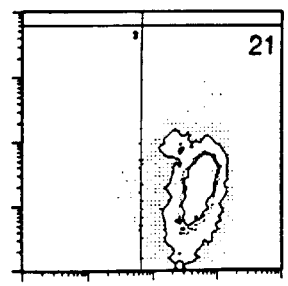
FIGS. 4A–F. Effect of CD40L-CD40 interactions on SM fibroblast CD54 (ICAM-1) expression. Shown are two-color contour graphs demonstrating CD13 expression (X-axis) or CD54 expression (Y-axis) on IA.1 SM fibroblasts cultured 24 hours with media, rINF-γ (1000 U/ml), CD40L⁻ Jurkat B2.7 cells or CD40L⁺ Jurkat D1.1 cells in the presence or absence of anti-CD40L mAb 5C8 or control mAb P1.17. The number in the upper right hand corner of each graph represents CD54 mean fluorescence intensity (MFI). The background MFI of an isotype control mAb is subtracted from each value. The experiment shown is representative of 3 similar experiments performed.
Figure 4B:
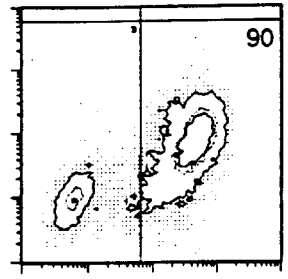
Figure 4C:
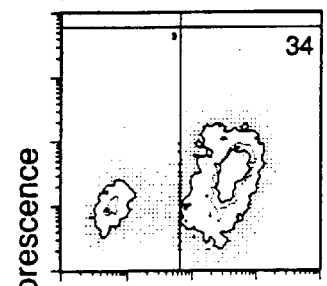
Figure 4D:
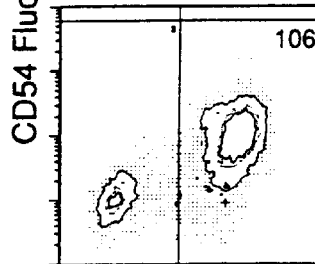
Figure 4E:
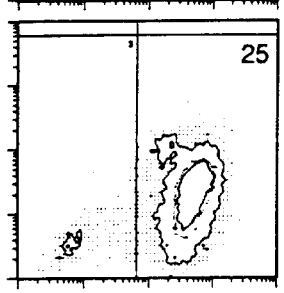
Figure 4F:
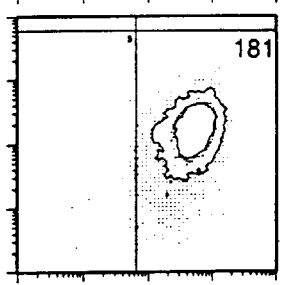

This invention provides a method of inhibiting activation by CD40 ligand of cells bearing CD40 on the cell surface, comprising contacting the cells with an agent capable of inhibiting interaction between CD40 ligand and the cells, in an amount effective to inhibit activation of the cells. In one embodiment, the cells bearing CD40 on the cell surface are cells other than B cells. In another embodiment, they are plasma cells, including differentiated plasma cells such as myeloma cells.

This method may be used to inhibit activation of CD40-bearing cells either in vivo or ex vivo. "Interaction between CD40 ligand and CD40 on the cells" refers to one or more aspects, functional or structural, of a CD40-CD40 ligand interrelationship. Therefore, in one embodiment, an agent which inhibits interaction may competitively bind to CD40 ligand in such a way to block or diminish the binding of CD40 ligand to cellular CD40. In another embodiment an agent which inhibits interaction may associate with CD40 or CD40 ligand in a manner which does not inhibit binding of CD40 ligand to cellular CD40, but which influences the cellular response to the CD40 ligation, such as by altering the turnover rate of the cellular CD40 or the CD40-agent complex, by altering binding kinetics of CD40 with CD40 ligand, or by altering the rate or extent of cellular activation in response to CD40 ligation.

In specific embodiments of this invention, the non-B cell, CD40-bearing cells are fibroblasts, endothelial cells, epithelial cells, T cells, basophils, macrophages, Reed-Steinberg cells, or dendritic cells. In a more specific embodiment the epithelial cells are keratinocytes. In another embodiment, the macrophages are foam cells (lipid-laden macrophages). Foam cells play a role in autoimmune diseases, for example rheumatoid arthritis and atherosclerosis.

In an embodiment of this invention the agent inhibits binding of CD40 ligand to CD40 on the cells.

In an embodiment of this method, the agent is a protein. In a more specific embodiment, the protein comprises an antibody or portion thereof, for example a Fab, F(ab')$_2$, complementarity determining region (CDR) light and/or heavy chain, antibody variable region light and/or heavy chain, or a portion thereof capable of specifically binding to CD40 ligand or CD40 ligand cell-surface receptor. The antibody can be a monoclonal or polyclonal antibody. In embodiments of this invention, the monoclonal antibody is a chimeric antibody, a humanized antibody, or a primatized antibody. In another embodiment the portion of the antibody comprises a single chain antibody. A single chain antibody is made up of variable regions linked by protein spacers in a single protein chain.

In an embodiment of the above-described method, the agent specifically binds to the antigen to which monoclonal antibody 5c8 specifically binds. In a specific embodiment, the agent is monoclonal antibody 5c8.

Monoclonal antibody 5c8 is produced by a hybridoma cell which was deposited on Nov. 14, 1991 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure. The hybridoma was accorded ATCC Accession Number HB 10916.

In another embodiment, the antibody specifically binds to CD40. One example of an anti-CD40 antibody is the monoclonal mouse anti-human CD40, available from Genzyme Customer Service (Product 80-3702-01, Cambridge, Mass.). In other embodiments the monoclonal antibody is a chimeric antibody, a primatized antibody, a humanized antibody, or an antibody which includes a CDR region from a first human and an antibody scaffold from a second human.

In one embodiment of this invention the protein is soluble, monomeric CD40-L protein, comprising all or part of the extracellular region of CD40-L, or variant thereof. The extracellular region of CD40-L contains the domain that binds to CD40. Thus, soluble CD40-L can inhibit the interaction between CD40L and the CD40-bearing cell. This invention contemplates that sCD40-L may constitute the entire extracellular region of CD40-L, or a fragment or derivative containing the domain that binds to CD40.

The meaning of "chimeric", "primatized" and "humanized" antibody and methods of producing them are well known to those of skill in the art. See, for example, PCT International Publication No. WO 90/07861, published Jul. 26, 1990 (Queen, et al.); and Queen, et al. *Proc. Nat'l Acad. Sci.-USA* (1989) 86: 10029). Methods of making primatized antibodies are disclosed, for example, in PCT International publication No. WO/02108, corresponding to International Application No. PCT/US92/06194 (Idec Pharmaceuticals); and in Newman, et al., *Biotechnology* (1992) 10:1455–1460, which are hereby incorporated by reference into this application.

Generally, a humanized antibody is an antibody comprising one or more complementarity determining regions (CDRs) of a non-human antibody functionally joined to human framework region segments. Additional residues associated with the non-human antibody can optionally be present. Typically, at least one heavy chain or one light chain comprises non-human CDRs. Typically, the non-human CDRs are mouse CDRs. Generally, a primatized antibody is an antibody comprising one or more complementarity determining regions (CDRs) of an antibody of a species other than a non-human primate, functionally joined to framework region segments of a non-human primate. Additional residues associated with the species from which the CDR is derived can optionally be present. Typically, at least one heavy chain or one light chain comprises CDRs of the species which is not a nonhuman primate. Typically, the CDRs are human CDRs. Generally, a chimeric antibody is an antibody whose light and/or heavy chains contain regions from different species. For example one or more variable (V) region segments of one species may be joined to one or more constant (C) region segments of another species. Typically, a chimeric antibody contains variable region segments of a mouse joined to human constant region segments, although other mammalian species may be used.

In another embodiment of this invention, the protein is soluble CD40 protein (sCD40), comprising the extracellular region of CD40, or portion thereof, or variant thereof. sCD40 inhibits the interaction between CD40L and CD40-bearing cells. sCD40 may be in monomeric or oligomeric form.

Variants can differ from naturally occurring CD40 or CD40 ligand in amino acid sequence or in ways that do not involve sequence, or both. Variants in amino acid sequence are produced when one or more amino acids in naturally occurring CD40 or CD40 ligand is substituted with a different natural amino acid, an amino acid derivative or non-native amino acid. Particularly preferred variants include naturally occurring CD40 or CD40 ligand, or biologically active fragments of naturally occurring CD40 or CD40 ligand, whose sequences differ from the wild type sequence by one or more conservative amino acid substitutions, which typically have minimal influence on the secondary structure and hydrophobic nature of the protein or peptide. Variants may also have sequences which differ by one or more non-conservative amino acid substitutions, deletions or insertions which do not abolish the CD40 or CD40 ligand biological activity. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from Table 4, and yet others are described by Dayhoff in the Atlas of Protein Sequence and Structure (1988).

TABLE 4

Conservative Amino Acid Replacements

| For Amino Acid | Code | Replace with any of |
|---|---|---|
| Alanine | A | D-Ala, Gly,beta-ALa, L-Cys,D-Cys |
| Arginine | R | D-Arg, Lys,homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3, 4 or 5-phenylproline, cis 3, 4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other variants within the invention are those with modifications which increase peptide stability. Such variants may contain, for example, one or more non-peptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D- instead of L-amino acids into the polypeptide may increase its resistance to proteases. See, e.g., U.S. Pat. No. 5,219,990.

The peptides of this invention may also be modified by various changes such as insertions, deletions and substitutions, either conservative or nonconservative where such changes might provide for certain advantages in their use.

In other embodiments, variants with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Variants within the scope of the invention include proteins and peptides with amino acid sequences having at least eighty percent homology with the extracellular region of CD40 or the extracellular region of CD40 ligand. More preferably the sequence homology is at least ninety percent, or at least ninety-five percent.

Just as it is possible to replace substituents of the scaffold, it is also possible to substitute functional groups which decorate the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring CD40 or CD40 ligand, as well as changes in acetylation, methylation, phosphorylation, carboxylation or glycosylation.

In a further embodiment the protein, including the extracellular region of CD40 ligand and CD40, is modified by chemical modifications in which activity is preserved. For example, the proteins may be amidated, sulfated, singly or multiply halogenated, alkylated, carboxylated, or phosphorylated. The protein may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of the protein, for example the methionine sulfone and methionine sulfoxide analogs. The invention also includes salts of the proteins, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

The soluble, monomeric CD40-L protein can comprise all or part of the extracellular region of CD40-L. The extracellular region of CD40-L contains the domain that binds to CD40. Thus, soluble CD40-L can inhibit the interaction between CD40L and the CD40-bearing cell. This invention contemplates that sCD40-L may constitute the entire extracellular region of CD40-L, or a fragment or derivative containing the domain that binds to CD40.

In another embodiment of this invention the protein comprising soluble extracellular region of CD40 or portion thereof further comprises an Fc region fused to the extracellular region of CD40 or portion thereof. In a specific embodiment the Fc region is capable of binding to protein A or protein G. In another embodiment the Fc region comprises IgG, $IgG_1$, $IgG_2$, $IgG_3$, $IgG_4$, IgA, $IgA_1$, $IgA_2$, IgM, IgD, or IgE.

In another embodiment of this invention, the sCD40 comprises CD40/Fc fusion protein. The fusion protein can be prepared using conventional techniques of enzymes cutting and ligation of fragments from desired sequences. Suitable Fc regions for the fusion protein are Fc regions that can bind to protein A or protein G, or that are capable of recognition by an antibody that can be used in purification or detection of a fusion protein comprising the Fc region. For example, the Fc region may include the Fc region of human $IgG_1$ or murine $IgG_1$. This invention also provides a nucleic acid molecule which encodes the CD40/Fc fusion protein.

The method of creating soluble forms of membrane molecules by recombinant means, in which sequences encoding the transmembrane and cytoplasmic domains are deleted, is well known. See generally Hammonds et al., U.S. Pat. No. 5,057,417. In addition, methods of preparing sCD40 and CD40/Fc fusion protein are well-known. See, e.g., PCT International Publication No. WO 93/08207; Fanslow et al., "Soluble Forms of CD40 Inhibit Biologic Responses of Human B Cells, "*J. Immunol.*, vol. 149, pp.655–60 (July 1992).

In an embodiment of this invention, the agent is a small molecule. As used herein a small molecule is a compound having a molecular weight between 20 Da and $1 \times 10^6$ Da, preferably from 50 Da to 2 kDa.

In an embodiment of this invention, the agent is selected by a screening method.

In a specific embodiment the small molecule or other agent is selected by a screening method which comprises, isolating a cell sample, for example a sample of a biological fluid (e.g., blood) from an animal; culturing the sample under conditions permitting activation of CD40-bearing cells contained therein; contacting the sample with an amount of cells expressing a protein which is specifically recognized by monoclonal antibody 5c8 produced by the hybridoma having ATCC Accession no. HB 10916, or with a protein which is specifically recognized by monoclonal antibody 5c8 produced by the hybridoma having ATCC Accession no. HB 10916, effective to activate the CD40-bearing cells; contacting the sample with an amount of a small molecule (or other pharmaceutical compound or agent) effective to inhibit activation of the CD40-bearing cells if the small molecule is capable of inhibiting activation of the CD40-bearing cells; and determining whether the cells expressing the protein which is specifically recognized by monoclonal antibody 5c8 produced by the hybridoma having ATCC Accession no. HB 10916, or with the protein which is specifically recognized by monoclonal antibody 5c8 produced by the hybridoma having ATCC Accession no. HB 10916 activate the CD40-bearing cells in the presence of the small molecule (or other pharmaceutical compound or agent). The cell sample may be isolated from diverse tissues, including cell lines in culture or cells isolated from an animal, such as dispersed cells from a solid tissue, cells derived from a bone marrow biopsy, or cells isolated from a body fluid such as blood or lymphatic fluid.

In another specific embodiment the agent (molecule) is selected based on a three-dimensional structure of soluble extracellular region of CD40 ligand or portion thereof capable of inhibiting interaction between CD40 ligand and CD40 on the cells. The agent may be selected from a library of known agents, modified from a known agent based on the three-dimensional structure, or designed and synthesized de novo based on the three-dimensional structure. In specific embodiments the agent (molecule) is designed by structure optimization of a lead inhibitory agent based on a three-dimensional structure of a complex of the soluble extracellular region of CD40 ligand or portion thereof with the lead inhibitory agent. A lead inhibitory agent is a molecule which has been identified which, when it is contacted with CD40 ligand or portion thereof, binds to and complexes with the soluble extracellular region of CD40 ligand, CD40, or portion thereof, thereby decreasing the ability of the complexed or bound CD40 ligand or CD40 ligand portion to activate CD40-bearing cells. In another embodiment, a lead inhibitory agent may act by interacting with either the extracellular region of CD40 ligand, CD40, or in a tertiary complex with both a portion of CD40 ligand and CD40, decreasing the ability of the complexed CD40 ligand-CD40 to activate the CD40-bearing cells. In the methods of the invention, the CD40 ligand may be either soluble or bound to cells such as activated T cells, and may be either full length native CD40 ligand or portions thereof. Decreased ability to activate CD40-bearing cells may be measured in different ways. One way it may be measured is by showing that CD40 ligand, in the presence of inhibitor, causes a lesser degree of activation of CD40-bearing cells, as compared to treatment of the cells with a similar amount of CD46 ligand without inhibitor under similar conditions. Decreased ability to activate CD40-bearing cells may also be indicated by a higher concentration of inhibitor-CD40 ligand complex being required to produce a similar degree of activation of CD40-bearing cells under similar conditions, as compared to unbound CD40 ligand. At the extreme, the inhibitor-contacted CD40 ligand may be unable to activate CD40-bearing cells at concentrations and under conditions which allow activation of these cells by unbound CD40 ligand or a given portion thereof.

The agent (small molecule) can be selected by a computational screening method using the crystal structure of a soluble fragment of the extracellular domain of human CD40L containing residues Gly 116-Leu261 of SEQ ID NO:1 (sCD40L(116–261)).

The crystal structure to be used with the screening method can be determined at 2 Å resolution by the method of molecular replacement. In brief, a soluble fragment of the extracellular domain of human CD40 ligand containing amino acid residues Gly 116 to the C-terminal residue Leu 261 are first produced in soluble form, then purified and crystallized. The crystals can be tested for diffraction capacity on the X-ray beam of an Elliot GX-13 generator. Molecular replacement and refinement can be done with the XPLOR program package and QUANTA (Molecular Simulations, Inc.) Software. In particular, a 3-dimensional model of human sCD40L can be constructed using the murine CD40L model using QUANTA protein homology modeling software. This model can then be used as a probe for molecular replacement calculations and refined using XPLOR. This method of determining the crystal structure of sCD40L is described in more detail in Karpusas et al., "2 Å crystal structure of an extracellular fragment of human CD40 ligand," *Structure* (October 1995) 3(10):1031–1039. The atomic coordinates of sCD40L(116–261) are provided in FIGS. 17A–Y. The screening method for selecting an agent includes computational drug design and iterative structure optimization, as described below.

The agent may be a small molecule inhibitor selected using computational drug design. Using this method, the sCD40L crystal structure coordinates are used as an input for a computer program, such as DOCK, which outputs a list of small molecule structures that are expected to bind to CD40L. Use of such computer programs are well-known. See, e.g., Kuntz, "Structure-Based Strategies for drug design and discovery," *Science*, vol. 257, p. 1078 (1992). The list of small molecule structures can then be screened by biochemical assays for CD40L binding. Competition-type biochemical assays, which are well known, can be used. See, e.g., Bajorath et al., "Identification of residues of CD40 and its ligand which are critical for the receptor-ligand interaction," *Biochemistry*, 34, p. 1833 (1995). The structures that are found to bind to CD40L can thus be used as agents for the present invention. The agent may also be a modified small molecule, determined by interactive cycles of structure optimization. Using this approach, a small molecule inhibitor of CD40L found using the above computational approach or other approach can be co-crystallized with sCD40L and the crystal structure of the complex solved by molecular replacement. The information revealed through molecular replacement can be used to optimize the structure of the small molecule inhibitors by clarifying how the molecules interact with CD40L. The small molecule may be modified to improve its physiochemical properties, including specificity and affinity for CD40L.

In an embodiment of this invention the agent specifically binds to CD40 on the cell surface. In a specific embodiment the agent is a protein, for example an antibody or the extracellular region of CD40 ligand. The antibody may be a polyclonal or monoclonal antibody. It is preferred that the monoclonal antibody be chimeric or humanized. It may also be primatized.

In Vivo Use

This invention provides a method of inhibiting activation by CD40 ligand of cells bearing CD40 on the cell surface, in a subject, comprising administering to the subject an agent capable of inhibiting interaction between CD40 ligand and the cells, in an amount effective to inhibit activation of the cells in the subject. In one embodiment, the cells bearing CD40 on the cell surface are cells other than B cells. In another embodiment, they are plasma cells, including differentiated plasma cells such as myeloma cells.

In specific embodiments of this invention, the non-B cell, CD40-bearing cells are fibroblasts, endothelial cells, epithelial cells, T cells, basophils, macrophages, Reed-Steinberg cells, or dendritic cells. In a more specific embodiment the epithelial cells are keratinocytes. In another embodiment, the macrophages are foam cells (lipid-laden macrophages). Foam cells play a role in autoimmune diseases, for example rheumatoid arthritis and atherosclerosis.

In an embodiment of this method, the agent is a protein.

In a more specific embodiment, the protein comprises an antibody or portion thereof, for example a Fab, F(ab')$_2$, complementarity determining region (CDR) light and/or heavy chain, antibody variable region light and/or heavy chain, or a portion thereof capable of specifically binding to CD40 ligand or CD40 ligand cell-surface receptor, or to CD40. One example of an anti-CD40 antibody is the monoclonal mouse anti-human CD40, available from Genzyme Customer Service (Product 80-3702-01, Cambridge, Mass.). The antibody can be a monoclonal or polyclonal antibody. In embodiments of this invention, the monoclonal antibody is a chimeric antibody, a humanized antibody, or a primatized antibody. In another embodiment the portion of the antibody comprises a single chain antibody. A single chain antibody is made up of variable regions linked by protein spacers in a single protein chain.

In an embodiment of the above-described method, the agent specifically binds to the antigen to which monoclonal antibody 5c8 (ATCC Accession No. HB 10916) specifically binds. In a specific embodiment, the agent is monoclonal antibody 5c8 (ATCC Accession No. HB 10916).

The compounds of this invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, topical, or inhaled. Sustained release administration is also specifically included in the invention, by such means as depot injections of erodible implants directly applied during surgery.

The compounds are administered at any dose per body weight and any dosage frequency which is medically acceptable. For example, acceptable dosage for the compound of this invention (especially for the antibody or antibody portion of this invention) includes a range of between about 0.01 and 200 mg/kg subject body weight. A dosage range is between about 0.1 and 50 mg/kg. In a still more specific embodiment the dose is between about 1 and 30 mg/kg. The dosage is repeated at intervals ranging from each day to every other month. One dosing regimen is to administer a compound of the invention daily for the first three days of treatment, after which the compound is administered every 3 weeks, with each administration being intravenously at 5 or 10 mg/kg body weight.

Another regime is to administer a compound of the invention daily intravenously at 5 mg/kg body weight for the first three days of treatment, after which the compound is administered subcutaneously or intramuscularly every week at 10 mg per subject. Another regime is to administer a single dose of the compound of the invention parenterally at 20 mg/kg body weight, followed by administration of the compound subcutaneously or intramuscularly every week at 10 mg per subject.

The compounds of the invention may be administered as a single dosage for certain indications such as preventing immune response to an antigen to which a subject is exposed for a brief time, such as an exogenous antigen administered on a single day of treatment. Examples of such an antigen would include coadministration of a compound of the invention along with a gene therapy vector, or a therapeutic agent such as an antigenic pharmaceutical or a blood product. In indications where antigen is chronically present, such as in controlling immune reaction to transplanted tissue or to chronically administered antigenic pharmaceuticals, the compounds of the invention are administered at intervals for as long a time as medically indicated, ranging from days or weeks to the life of the subject.

This invention provides a method of inhibiting an inflammatory response in a subject, comprising the above-described method of inhibiting activation by CD40 ligand of cells, other than B cells, bearing CD40 on the cell surface (e.g., fibroblast cells, endothelial cells, or keratinocyte cells) in a subject. Inflammatory responses are characterized by redness, swelling, heat and pain, as consequences of capillary dilation with edema and migration of phagocytic leukocytes. Inflammation is further defined by Gallin (Chapter 26, Fundamental Immunology, 2d ed., Raven Press, New York, 1989, pp. 721–733), which is hereby incorporated by reference.

This method is effective in inhibiting activation of any fibroblasts. In particular embodiments, the fibroblasts are synovial membrane fibroblasts, dermal fibroblasts, pulmonary fibroblasts, or liver fibroblasts. In particular embodiments, the condition dependent on CD40 ligand-induced activation of fibroblast cells is selected from the group consisting of arthritis, scleroderma, and fibrosis (e.g. fibrotic diseases of the liver and lung). In an embodiment of this invention, the fibrotic disease of the lung is caused by rheumatoid arthritis or scleroderma.

In an embodiment of this invention the arthritis is rheumatoid arthritis, non-rheumatoid inflammatory arthritis, arthritis associated with Lyme disease, or osteoarthritis. In another specific embodiment, the fibrosis is pulmonary fibrosis, hypersensitivity pulmonary fibrosis, or pneumoconiosis. In another specific embodiment, the fibrotic disease of the liver is Hepatitis-C, Hepatitis-B, Hepatitis non-B non-C, cirrhosis, or cirrhosis of the liver secondary to a toxic insult, drugs, a viral infection, or an autoimmune disease. Alcohol consumption is one example of toxic insult which can cause cirrhosis of the liver. One example of a drug that can cause cirrhosis of the liver is Bleomycin. Others are known in the art.

Examples of viral infections which can cause fibrotic disease of the liver include, among others known to the art, Hepatitis B, Hepatitis C, and Hepatitis non-B non-C. Examples of autoimmune diseases which can cause fibrotic disease of the liver include, among others known to the art, primary biliary cirrhosis, and Lupoid hepatitis (autoimmune hepatitis). In specific embodiments the pulmonary fibrosis is pulmonary fibrosis secondary to adult respiratory distress syndrome (ARDS), drug-induced pulmonary fibrosis, idiopathic pulmonary fibrosis, or hypersensitivity pneumonitis; the pneumoconiosis is asbestosis, siliconsis, or Farmer's lung as well as other pneumoconioses that are known in the art to which this invention pertains.

This invention provides a method of treating a condition dependent on CD40 ligand-induced activation of endothelial cells in a subject, comprising the above-described method of inhibiting activation of endothelial cells by CD40 ligand in a subject.

In embodiments of this invention the condition dependent on CD40 ligand-induced activation of endothelial cells is selected from the group consisting of atherosclerosis, reperfusion injury, allograft rejection, organ rejection, and chronic inflammatory autoimmune diseases.

In a specific embodiment the atherosclerosis is accelerated atherosclerosis associated with organ transplantation. In situ CD40 and CD40L expression in accelerated atherosclerosis associated with transplant rejection have been studied. Frozen sections of coronary arteries from 4 heart transplant patients that required retransplantation due to accelerated atherosclerosis were analyzed by routine immunohistochemistry utilizing anti-CD40 mAb G28.5, anti-CD40L mAb 5C8 or control mAbs. Routine H & E staining revealed the typical intimal hyperplasia, smooth muscle cell proliferation, and inflammatory cell infiltration associated with the disease. CD40 was widely expressed in the lesions: endothelial cells, foam cells and infiltrating inflammatory cells all express CD40. CD40L immunoreactivity was observed as discrete, faint staining of infiltrating mononuclear cells, presumably CD4+ T cells. Together, these studies demonstrate the presence of CD40L+ mononuclear cells and CD40+ endothelial cells, foam cells, and inflammatory cells in situ in lesions of accelerated atherosclerosis associated with transplantation.

In another specific embodiment the chronic inflammatory autoimmune disease is vasculitis, rheumatoid arthritis, scleroderma, or multiple sclerosis.

This invention provides a method of treating a condition dependent on CD40 ligand-induced activation of keratinocytes in a subject, comprising the above-described method of inhibiting activation of keratinocyte cells by CD40 ligand in a subject.

In a specific embodiment the condition dependent on CD40 ligand-induced activation of keratinocytes is psoriasis.

This invention provides a method of treating a condition dependent on CD40 ligand-induced activation of macrophages in a subject, comprising the above-described method of inhibiting activation of macrophages by CD40 ligand in a subject. In specific embodiments, the condition dependent on CD40 ligand-induced activation of macrophages is atherosclerosis or rheumatoid arthritis.

The subject which can be treated by the above-described methods is an animal. Preferably the animal is a mammal. Examples of mammals which may be treated include, but are not limited to, humans; rodents such as the murine animals rats and mice, as well as rabbits, and guinea pig; cow; horse; sheep; goat; pig; dog and cat.

This invention also provides a method of treating a condition dependent on CD40 ligand-induced activation of plasma cells in a subject (including malignant plasma cells), comprising administering to the subject an agent capable of inhibiting interaction between CD40 ligand and the cells, in an amount effective to inhibit activation of the cells in the subject. Plasma cells are differentiated B cells. In a specific embodiment the condition is multiple myeloma.

This invention provides a method of promoting the growth of cells bearing CD40 on the cell, comprising contacting the cells with an amount of CD40 ligand effective to promote growth of the cells. In an embodiment the cells are cells bearing CD40 on the cell surface o other than B cells. In specific embodiments the non-B cells bearing CD40 on the cell surface are endothelial cells, fibroblasts, epithelial cells, T cells, or basophils. In another embodiment the cells are plasma cells, including differentiated plasma cells such as myeloma cells.

This invention further provides a pharmaceutical composition comprising a therapeutically effective amount of the agent described herein c capable of inhibiting interaction between CD40 ligand and cells bearing CD40 on the cell surface, and a pharmaceutically acceptable carrier.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

Materials and Methods

Patients Studied

All RA patients studied met the American College of Rheumatology criteria for RA (19). The diagnosis of OA was established by the patients' physicians utilizing clinical and radiographic criteria. One patient with chronic inflammatory arthritis (IA) of unknown etiology was also studied.

Monoclonal Antibodies and T Cell Lines

The IgG2a murine anti-CD40L mAb (5C8) was previously generated (3). Hybridomas anti-MHC Class I (W6/32), anti-MHC Class II (L243), anti-CD14 (3C10), anti-CD40 (G28.5) and anti-CD45 (GAP 8.3) were purchased from American Type Culture Collection (ATCC) (Rockville, Md.). Hybridoma ascites was purified on a Protein G column (Pharmacia, Piscataway, N.J.). Anti-CD3 and anti-CD54 mAbs were purchased from Biosource International (Camarillo, Calif.). Anti-CD106 mAb was kindly provided by Biogen (Cambridge, Mass.) and biotinylated as previously described (20). Isotype control mAbs utilized for FACS analysis were purchased from Becton-Dickinson (San Jose, Calif.) or Caltag (South San Francisco, Calif.). P1.17 is a control IgG2a murine mAb obtained from Biogen and utilized for functional studies.

D1.1 is a Jurkat T cell subclone that constitutively expresses CD40L (3, 21). B2.7 is a CD40L$^-$ Jurkat subclone (3, 21). CD40L$^+$ Jurkat B2.7 transfectants expressing full length CD40L protein were generated as previously reported (20).

Isolation of Fibroblasts

Synovial membrane was obtained from 6 RA or 8 OA patients undergoing joint replacement surgery. SM from one patient with IA was collected at arthroscopy. SM was cut into small pieces and cultured in 100 mm tissue culture petri dishes (Corning, Corning, N.Y.) or 25 cm$^2$ flasks (Costar, Cambridge, Mass.) with Isocove's Modified Dulbecco's Media (Gibco, Grand Island, N.Y.) supplemented with 10% FCS (Summit Biotechnology, Ft. Collins, Colo.) and 1% penicillin-streptomycin (Sigma, St. Louis, Mo.) (10% FM). Synoviocytes were allowed to adhere for several days at which time tissue debris and non-adherent cells were removed. Synoviocytes were grown to confluence and passaged by treatment with 1% trypsin-EDTA (Sigma). Synoviocytes were studied between 1–6 passages in vitro. A normal dermal fibroblast line frozen following the second passage (CCD 965SK) was purchased from ATCC. Dermal fibroblast lines were studied between 2–4 passages.

Studies on the Effects of Cytokines on Fibroblast CD40 Expression

To study the effects of cytokines on fibroblast CD40 expression, cells were cultured in 6 well plates (Nunc, Denmark) and grown to near confluence. The media was aspirated and fibroblasts then cultured with the indicated concentrations of rINF-$\gamma$ (Biogen), rIL-1$\alpha$ (R & D, Minneapolis, Minn.), rTNF-$\alpha$ (Upstate Biotechnology, Lake Placid, N.Y.), rIL-4 (Biosource International), rGM-CSF (Immunex, Seattle, Wash.) or combinations of cytokines in 3 ml of 10% FM. At the indicated time points, the media was aspirated, the cells washed once with saline and 1 ml of 1% trypsin-EDTA added to the wells. After 7 minutes cold 10% FM was added to the wells and the cells collected for FACS analysis.

Studies on Functional Consequences of Fibroblast CD40 Ligation.

To determine the effect of CD40 ligation on the expression of fibroblast cell surface molecules, fibroblasts were cultured in 6 well plates as described above. When the fibroblasts were near confluence 1×10$^6$ CD40L$^+$ Jurkat D1.1 cells, CD40L$^-$ Jurkat B2.7 cells or CD40L$^+$ Jurkat B2.7 transfectants were added to the culture. Where indicated, D1.1 cells were pretreated with anti-CD40L mAb 5C8 (10 $\mu$g/ml) or isotype control mAb P1.17 (10 $\mu$g/ml) prior to the addition to fibroblasts. After 24 hours the cells were collected by trypsinization and two-color FACS analyses performed.

For studies determining the effect of CD40 ligation on fibroblast proliferation, approximately 5×10$^3$ cells were added to flat bottom 96 well plates (Nunc) in 10% FM. After 18 hours the media was changed to 1% FM and rINF-$\gamma$ 1000 U/ml added to the indicated cells. After an additional 18 hours, 1×10$^5$ mitomycin-C (Sigma) treated CD40L$^+$ Jurkat B2.7 transfectants or CD40L Jurkat B2.7 cells in 1% FM were added to the fibroblasts. Anti-CD40L mAb 5C8 (5 $\mu$g/ml) or control mAb P1.17 (5 $\mu$g/ml) were also added to some wells as indicated. 10% FM was added to some cells as a control for the induction of SM fibroblast proliferation. Cultures were maintained for an additional 48 hours and pulsed with 1 $\mu$Ci $^3$H thymidine for the last 18 hours of the experiment. Following trypsinization, $^3$thymidine incorporation was determined by harvesting onto glass fiber filter strips (Cambridge Technologies, Watertown, Mass.) and scintillation counting (BetaCounter, Pharmacia).

To determine the effect of CD40 ligation on IL-6 production, a bioassay utilizing the IL-6 responsive murine B cell line B9 was performed (22). Equal numbers of fibroblasts in 10% FM were seeded in 96 well plates as mentioned above. After adhering overnight, 1×10$^5$ mitocycin-C treated CD40L$^+$ Jurkat D1.1 cells, CD40L Jurkat B2.7 cells or CD40L$^+$ Jurkat B2.7 transfectants were added to the fibroblasts. Where indicated, D1.1 cells were pretreated with anti-CD40L mAb 5C8 (10 $\mu$g/ml) or control mAb P1.17 (10 $\mu$/ml). Control wells consisted of Jurkat cells cultured alone. After 48 hours, serial dilutions of fibroblast or control supernatants or rIL-6 were added to 7.5×10³ B9 cells in 96 well plates. B9 cells were maintained in culture for 96 hours, pulsed with 1 µCi ³H thymidine for the last 18 hours and harvested as mentioned above.

Cytofluorographic Analysis

The methods utilized for cytofluorographic analysis have been previously described (21). In all experiments the cells were first treated with aggregated human immunoglobulin (Enzyme International, Fallbrook, Calif.) to block non-specific Ig binding. For single-color FACS analysis, cells were stained with saturating concentrations of primary antibody for 30–60 minutes at 4° C. Following washing, FITC conjugated F(ab)$_2$ goat anti-mouse IgG (Cappel, Cochranville, Pa.) was added for 30–60 minutes at 4° C. The cells were washed and fixed with 1% formaldehyde prior to FACS analysis. For two-color FACS analysis, cells were simultaneously stained with the indicated FITC or PE conjugated mAbs for 30–60 minutes at 4° C. Fluorescence intensity was measured on a FACScan cytofluorograph with the Consort-30 software (Becton-Dickinson, Mountainview, Calif.). Mean fluorescence intensity (MFI) refers to values normalized to the log scale as calculated by Becton-Dickinson C30 software.

Results

Expression of CD40 on Cultured SM or Dermal Fibroblasts.

To determine whether SM fibroblasts express CD40, SM derived from 6 RA, 1 IA, or 8 OA patients was first minced and placed in culture after which non-adherent cells were discarded. As expected, primary cultures of adherent cells were pleiomorphic with regard to morphology and phenotype. A minority of cells assumed a stellate morphology or a rounded appearance characteristic of macrophages. However, the majority of cells in primary culture had fibroblast-like morphology and phenotype, i.e., CD45$^-$ CD14$^-$MHC Class II$^-$(FIG. 1). Virtually all cells had fibroblast-like morphology and phenotype following 2–3 passages in vitro.

Five RA fibroblast lines were studied for CD40 expression following the first or second passage in vitro and were CD40$^+$ by FACS analysis (FIG. 1). An IA fibroblast line similarly expresses CD40 (table 1). One RA fibroblast line had been in culture for 2 months prior to analysis and was CD40$^-$(data not shown). Eight OA fibroblast lines were studied for CD40 expression following the first or second passage in vitro and all were CD40$^+$ (FIG. 1). To determine if fibroblast CD40 expression was restricted to SM fibroblasts, normal dermal fibroblasts were analyzed for CD40 expression following 2–4 passages in vitro. To variable degrees, all 3 dermal fibroblast lines studied also express cell surface CD40 molecules (FIG. 2). However, CD40 expression on synovial membrane or dermal fibroblasts decreased with increasing time in culture such that some fibroblast lines became CD40$^-$ after 3–4 passages (data not shown). These studies demonstrate that dermal fibroblasts or SM fibroblasts isolated from patients with various arthritides can express CD40 in vitro.

Effect of Cytokines on Fibroblast CD40 Expression

Interferon-γ (INF-γ) is known to upregulate CD40 expression on B cells (23), macrophages (12) and thymic epithelial cells (15). Moreover, IL-1α or TNF-α upregulates CD40 expression on thymic epithelial cells (15). Therefore, it was next asked if rINF-γ, rIL-1α or rTNF-α regulates CD40 expression on cultured SM fibroblasts. Cells were cultured with the indicated cytokines and CD40 expression determined by FACS analysis. As a control for the effects of these cytokines on the expression of SM fibroblast cell surface molecules, CD54 (ICAM-1) expression was also determined (24). rINF-γ upregulates SM fibroblast CD40 expression (table 1 and FIG. 3). In contrast, rIL-1α and rTNF-α have minimal effect on SM fibroblast CD40 expression (table 1 and FIG. 3). However, either rIL-1α or rTNF-α augment the effect of rINF-γ on SM fibroblast CD40 expression (FIG. 3). rINF-γ also induces CD40 expression on SM fibroblasts that had lost CD40 expression during serial passages in culture (data not shown). Moreover, rINF-γ upregulates CD40 expression on dermal fibroblasts (FIG. 2). rIL-4 or rGM-CSF upregulate CD40 expression on B cells (25) or monocytes (12), respectively. However, rIL-4 or rGM-CSF have no effect on SM fibroblast CD40 expression (data not shown). Together, these studies demonstrate that rINF-γ induces and upregulates fibroblast CD40 expression and the addition of rIL-1α or rTNF-α augments this effect.

Figure 5:
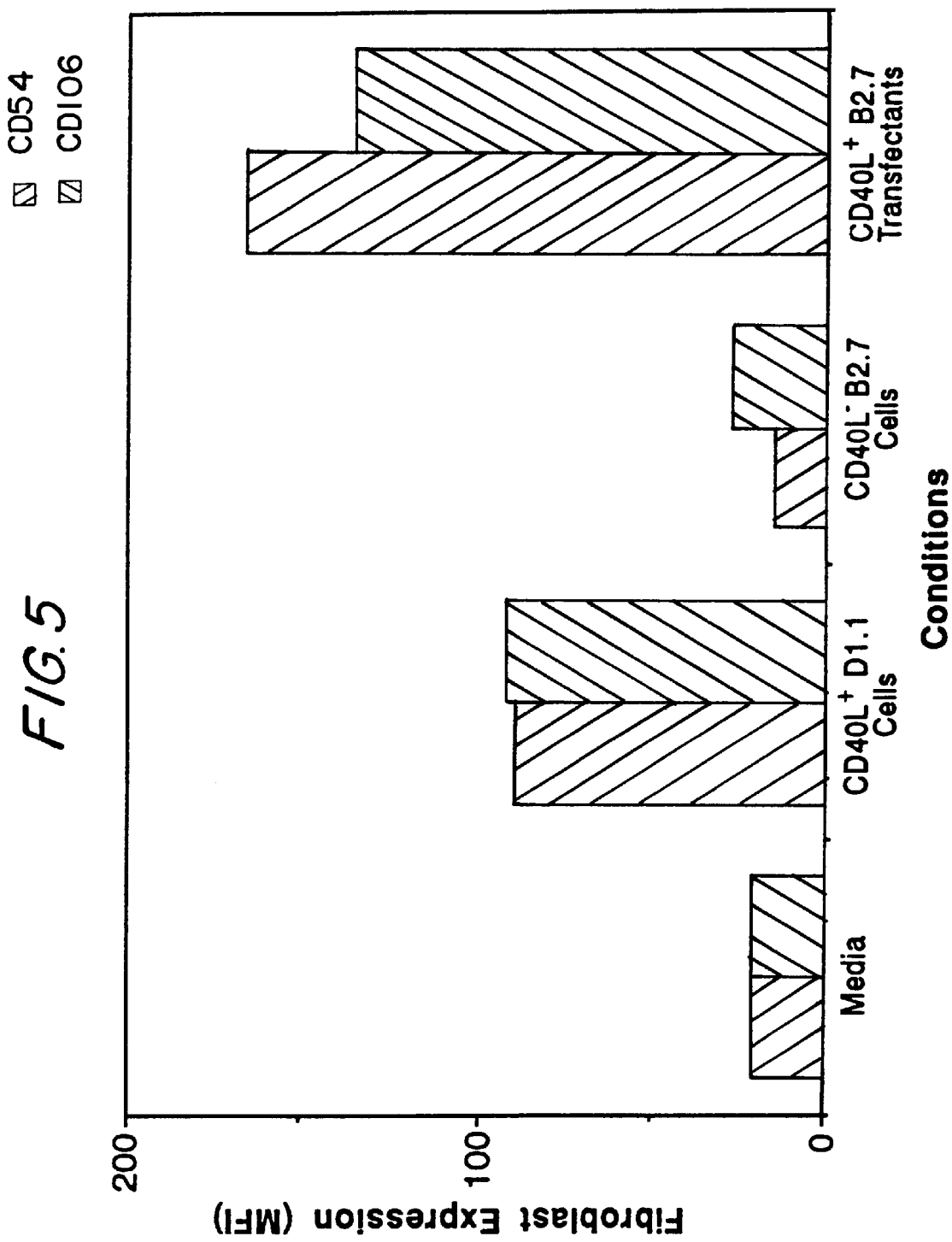
FIG. 5. Transfection of CD40L confers the capacity to upregulate SM fibroblast CD54 (ICAM-1) and CD106 (VCAM-1) expression. Shown are bar graphs indicating CD54 or CD106 MFI on SM fibroblasts following culture for 24 hours with media, CD40L⁺ D1.1 cells, CD40L⁻ B2.7 cells or CD40L⁺ B2.7 transfectants, as indicated. CD54 and CD106 expression were determined by two-color FACS analysis as in FIG. 4. The background MFI of an isotype control mAb is subtracted from each value. The experiment shown is representative of 2 similar experiments performed.

Effect of CD40L-CD40 Interactions on SM Fibroblast CD54 (ICAM-1) and CD106 (VCAM-1) Expression Because CD40 triggering is known to upregulate a variety of cell surface molecules on B cells, including adhesion molecules (26), it was determined if CD40 ligation upregulates CD54 or CD106 expression on SM fibroblasts. SM fibroblasts were cultured with CD40L$^+$ Jurkat D1.1 cells in the presence or absence of anti-CD40L mAb 5C8 or control mAb. SM fibroblasts were also cultured with CD40L$^+$ Jurkat B2.7 cells or CD40L$^+$ Jurkat B2.7 transfectants. After the indicated period of time in culture, SM fibroblast CD54 or CD106 expression was determined by two-color FACS analysis. CD13 expression was utilized to discriminate SM fibroblasts from Jurkat T cells (27). CD40L$^+$ D1.1 cells, but not control CD40L$^-$ B2.7 cells, induce a 2–4 fold increase in SM fibroblast CD54 expression (FIGS. 4 and 5) in a manner that is specifically inhibited by mAb 5C8 but not by control mAb (FIG. 4). Moreover, CD40L$^+$ D1.1 and CD40L$^+$ Jurkat B2.7 transfectants, but not control CD40L$^-$ B2.7 cells, similarly upregulate SM fibroblast CD106 expression (FIG. 5). Together, these results demonstrate that CD40L-CD40 interactions upregulate SM fibroblast CD54 and CD106 expression.

Effect of CD40 ligation on SM fibroblast IL-6 secretion.

Figure 6B:
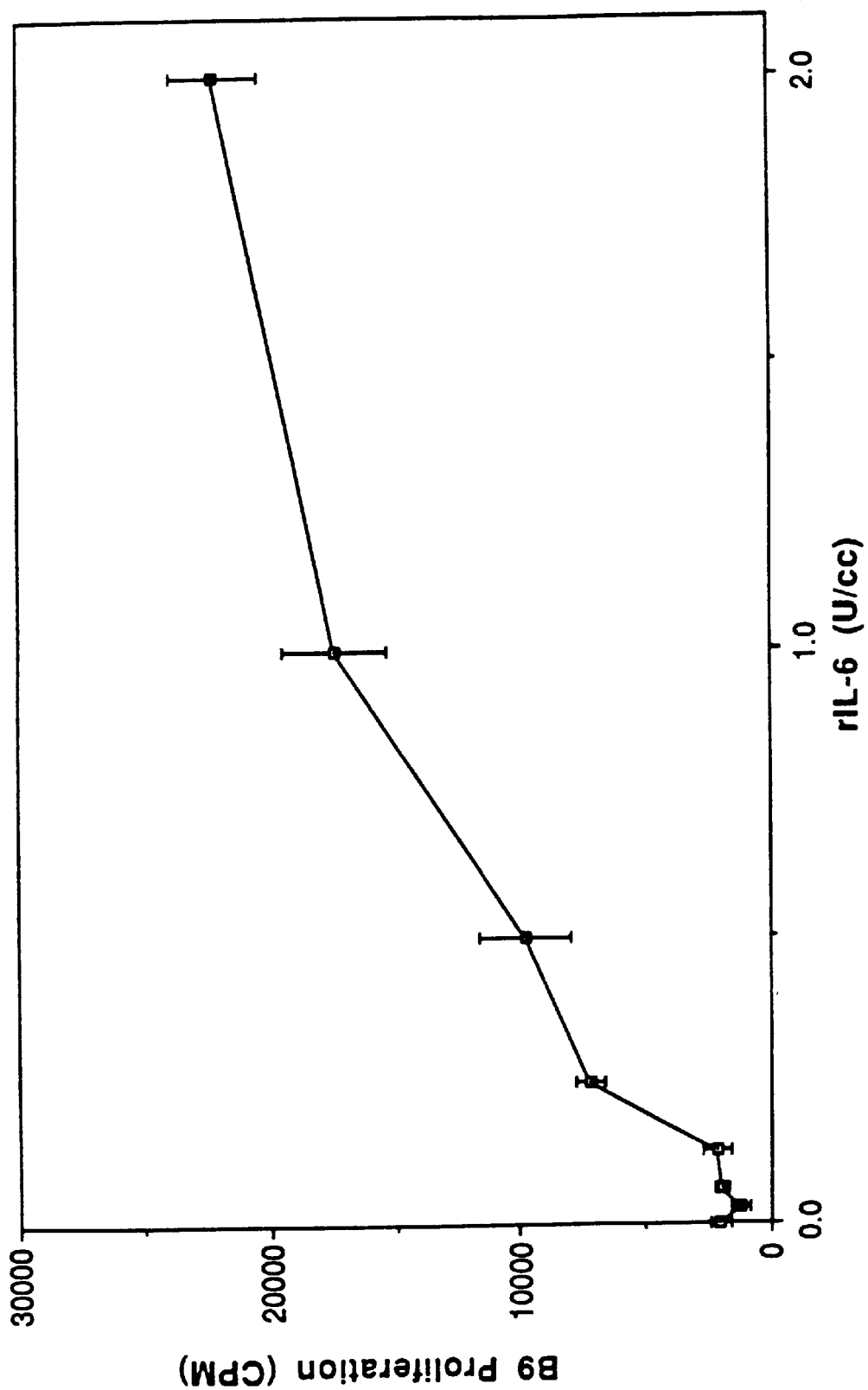
FIG. 6B. B9 proliferation in response to rIL-6. In a parallel experiment to that shown in FIG. 6A, B9 cells were cultured with varying concentrations of rIL-6.

Ligation of CD40 induces B cells (28) and monocytes (12) to produce IL-6. Interestingly, SM fibroblasts produce IL-6 in vivo (29, 30) and in vitro (31). The next series of experiments asked if CD40L-CD40 interactions effect IL-6 secretion by SM fibroblasts. Therefore, SM fibroblasts were cultured with mitomycin-C treated CD40L$^+$ Jurkat D1.1 cells in the presence or absence of anti-CD40L mAb 5C8 or control mAb. Additionally, SM fibroblasts were cultured with CD40L$^-$ Jurkat B2.7 cells or CD40L$^+$ Jurkat B2.7 transfectants. Fibroblast supernatants or control supernatants from Jurkat cells cultured alone were collected after 48 hours and dilutions added to the IL-6 responsive murine B cell line B9. D1.1 cells and CD40L B2.7 transfectants, but not CD40L B2.7 cells, augment SM fibroblast IL-6 secretion (FIG. 6). Additionally, anti-CD40L mAb 5C8, but not control mAb, inhibits this effect of D1.1 cells. Control supernatants collected from Jurkat cells cultured alone did not induce B9 proliferation (See description of FIG. 6). These studies indicate that ligation of CD40 on SM fibroblasts augments IL-6 secretion.

Effect of CD40L-CD40 interactions on SM fibroblast proliferation

Figure 8:
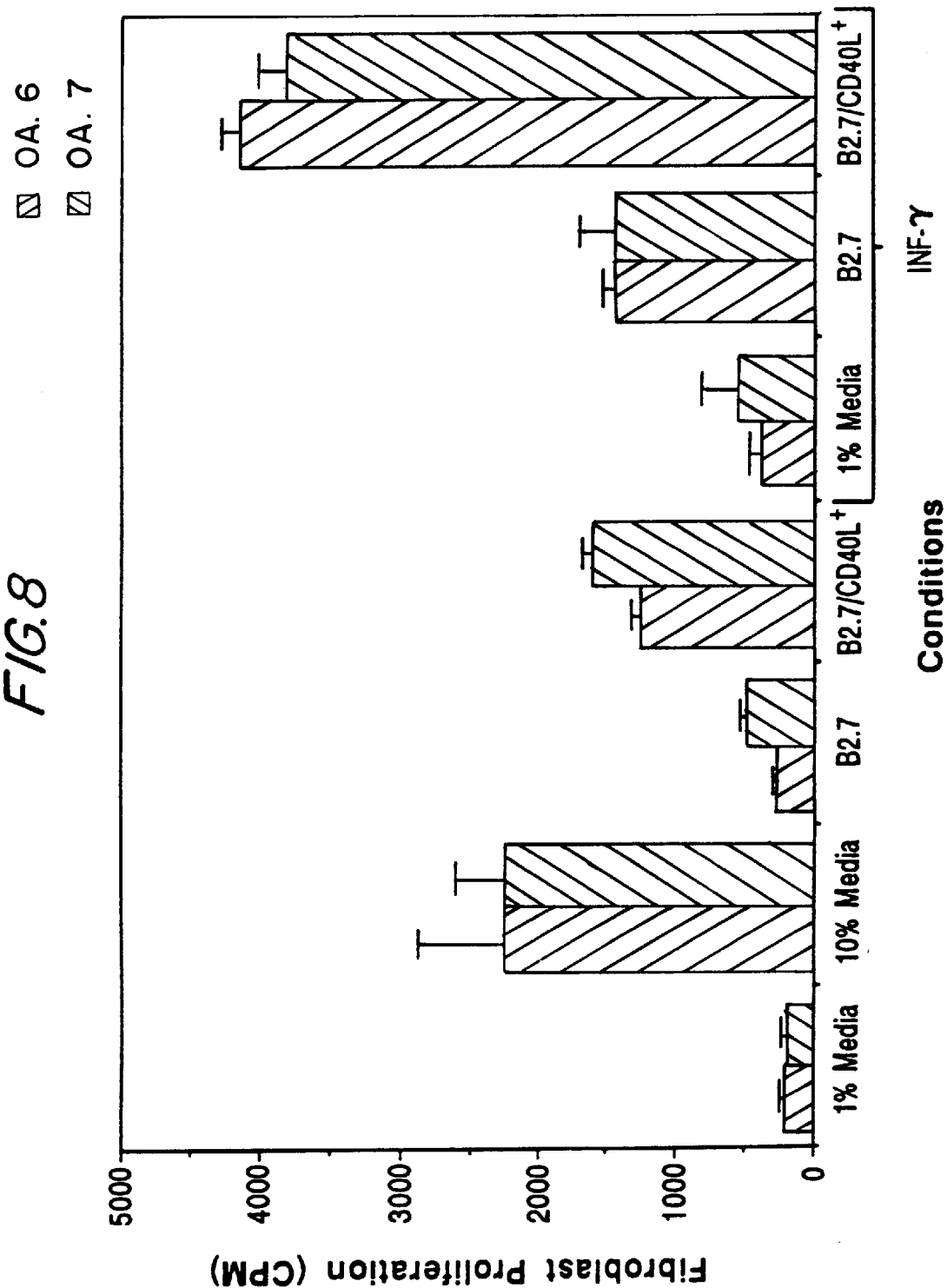
FIG. 8. Effect of rINF-γ on CD40L mediated SM fibroblast proliferation. Shown are bar graphs demonstrating SM fibroblast $^3$H-thymidine incorporation following coculture in 1% FM with mitomycin-C treated CD40L⁻ Jurkat B2.7 cells or CD40L⁺ Jurkat B2.7 transfectants for 48 hours. Where indicated, SM fibroblasts were pretreated for 18 hours with rINF-γ (1000 U/ml) prior to the addition of mitomycin-C treated CD40L⁻ B2.7 cells or CD40L⁺ B2.7 transfectants. SM fibroblast proliferation was determined as outlined in Materials and Methods for First Series of Experiments. Background proliferation of CD40L⁻ Jurkat B2.7 cells and CD40L⁺ Jurkat B2.7 transfectants was 185±66 cpm and 65±5 cpm, respectively. Background proliferation is subtracted in coculture experiments. Also shown are the proliferative responses of fibroblasts following culture in 1% FM or 10% FM. Similar results were obtained in 2 additional experiments. Error bars show observed error.
Figure 9A:
FIGS. 9A–D. Endothelial cells in skin express CD40 in situ. Shown are immunohistologic studies of frozen sections demonstrating the expression of: (a) CD40, skin (magnification 40×), (b) CD34, skin (magnification 40×), (c) CD21, skin (magnification 40×) and (d) control mouse (magnification 40×).
Figure 9B:
Figure 9C:
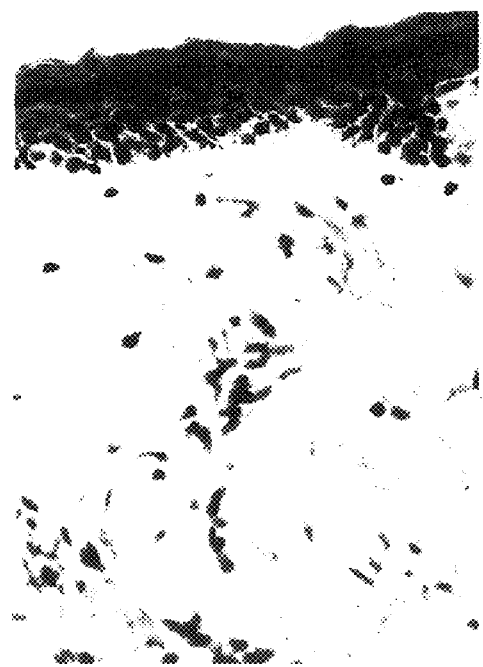
Figure 9D:
Figure 10A:
FIGS. 10A–D. Endothelial cells in muscle express CD40 in situ. Shown are immunohistologic studies of frozen sections demonstrating the expression of: (a) CD40, muscle (magnification 40×), (b) CD34, muscle (magnification 40×), (c) CD21, muscle (magnification 40×) and (d) control mouse IgG, muscle (magnification 40×).
Figure 10B:
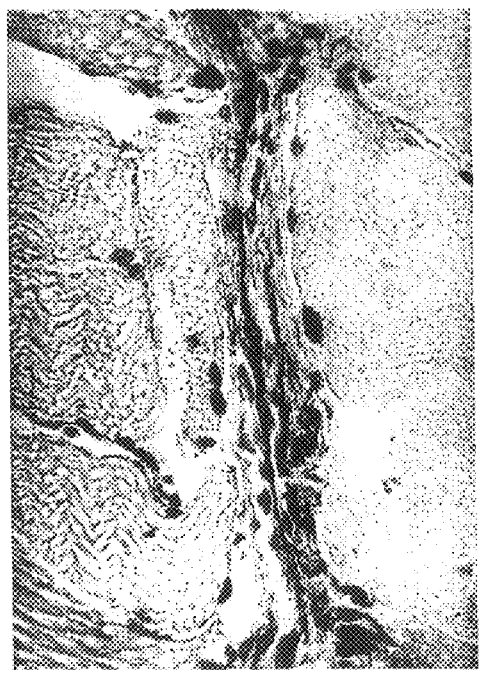
Figure 10C:
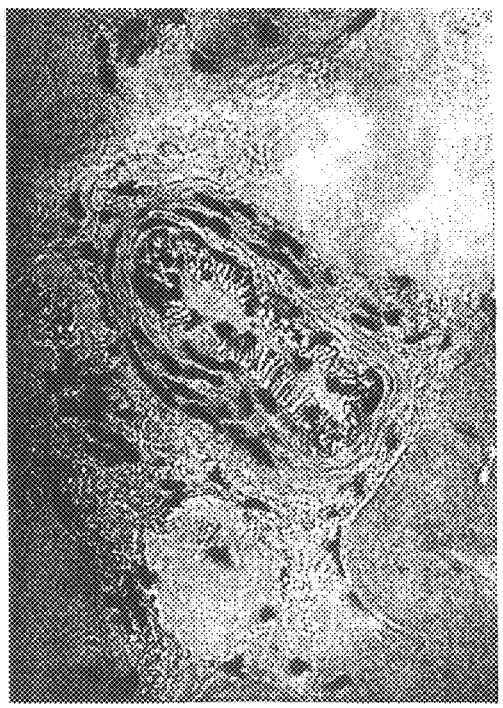
Figure 10D:
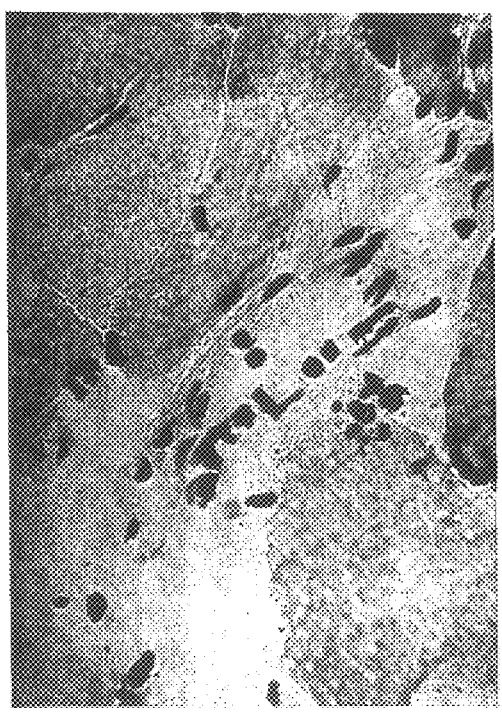

Because CD40 ligation induces B cell proliferation (5, 21), it was next asked if CD40L$^+$ cells induce proliferation of SM fibroblasts. Therefore, SM fibroblasts were cultured overnight in 1% FM to arrest growth, as previously described (32), and further additions to the cells were performed in 1% FM, unless otherwise indicated. Mitomycin-C treated CD40L+ B2.7 transfectants or CD40L− B2.7 cells were than added to the SM fibroblasts. Where indicated, co-culture experiments also included anti-CD40L mAb 5C8 or isotype control mAb P1.17. In some experiments, SM fibroblasts were pretreated overnight with rINF-γ prior to the addition of CD40L+ B2.7 transfectants. Because fibroblasts are known to proliferate in the presence of media containing 10% FCS ((32)), each experiment included control fibroblasts cultured in 10% FM. $^3$H thymidine incorporation was determined after 48 hours. CD40L+ B2.7 transfectants, in contrast to parental CD40L− B2.7 cells, induce SM fibroblast proliferation (FIG. 7). Furthermore, anti-CD40L mAb 5C8 specifically inhibits the ability of CD40L+ B2.7 transfectants to induce fibroblast proliferation (FIG. 7). In addition, pretreatment of SM fibroblasts with rINF-γ augments the capacity of CD40L+ B2.7 transfectants to induce SM fibroblast proliferation (FIG. 8). Together, these data demonstrate that CD40L mediated signals induce SM fibroblast proliferation in vitro and this effect is enhanced by rINF-γ.

Discussion

This study extends current knowledge of CD40 expression and function by specifically demonstrating that: 1) cultured SM or dermal fibroblasts express cell surface CD40 molecules as determined by FACS analysis, 2) rINF-γ upregulates fibroblast CD40 expression and this effect is augmented by rIL-1α or rTNF-α, 3) CD40L-CD40 interactions upregulates SM fibroblast CD54 and CD106 expression, 4) ligation of CD40 augments SM fibroblast IL-6 production and 5) induces SM fibroblast proliferation. Together, these data demonstrate that CD40L-CD40 interactions functionally activate fibroblasts in vitro.

Several lines of evidence suggest that T cells modulate fibroblast functions in vivo. This is of importance because fibroblasts play reparative roles following tissue injury by producing extracellular matrix proteins. In addition, lymphocytes, macrophages and fibroblasts are the predominant cell types in granulomatous inflammatory reactions characteristic of certain infections. Moreover, T cells directly or indirectly mediate fibroblast activation and collagen deposition seen in diseases such as scleroderma or chronic graft versus host disease (33–35).

Animal models demonstrate that T cells modulate fibroblast function during host responses to tissue injury. In this regard, studies of wound healing show that wound strength and hydroxyproline content are significantly decreased by treating mice with cyclosporine A (36) or T cell depleting anti-Thy 1.2 mAb (37). T cells also modulate outcome in various animal models of fibrosis. For example, bleomycin-induced pulmonary fibrosis is significantly attenuated in athymic mice relative to control euthymic mice (38). Moreover, joint or liver inflammatory reactions and collagen deposition are also significantly reduced in athymic rats following intraperitoneal injection of streptococcal cell wall extracts (39, 40).

One study suggests that human fibroblasts can express CD40 in vivo. Potocnik and coworkers studied the expression and distribution of various cell surface molecules, including CD40, on RA PBL, SF and SM (18). By immunohistochemistry they noted CD40 expression on a variety of cells in RA SM, including cells with spindle shape morphology suggestive of fibroblasts. SM fibroblasts are a predominant cellular component of the rheumatoid pannus. By producing collagenase, PGE2, IL-6 and other mediators, synovial fibroblasts are thought to be important contributors to the joint destruction characteristic of RA (30, 41–43). While electron microscopic studies have demonstrated direct T-fibroblast contact in rheumatoid synovial membrane (44), most studies have suggested that macrophage derived cytokines, such as IL-1 or TNF-α, activate fibroblasts (30). These studies suggest that direct contact mediated by CD40L-CD40 interactions also provides activation and proliferative signals to SM fibroblasts.

The mechanism by which CD40L mediated signals augment SM fibroblast proliferation is currently unknown. It is possible that CD40L-CD40 interactions induce the secretion of cytokines, such as IL-1, GM-CSF and FGF, which can stimulate SM fibroblast proliferation in an autocrine or paracrine manner (31). CD40 ligation also induces B cells to express c-myc (45) a proto-oncogene associated with proliferating cells. Immunohistologic studies demonstrate that RA SM fibroblast-like synoviocytes express c-myc in situ (46). Therefore, it will be of interest to specifically determine if CD40 ligation also induces c-myc expression in SM fibroblasts.

Similar to CD40 ligation on B cells (26), CD40L-CD40 interactions augment expression of fibroblast CD54 expression. In addition, CD40L-CD40 interactions upregulate fibroblast CD106 expression. CD54 and CD106 play key role in recruiting immune cells to sites of inflammation by interacting with CD11a/CD18 (LFA-1) or CD49d (VLA-4), respectively, expressed on leukocytes (24). There is also evidence that these ligand-counterligand interactions enhance proliferative signals to T cells (47). CD54 and CD106 are known to be expressed on RA fibroblast-like synoviocytes in vivo ((48–50)) and various cytokines upregulate synovial fibroblast CD54 and CD106 expression in vitro (49, 51, 52). Moreover, T cell adhesion to SM fibroblasts in vitro is partly mediated by CD11a/CD18-CD54 interactions (53) and CD49d-CD106 interactions (49). Therefore, CD54 and CD106 upregulation on SM fibroblasts by CD40L+ T cells may represent a mechanism to augment cytokine mediated inflammatory cell recruitment/retainment to SM. Additionally, CD40L mediated SM fibroblast CD54 and CD106 upregulation may play direct signaling roles to T cells via interactions with their counter-receptors.

It is of interest that in vivo administration of a hamster anti-murine CD40L mAb (MR1) prevents the induction of collagen-induced arthritis, a murine model of RA (54). The fact that MR1 blocks the production of anti-collagen autoantibodies likely relates to the known role of CD40L-CD40 interactions in T cell dependent humoral immune responses (9–11). Moreover, MR1 prevents the development of synovial lining cell thickening and SM inflammatory cell infiltration characteristic of collagen-induce arthritis (54). These studies suggest that T cell-fibroblast CD40L-CD40 interactions play roles in mediating inflammatory reactions seen in collagen-induced arthritis, an also plays immunopathogenic roles in human fibrotic diseases such as RA or scleroderma, mediated in part by T cell-dependent fibroblast activation. Moreover, this study provides new rational for blocking CD40L-CD40 interactions as therapy for human diseases mediated by CD4+ T cell induced fibroblast activation.

TABLE 1

| Stimuli | OA.2 | | OA.3 | | IA.1 | |
| --- | --- | --- | --- | --- | --- | --- |
| | CD40 | CD54 | CD40 | CD54 | CD40 | CD54 |
| Media | 18 | 129 | 76 | 134 | 47 | 120 |
| rINF-γ | 56 | 703 | 228 | 668 | 95 | 755 |
| rIL-1α | 22 | 286 | 82 | 304 | 37 | 292 |
| rTNF-α | 22 | 568 | 96 | 506 | 66 | 594 |

Table 1 Legend. Cytokine regulation of SM fibroblast CD40 expression. Shown is CD40 expression (mean fluorescence intensity) as determined by FACS analysis on the indicated SM fibroblast lines following coculture with media, rINF-γ (1000 U/ml), rIL-1α (10 pg/ml) or rTNF-α (200 U/ml). Background staining (MFI) of a control mAb is subtracted for each value.

Second Series of Experiments
Materials and Methods

Monoclonal antibodies, lectins and T cell lines The IgG2a murine anti-CD40L mAb (5C8) was previously generated (20). Hybridomas W6/32 (anti-MHC Class I), L243 (anti-MHC Class II), 3C10 (anti-CD14), THB.5 (anti-CD21), G28.5 (anti-CD40) and GAP 8.3 (anti-CD45) were purchased from American Type Culture Collection (ATCC) (Rockville, Md.). Hybridoma ascites was purified on a Protein G column (Pharmacia, Piscataway, N.J.). FITC conjugated anti-CD13, FITC conjugated anti-CD19 and PE conjugated anti-CD54 mAbs was purchased from Biosource International (Camarillo, Calif.) and anti-CD34 mAb was obtained from Biogenex (San Ramon, Calif.). An additional anti-CD54 mAb, as well as anti-CD62E and anti-CD106 mAbs, were kindly provided by Biogen (Cambridge, Mass.). L243 and mAbs provided by Biogen were biotinylated as previously described (37). PE conjugated anti-CD80 and biotinylated anti-CD86 mAbs were purchased from Becton Dickinson (San Jose, Calif.) and PharMingen (San Diego, Calif.), respectively. Isotype control mAbs utilized for FACS analysis were purchased from Becton Dickinson or Caltag Laboratories (South San Francisco, Calif.). P1.17 is an irrelevant control IgG2a murine mAb (Biogen) utilized for functional studies. FITC conjugated UEA-1 were obtained from Sigma (St. Louis, Mo.).

D1.1 is a Jurkat T cell subclone that constitutively expresses CD40L (20, 42). B2.7 is a CD40L$^-$ Jurkat T cell subclone (20, 42). Stably transfected CD40L$^+$ 293 kidney cells or CD8$^+$ 293 kidney cells were generated as previously reported (37). Ramos 2G6 B cells respond to CD40L mediated signals (38, 39) and were obtained from ATCC.

Endothelial cell cultures

Human umbilical vein endothelial cells (HUVEC) were isolated as previously reported (40, 41). HUVEC were cultured in M199 media (Gibco, Grand Island, N.Y.) supplemented with 25% FCS (Summit Biotechnology, St. Collins, Colo.), 5% human serum (Gemini, Calabasas, Calif.), heparin 90 $\mu$/ml (Sigma), endothelial cell growth factor 15 $\mu$g/ml (Collaborative Research, Bedford, Mass.) and 1% penicillin-streptomycin (Sigma) (M199 complete media). HUVEC were passaged by treatment for 3 minutes with 1% Trypsin-EDTA (Sigma). All HUVEC experiments were performed in M199 complete media following 1–3 passages.

Studies on the effects of cytokines on HUVEC CD40 expression

To study the effects of cytokines on CD40 expression, HUVEC were cultured in 6 well plates (Nunc, Denmark) and grown to near confluence. The media was aspirated and HUVEC were then incubated with rIFN-γ 1000 U/ml (Biogen), rIL-1α 10 pg/ml (R & D, Minneapolis, Minn.) or rTNF-α 200 U/ml (Upstate Biotechnology, Lake Placid, N.Y.) in 3 ml of M199 complete media. At the indicated times, media was aspirated, cells were washed once with saline and 1 ml of 1% trypsin-EDTA was added to the wells. Cold Isocove's Modified Dulbecco's Media (Gibco) containing 10% FCS (Summit) was added to the wells after 3 minutes and the cells collected for FACS analysis.

Studies on functional consequences of HUVEC CD40 ligation.

To study the effect of CD40 ligation on the expression of HUVEC cell surface molecules, cells were cultured in 6 well plates as described above. When HUVEC were near confluence 1×10$^6$ CD40L$^+$ Jurkat D1.1 cells, CD40L$^-$ Jurkat B2.7 cells, CD40L$^+$ 293 kidney cell transfectants or CD8 kidney cell transfectants were added to the culture. Where indicated, CD40L$^+$ cells were pretreated with anti-CD40L mAb 5C8 (10 $\mu$g/ml) or isotype control mAb P1.17 (10 $\mu$g/ml) prior to the addition to HUVEC. After the indicated time in culture the cells were collected by trypsinization and two-color FACS analyses performed.

Functional studies of CD40 ligation on Ramos 2G6 cells.

Control experiments of CD40 ligation on Ramos 2G6 cells were performed by culturing 2×10$^5$ Ramos 2G6 cells with 1×10$^5$ D1.1 cells or control cells for 24 h hours in 96 well plates containing 200 $\mu$l of Isocove's Modified Dulbecco's Media (Gibco) containing 10% FCS (Summit) and 1% penicillin-streptomycin (Sigma).

Cytofluorographic analysis

The methods utilized for cytofluorographic analysis have been previously described (20, 42). In all experiments the cells were first treated with aggregated human immunoglobulin (Enzyme International, Fallbrook, Calif.) to block non-specific Ig binding. For single-color FACS analysis, cells were stained with saturating concentrations of primary antibody for 30–60 minutes at 4° C. Following washing, FITC conjugated F(ab)$_2$ goat anti-mouse IgG (Jackson Immunoresearch Laboratories, West Grove, Pa.) was added for 30–60 minutes at 4° C. The cells were washed and fixed with 1% formaldehyde prior to FACS analysis. For two-color FACS analysis, cells were first stained with the indicated biotinylated mAbs. Following washing, cells were then stained with streptavidin-PE (Calbiochem, La Jolla, Calif.) and FITC conjugated anti-CD13 mAb or FITC conjugated UEA-1, as indicated. HUVEC were distinguished from Jurkat cells in two-color FACS analysis by positive staining with anti-CD13 mAb or UEA-1, a lectin that selectively binds endothelial cells (43). Fluorescence intensity was measured on a FACScan cytofluorograph with the Consort-30 software (Becton-Dickinson, Mountainview, Calif.). Mean fluorescence intensity (MFI) refers to values normalized to the log scale as calculated by the Consort 30 software.

Characterization of endothelial cell CD40 expression in situ.

Frozen sections of normal spleen, thyroid, skin, muscle, kidney, lung or umbilical cord were studied for CD40 expression, as previously described (38). Immunohistologic analysis was performed with the indicated mAbs and reactivity detected using Vector ABC Elite kit and 3-amino-9-ethylcarbazole (AEC) (Vector Laboratories, Burlingame, Calif.) according to manufacture's instructions. Control frozen sections were stained with appropriate concentrations of mouse IgG (Sigma).

Results

In situ and in vitro characterization of endothelial cell CD40 expression.

Figure 11A:
FIGS. 11A–B. Endothelial cells in spleen express CD40 in situ. Shown are immunohistologic studies of frozen sections demonstrating the expression of: (a) CD40, spleen (magnification 10×) and (b) control mouse IgG, spleen (magnification 10×).
Figure 11B:
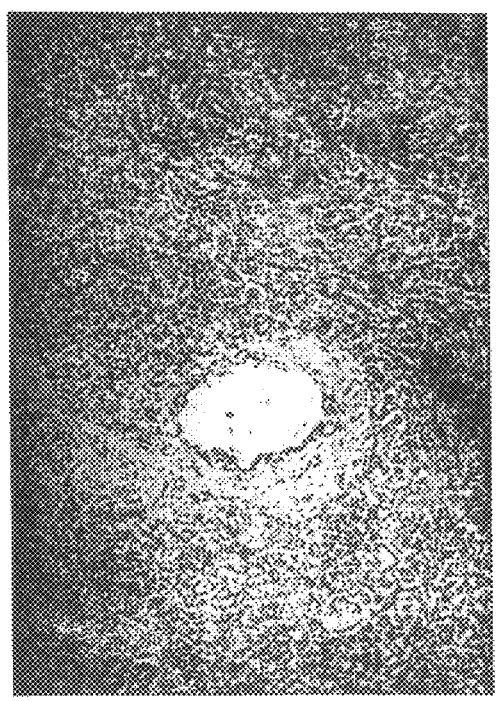

The first series of experiments were performed to determine if normal endothelial cells express CD40 in situ. Therefore, frozen sections obtained from normal spleen, thyroid, skin, muscle, kidney, lung or umbilical cord were stained with anti-CD40 mAb or control mouse IgG and endothelial cell reactivity noted. Additional controls included staining with anti-CD34 mAb (reactive with hematopoietic stem cells and endothelial cells (44)) or anti-CD21 mAb (reactive with B cell cells and epithelial cells (17)). Endothelial cells from all tissues studied express CD40 in situ. FIGS. 9–11 demonstrate representative CD40 staining of endothelial cells in normal skin (FIG. 9), muscle (FIG. 10) and spleen (FIG. 11). The pattern of endothelial reactivity was similar to that seen with anti-CD34 mAb (FIGS. 9 and 10). In contrast, endothelial cells did not react with anti-CD21 mAb (FIGS. 9 and 10) or mouse IgG (FIGS. 9–11).

Figure 12:
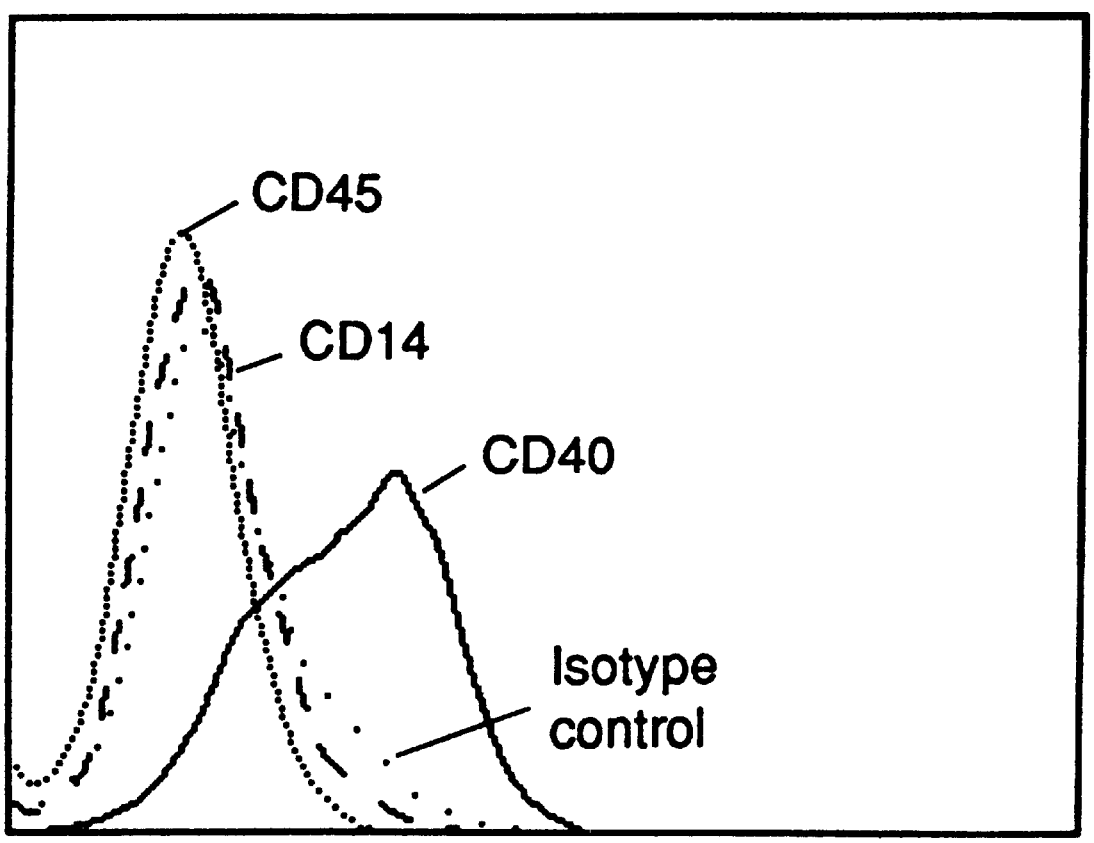
FIG. 12. Expression of CD40 on HUVEC cells in vitro. Shown are overlapping FACS analysis of CD14, CD40, CD45 or isotype control expression on HUVEC following the first passage. The mean fluorescence intensity of CD14, CD40, CD45 or isotype control expression is 7, 24, 5 and 9, respectively. Shown is representative of CD40 expression on HUVEC isolated from 15 umbilical cords.

To further explore endothelial cell CD40 expression and function in vitro it was next asked if cultured human umbilical vein endothelial cells (HUVEC) also express CD40. HUVEC were isolated, grown to confluence and CD40 expression determined by FACS analysis following trypsinization. The cells morphologically resembled endothelial cells and phenotypic analysis demonstrated that the cells were $CD13^+$ and reactive with UEA-1, a lectin that selectively binds endothelial cells (43). In addition, the cells were $CD14^-$ $CD45^-$MHC Class $II^-$ by FACS analysis. Therefore, these cultures did not contain significant numbers of contaminating non-endothelial cells. HUVEC constitutively express CD40 in vitro (FIG. 12). Similar results were obtained from HUVEC isolated from 15 individuals.

To determine if pro-inflammatory cytokines regulate endothelial cell CD40 expression, as has been shown for B cells (45), monocytes (14), thymic epithelial cells (18) and fibroblasts (19), HUVEC were cultured with rIFN-γ, rIL-1α, or rTNF-α for 48 hours. rINF-γ, in contrast to rIL-1α or rTNF-α, induces 2–3 fold increase in HUVEC CD40 expression (table 2). Together, these studies demonstrate that endothelial cells from normal tissue express CD40 in situ and in vitro and that rIFN-γ upregulates endothelial cell CD40 expression in vitro.

Effect of CD40L-CD40 interactions on HUVEC CD54, CD62E and CD106 expression.

Figure 13:
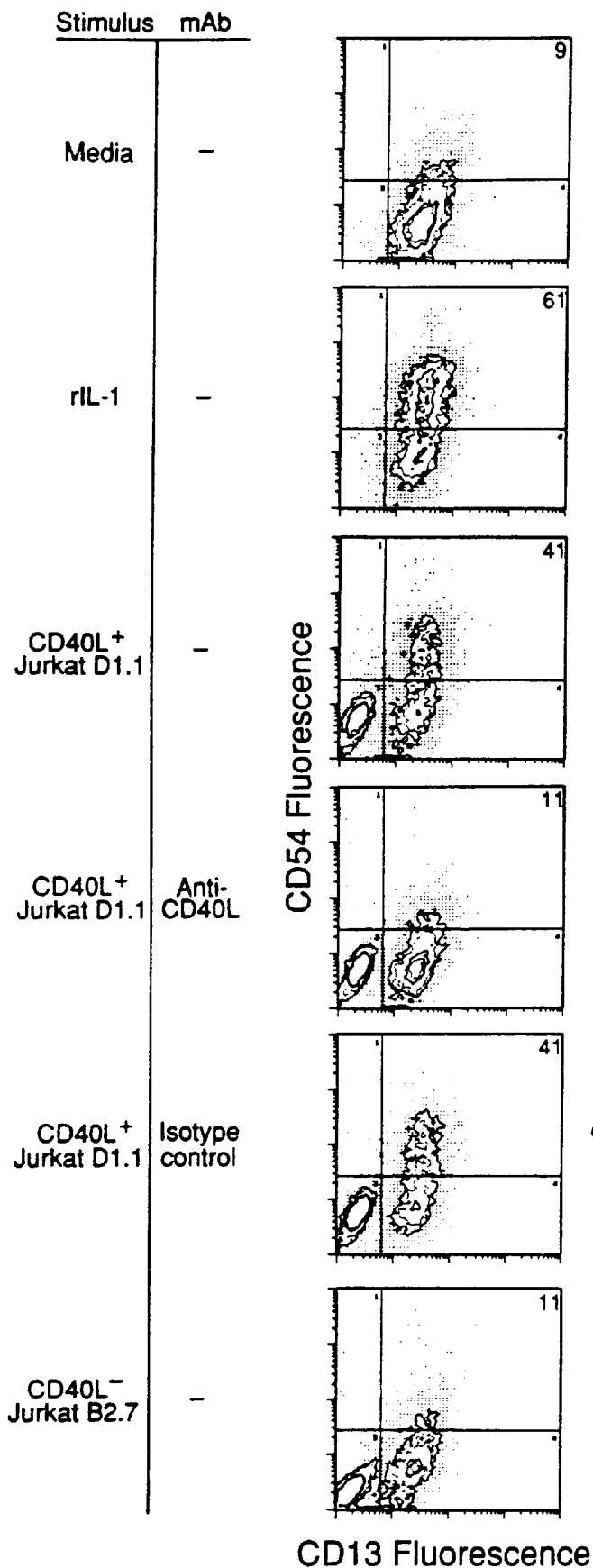
FIGS. 13A–F. Effect of CD40L-CD40 interactions on HUVEC CD54 (ICAM-1) expression. Shown are two-color contour graphs demonstrating the effects on HUVEC CD54 expression following culture with media, CD40L⁺ Jurkat D1.1 cells or CD40L⁻ Jurkat B2.7 cells for 6 hours. Where indicated, CD40L⁺ D1.1 cells were pretreated with anti-CD40L mAb 5C8 or isotype control mAb P1.17. The X-axis demonstrates CD13 expression and the Y-axis demonstrates CD54 expression. The numbers in the upper right hand corner of each graph indicates percentage of CD13⁺ cells expressing CD54 (background staining of control mAb is subtracted for each value). Shown is representative of 3 similar experiments with different HUVEC lines.
Figure 14:
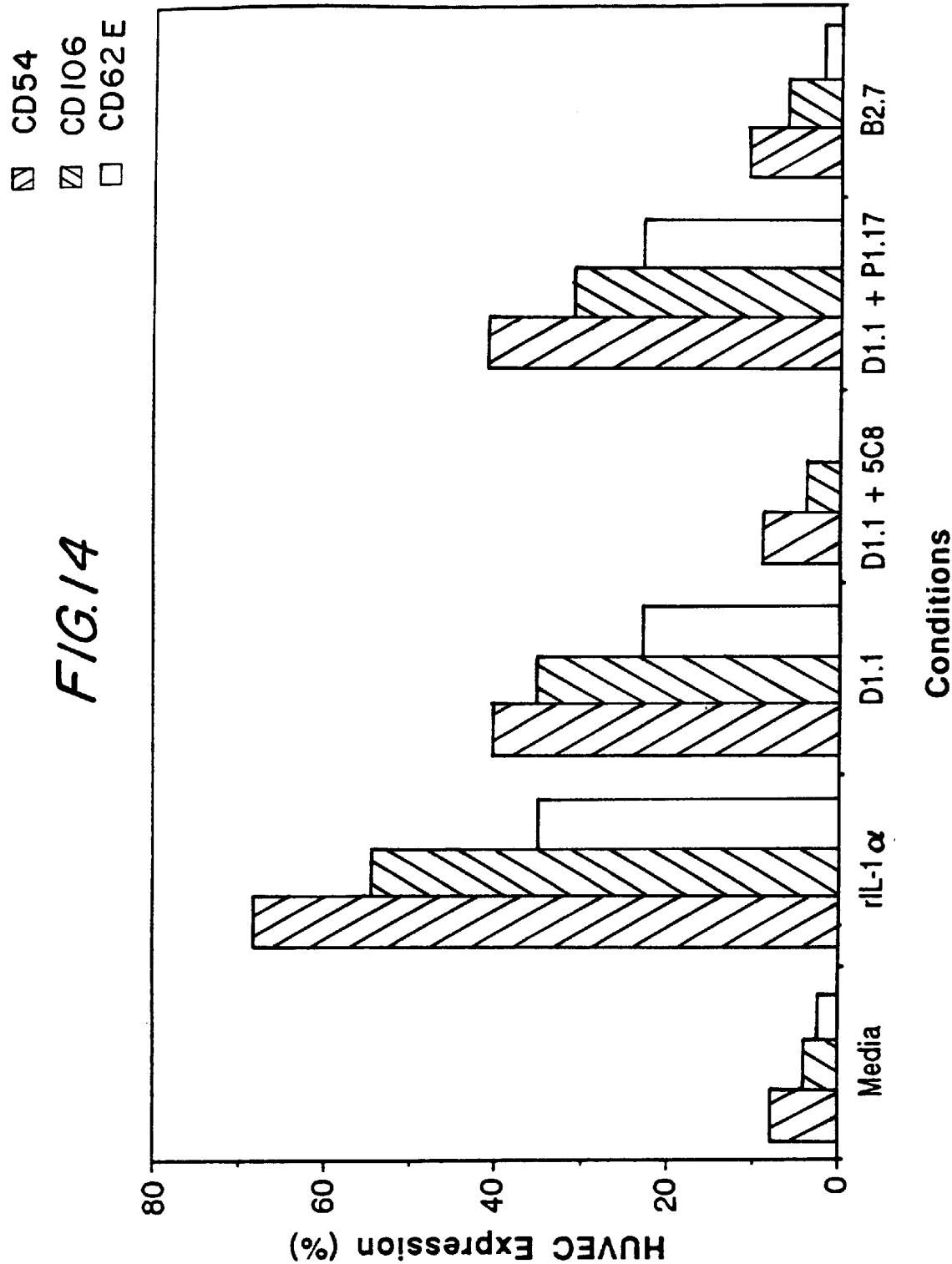
FIG. 14. Effect of CD40L-CD40 interactions on HUVEC CD54 (ICAM-1), CD62E (E-selectin) and CD106 (VCAM- 1) expression. Shown are bar graphs representing the percentage of HUVEC expressing CD54, CD62E or CD106 following culture for 6 hours with media, rIL-1α, CD40L+ Jurkat D1.1 cells or CD40L− Jurkat B2.7 cells. Where indicated, CD40L+ D1.1 cells were pretreated with anti-CD40L mAb 5C8 or isotype-control mAb P1.17. HUVEC CD54, CD62E and CD106 expression was determined by two-color FACS analysis as shown in FIG. 3. Background staining of control mAb is subtracted for each value. Shown is representative of 3 similar experiments with different HUVEC lines.

Activated endothelial cells express cell surface molecules, such as CD54, CD62E and CD106 that play important roles in mediating intercellular adhesive interactions (1, 2). Interestingly, ligation of CD40 on B cells (46) or fibroblasts (19) induces the upregulation of adhesion molecules. Therefore, it was next asked if CD40L-CD40 interactions effect the expression of CD54, CD62E or CD106 expression on HUVEC in vitro as determined by two-color FACS analysis. HUVEC were cultured with $CD40L^+$ Jurkat D1.1 cells or $CD40L^-$ Jurkat B2.7 cells. Where indicated, Jurkat D1.1 cells were pretreated with anti-CD40L mAb 5C8 or control mAb prior to the addition to HUVEC. As a positive control, HUVEC were also cultured with rIL-1α. $CD40L^+$ Jurkat D1.1 cells, but not $CD40L^-$ Jurkat B2.7 cells, induce CD54, CD62E and CD106 upregulation on HUVEC (FIGS. 13 and 14). This effect of D1.1 cells is inhibited by anti-CD40L mAb 5C8 but not by an isotype control mAb (FIGS. 13 and 14). These studies strongly suggest that CD40L-CD40 interactions upregulate CD54, CD62E and CD106 expression on HUVEC.

Effect of $CD40L^+$ 293 kidney cell transfectants on HUVEC CD54, CD62E and CD106 expression.

To determine if CD40L mediated signals were sufficient, in the absence of additional lymphoid specific interactions, to upregulate endothelial cell adhesion molecules, HUVEC were cultured with stably transfected $CD40L^+$ 293 kidney cells or control $CD8^+$ 293 transfectants. As a positive control, HUVEC were also cultured with $CD40L^+$ D1.1 cells. Similar to $CD40L^+$ D1.1 cells, CD40t 293 kidney cell transfectants upregulate CD54, CD62E and CD106 expression on HUVEC (FIG. 15). Control 293 CD8 transfectants have no effect on HUVEC CD54, CD62E or CD106 expression. Together, these studies demonstrate that CD40L-CD40 interactions are sufficient to upregulate these adhesion molecules on HUVEC in vitro.

Analysis of the kinetics of CD40L mediated HUVEC CD54, CD62E and CD106 upregulation.

Figure 16B:
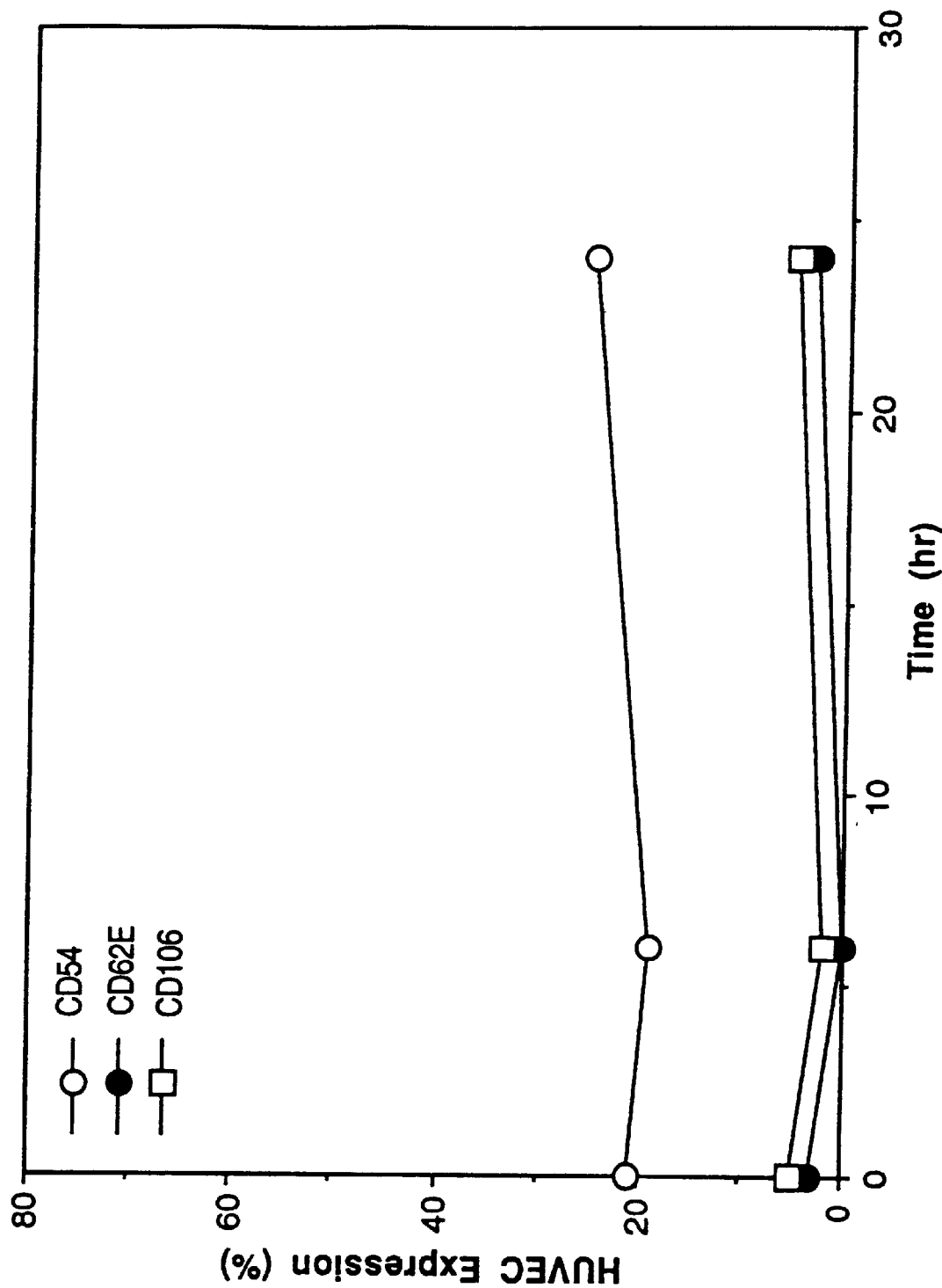
FIG. 16B. Same as FIG. 16A except that HUVEC were cultured with CD40L- Jurkat B2.7 cells.

The kinetics of CD54, CD62E or CD106 upregulation by rIL-1α or rTNF-α in vitro has been well established (1, 2). CD54 and CD106 are upregulated 6 hours following activation and expression persist for greater than 24 hours. In contrast, CD62E expression peaks 6 hours following activation and returns to baseline (no expression) by 24 hours. In the next series of experiments the kinetics of CD40L induced HUVEC CD54, CD62E or CD106 upregulation were determined. HUVEC were cultured with $CD40L^+$ D1.1 cells or CD40L B2.7 cells and analyzed at various time points for CD54, CD62E or CD106 expression. Following culture with $CD40L^+$ D1.1 cells, HUVEC CD54 or CD106 expression was upregulated by 6 hours and persisted in expression for greater than 24 hours (FIG. 16). In contrast, CD40L induced CD62E expression peaked by 6 hours and returned to baseline by 24 hours (FIG. 16). Therefore, the kinetics of CD40L, rTNF-α or rIL-1α mediated upregulation of HUVEC CD54, CD62E or CD106 are similar.

Determining if CD40L-CD40 interactions upregulate CD80, CD86 or MHC Class II expression on HUVEC.

Activated endothelial cells are competent to express MHC Class II molecules and deliver costimulatory signals to T cells (10, 47–49). Ligation of CD40 on B cells or dendritic cells upregulates MHC Class II expression, as well as, the expression of the costimulatory molecules CD80 and CD86 (36, 37, 50–52). Therefore the next series of experiments determined if CD40L-CD40 interactions similarly upregulates MHC Class II, CD80 or CD86 expression on HUVEC. HUVEC were cultured with $CD40L^+$ D1.1 cells or $CD40L^-$ B2.7 cells for 24 or 48 hours and CD80, CD86 and MHC Class II expression determined by two-color FACS analysis. As a positive control for the effect of HUVEC CD40 ligation, CD54 expression was also determined. In addition, HUVEC were also cultured with rIFN-γ as a control for MHC Class II upregulation. As a positive control for CD40L mediated CD80, CD86 and MHC Class II upregulation, D1.1 cells were cultured with Ramos 2G6 B cells (38–39). In contrast to the effects of CD40 ligation on B cells or dendritic cells, CD40L-CD40 interactions do not upregulate MHC Class II, CD80 or CD86 expression on HUVEC (table 3).

Discussion

CD40 is a cell surface molecule constitutively expressed on a variety of cells, including B cells (12, 13), monocytes (14), dendritic cells (15), epithelial cells (17, 18), basophils (16) and fibroblasts (19). The counter-receptor for CD40 is CD40L, a 30–33 kDa activation-induced, transiently expressed $CD4^+$ T cell surface molecule (20–25). It is shown that endothelial cells in spleen, thyroid, skin, muscle, kidney, lung or umbilical cord express CD40 in situ. This finding is consistent with a previous report that endothelial cells in rheumatoid arthritis synovial membrane express CD40 (11). In addition, human umbilical vein endothelial cells (HUVEC) express CD40 in vitro. Most importantly, CD40 expression on endothelial cells is functionally significant because $CD40L^+$ Jurkat T cells or $CD40L^+$ 293 kidney cell transfectants, but not control cells, upregulate the expression of intercellular adhesion molecules CD54 (ICAM-1), CD62E (E-selectin) and CD106 (VCAM-1) on HUVEC. The results disclosed herein demonstrate that endothelial cells express CD40 and CD40L-CD40 interactions induce endothelial cell activation in vitro.

Endothelial cells play central roles in inflammatory responses in part by expressing CD54, CD62E and CD106 (1, 2). These adhesion molecules interact with specific cell surface receptors on leukocytes and promote the transmigration of inflammatory cells across the endothelial cell barrier. The expression of these particular endothelial cell surface molecules are tightly regulated (1, 2). Resting endothelial cells express low levels of CD54 and minimal or no CD62E or CD106. However, endothelial cells upregulate CD54, CD62E and CD106 expression following activation with IL-1 or TNF. These findings demonstrate a means by which activated CD4$^+$ T cells upregulate endothelial cell adhesion molecules by direct cell-cell contact.

Because CD40L expression is also tightly regulated, it is likely that CD40L-CD40 interactions occur during Ag driven immune responses. In this regard, in vitro studies demonstrate that resting CD4$^+$ T cells do not express, detectable ° CD40L (20–22, 25, 53). However, CD40L is transiently expressed on activated CD4$^+$ T cells in vitro; peak expression is seen 6 hours following activation and levels return to baseline (no expression) by 24–48 hours (20, 21, 53). CD40L is also rapidly down-modulated by CD40 expressing cells in a process that is at least partly due to receptor-mediated endocytosis (54). In vivo, CD40L expression is normally restricted to CD4$^+$ T cells in secondary lymphoid tissue (38), the site of MHC restricted, Ag specific T-B interactions. However, immunohistologic studies of rheumatoid arthritis synovial membrane or psoriatic plaques demonstrates the presence of CD40L$^+$ CD4$^+$ T cells. These studies suggest that APCs at sites of inflammation induce infiltrating CD4$^+$ T cell to express CD40L. CD40L$^+$ CD4$^+$ T cells then play roles in augmenting the inflammatory process by interacting with CD40$^+$ endothelial cells. The functional consequences of this interaction enable further adhesion and transmigration of immune cells at sites of inflammation.

The fact that CD40 ligation regulates the expression of endothelial cell surface adhesion molecules is consistent with a general role for CD40 signalling in regulating the expression and/or function of adhesion molecules on a variety of cells. In this regard, it has been shown that CD40L mediated signals induce CD54 and CD106 upregulation on fibroblasts cultured from synovial membrane (19). CD40 ligation also upregulates CD54 expression on B cells (46) and induces CD54 dependent homoaggregation of B cells (55). Interestingly, pretreatment of B cells with anti-CD40 mAb augments heterotypic interactions of B cells with activated endothelial cells in vitro in a manner dependent on CD49d (VLA-4)/CD106 interactions (56). Because CD40 ligation did not upregulate B cell CD49d expression, it was hypothesized that CD40 mediated signals induced CD49d activation.

CD40 ligation on B cells or dendritic cells also upregulates expression of MHC Class II, as well as, the costimulatory molecules CD80 and CD86 (36, 37, 50–52). Interestingly, endothelial cells stimulated with rIFN-γ are competent to express MHC Class II in vitro (57) and endothelial cells in situ within inflammatory tissue can express MHC Class II (10, 58–60). Moreover, endothelial cells are competent to present Ag to T cells in vitro and deliver appropriate costimulatory signals to T cells required for IL-2 production and proliferation (10, 47–49).

However, it is shown here that CD40L-CD40 interactions do not upregulate MHC Class II, CD80 or CD86 expression on HUVEC in vitro. This finding is consistent with previous studies suggesting that human endothelial cells do not express CD80 (47, 61). The costimulatory molecules expressed on endothelial cells are not precisely know. Work by Pober and colleagues demonstrate that blocking CD2-CD54 (LFA-3) interactions inhibits the ability of endothelial cells to induce allogenic T cell proliferation (47, 48). However, it is unclear if CD2-CD58 interactions enhance intercellular adhesiveness and/or deliver costimulatory signals to T cells. It will be of interest to determine if CD40L mediated signals modulate the capacity of endothelial cells to activate T cells.

Finally, endothelial cells are activated in a variety of diseases mediated by CD4$^+$ T cells. For example, endothelial cell surface adhesion molecules are upregulated in rheumatoid arthritis (62), scleroderma (63) and in transplant rejection (64). In addition, CD4$^+$ T cells play roles in atherosclerosis (65) and accelerated atherosclerosis associated with transplantation (60). The precise mechanistic role of CD40L mediated interactions with endothelial cells in these diseases is not known. However, an antibody to CD40L, MR1, inhibits murine models of diseases mediated by CD4$^+$ T cells and/or inflammatory cell infiltrates. For example, MR1 prevents the synovial lining cell hypertrophy and cellular infiltrate associated with collagen-induce arthritis, a murine model of rheumatoid arthritis (66). Moreover, MR1 inhibits a murine model of multiple sclerosis (EAE) and inhibits allograft rejection (67). Blocking CD40L dependent interactions with endothelial cells and/or fibroblasts mediates, in part, these effects of MR1. The results disclosed herein suggest that CD40L-CD40 interactions on the surface of endothelial cells play immunopathogenic roles in inflammatory diseases.

TABLE 2

| Stimuli | HUVEC Expression | |
|---|---|---|
| | CD40 (MFI) | CD54 (MFI) |
| Media | 17 | 22 |
| rINF-γ | 42 | 44 |
| rIL-1α | 24 | 51 |
| rTNF-α | 22 | 54 |

Table 2 Legend. Effect of cytokines on HUVEC CD40 expression. Shown is the mean fluorescence intensity (MFI) of CD40 or CD54 expression on HUVEC cultured in the presence or absence of rIFN-γ (1000 U/ml), rIL-1α (10 pg/ml) or rTNF-α (200 U/ml) for 48 hours. CD40 or CD54 MFI was determined by FACS analysis and background staining of control mAb is subtracted for each value. Similar results were obtained in 2 additional experiments with different HUVEC lines.

TABLE 3

| | HUVEC Expression (MFI) | | | | Ramos Expression (MFI) | | | |
|---|---|---|---|---|---|---|---|---|
| Conditions | CD54 | CD80 | CD86 | MHC II | CD54 | CD80 | CD86 | MHC II |
| Media | 8 | 0 | 1 | 0 | 22 | 0 | 7 | 128 |
| D1.1 | 78 | 0 | 0 | 0 | 71 | 8 | 13 | 223 |
| B2.7 | 23 | 0 | 1 | 1 | 25 | 1 | 7 | 127 |
| rIFN-γ | 16 | 0 | 0 | 97 | ND | ND | ND | ND |

Table 3 Legend. Effect of CD40L-CD40 interactions on HUVEC MHC Class II, CD80 and CD86 expression. Shown is the mean fluorescence intensity of HUVEC CD54, CD80, CD86 or MHC Class II expression following culture with media, rIFN-γ (1000 U/ml), CD40L$^+$ Jurkat D1.1 cells or CD40L B2.7 cells for 48 hours. In a parallel experiment, the CD40L responsive Ramos 2G6 B cell line (38–39) was cultured with media, CD40L$^+$ Jurkat D1.1 cells or CD40L B2.7 cells for 24 hours. HUVEC or Ramos 2G6 MHC Class II, CD54, CD80 and CD86 expression was determined by two-color FACS analysis. Background staining of control mAb is subtracted for each value. Shown is representative of 3 similar experiments with different HUVEC lines. ND= not done.

REFERENCES FOR BACKGROUND

1. Pauli, S., Ehlin-Henriksson, B., Mellstedt, H., Koho, H., Ben-Aissa, H. Perlmann, P. (1985) A p50 surface antigen 1. restricted to human urinary bladder carcinomas and B lymphocytes. Cancer Immunol. Immunother. 20, 23–28.

2. Clark, E. A. Ledbetter, J. A. (1986) Activation of human B cells mediated through two distinct cell surface differentiation antigens, Bp35 and Bp50. Proc. Natl. Acad. Sci. USA. 83, 4494–4498.

3. Lederman, S., Yellin, M. J., Krichevsky, A., Belko, J., Lee, J. J. Chess, L. (1992) Identification of a novel surface protein on activated CD4$^+$ T cells that induces contact-dependent B cell differentiation (help). J Exp Med. 175, 1091–1101.

4. Lane, P., Traunecker, A., Hubele, S., Inui, S., Lanzavecchia, A. Gray, D. (1992) Activated human T cells express a ligand for the B cell-associated antigen CD40 which participates in T cell-dependent activation of B lymphocytes. Eur J Immunol. 22, 2573–2578.

5. Armitage, R. J., Fanslow, W. C., Strockbine, L., Sato, T. A., Clifford, K. N., Macduff, B. M., Anderson, D. M., Gimpel, S. D., Davis, S. T., Maliszewski, C. R. et, a.l. (1992) Molecular and biological characterization of a murine ligand for CD40. Nature. 357, 80–82.

6. Graf, D., Korthauer, U., Mages, H. W., Senger, G. Kroczek, R. A. (1992) Cloning of TRAP, a ligand for CD40 on human T cells. Eur J Immunol. 22, 3191–3194.

7. Hollenbaugh, D., Grosmaire, L. S., Kullas, C. D., Chalupny, N. J., Braesch-Andersen, S., Noelle, R. J., Stamenkovic, I., Ledbetter, J. A. Aruffo, A. (1992) The human T cell antigen gp39, a member of the TNF gene family, is a ligand for the CD40 receptor: experssion of a soluble form of gp39 with B cell co-stimulatory activity. EMBO J. 11, 4313–4321.

8. Noelle, R. J., Roy, M., Shepherd, D. M., Stamenkovic, I., Ledbetter, J. A. Aruffo, A. (1992) A 39-kDa protein on activated helper T cells binds CD40 and transduces the signal for cognate activation of B cells. Proc Natl Acad Sci USA. 89, 6550–6554.

9. Lederman, S., Yellin, M. J., Cleary, A. M., Fortune, S. M. Chess, L. (1994) The understanding of contact-dependent T-cell helper function in molecular, cellular and physiological detail. Res Immunol. 145, 215–220.

10. Noelle, R. J., Ledbetter, J. A. Aruffo, A. (1992) CD40 and its ligand, an essential ligand-receptor pair for thymus-dependent B-cell activation. Immunol Today. 13, 431–433.

11. Banchereau, J., Bazan, F., Blanchard, D., Briere, F., Galizzi, J. P., van Kooten, C., Liu, Y. J., Rousset, F. Saeland, S. (1994) The CD40 antigen and its ligand. Annu. Rev. Immunol. 12, 881–922.

12. Korthauer, U., D. Graf, H. W. Mages, F. Briere, M. Padayachee, S. Malcolm, A. G. Ugazio, L. D. Notarangelo, R. L. Levinsky and R. A. Kroczek. 1993. Defective expression of T-cell CD40 ligand causes X-linked Immunodeficiency with hyper-IgM. Nature. 361: 539.

13. DiSanto, J. P., J. Y. Bonnefoy, J. F. Gauchat, A. Fischer and G. de Saint Basile. 1993. CD40 ligand mutations in X-linked immunodeficiency with hyper-IgM. Nature. 361: 541.

14. Allen, R. C., R. J. Armitage, M. E. Conley, H. Rosenblatt, N. A. Jenkins, N. G. Copeland, M. A. Bedell, S. Edelhoff, C. M. Distèche, D. K. Simoneaux and a. 1. et. 1993. CD40 ligand gene defects responsible for X-linked hyper-IgM syndrome. Science. 259: 990.

15. Aruffo, A., M. Farrington, D. Hollenbaugh, X. Li, A. Milatovich, S. Nonoyama, J. Bajorath, L. S. Grosmaire, R. Stenkamp, M. Neubauer and a. 1. et. 1993. The CD40 ligand, gp39, is defective in activated T cells from patients with X-linked hyper-IgM syndrome. Cell. 72: 291.

16. Ramesh, N., R. Fuleihan, V. Ramesh, S. Lederman, M. J. Yellin, S. Sharma, L. Chess, F. S. Rosen and R. S. Geha. 1993. Deletions in the ligand for CD40 in X-linked immunoglobulin deficiency with normal or elevated IgM (HIGMX-1). Int Immunol. 5: 769.

17. Kawabe, T., T. Naka, K. Yoshida, T. Tanaka, H. Fujiwara, S. Suematsu, N. Yoshida, T. Kishimoto and H. Kikutani. 1994. The immune response in CD40-deficient mice: impaired immunoglobulin class switching and germinal center formation. Immunity. 1: 167.

18. Xu, J., T. M. Foy, J. D. Laman, E. A. Elliot, J. J. Dunn, T. J. Waldschmidt, J. Elsemore, R. J. Noelle and R. A. Flavell. 1994. Mice deficient for the CD40 ligand. Immunity. 1: 423.

19. Alderson, M. R., R. J. Armitage, T. W. Tough, L. Strockbine, W. C. Fanslow and M. K. Spriggs. 1993. CD40 expression by human monocytes: regulation by cytokines and activation of monocytes by the ligand for CD40. J Exp Mod. 178: 669.

20. Caux, C., C. Massacrier, B. Banbervliet, B. Dubois, C. Van Kooten, I. Durand and J. Banchereau. 1994. Activation of human dendritic cells through CD40 cross-linking. J. Exp. Med. 180: 1263.

21. Galy, A. H. and H. Spits. 1992. CD40 is functionally expressed on human thymic epithelial cells. J Immunol. 149: 775.

22. Freudenthal, P. S. Steinman, R. M. (1990) The distinct surface of human blood dendritic cells, as observed after an improved isolation method. Proc. Natl. Acad. Sci. USA. 87, 7698–7702.

23. Young, L. S., Dawson, C. W., Brown, K. W. Rickinson, A. B. (1989) Identification of a human epithelial cell surface protein sharing an epitope with the C3d/Epstein-Barr virus receptor of B lymphocytes. Int. J. Cancer. 43, 786–794.

24. Valent, P., Majdic, O., Maurer, D., Bodger, M., Muhm, M. Bettelheim, P. (1990) Further characterization of surface membrane structures expressed on human basophils and mast cells. Int Arch Allergy Appl Immunol. 91, 198–203.

25. O'Grady, J. T., Stewart, S., Lowrey, J., Howie, S. E. M. Krajewski, A. S. (1994) CD40 expression in hodgkin's disease. Am. J. Path. 144, 21–26.

26. Potocnik, A. J., Kinne, R., Menninger, H., Zacher, J., Emmrich, F. Kroczek, R. A. (1990) Expression of activation antigens on T cells in rheumatoid arthritis patients. Scand. J. Immunol. 31, 213–224.

27. Bevilacqua, M. P. 1993. Endothelial-leukocyte adhesion molecules. Ann. Rev. Immunol. 11: 767.

28. Springer, T. A. 1994. Traffic signals for lymphocyte recirculation and leukocyte emigration: the multistep paradigm. Cell. 76: 301.

29. Bevilacqua, M. P., S. Stengelin, M. A. Gimbrone Jr. and B. Seed. 1989. Endothelial leukocyte adhesion molecule 1: an inducible receptor for neutrophils related to complement regulatory proteins and lectins. Science. 44: 1160.

30. Graber, N., T. Venkat Gopal, D. Wilson, L. Dawson Beall, T. Polte and W. Newman. 1990. T cells bind to cytokine-activated endothelial cells via a novel, inducible sialoglycoprotein and endothelial leukocyte adhesion molecule-1. J. Immunol. 145: 819.

31. Elices, M. J., L. Osborn, Y. Takada, C. Crouse, S. Luhowsky, M. E. Hemler and R. R. Lobb. 1990. VCAM-1 on activated endothelium interacts with the leukocyte integrin VLA-4 at a site distinct from the VLA-4/fibronectin binding site. Cell. 60: 577.

32. Picker, L. J., T. K. Kishimoto, C. Wayne Smith, R. Aaron Warnock and E. C. Butcher. 1991. ELAM-1 is an adhesion molecule for skin-homing T cells. Nature. 349: 796.

33. Shimizu, Y., S. Shaw, N. Graber, T. Venkat Gopal, K. J. Horgan, G. A. Van Seventer and W. Newman. 1991. Activation-independent binding of human memory T cells to adhesion molecule ELAM-1. Nature. 349: 799.

34. Weller, P. F., T. H. Rand, S. E. Goelz, G. Chi-Rosso and R. R. Lobb. 1991. Human eosinophil adherence to vascular endothelium mediated by binding to vascular cell adhesion molecule 1 and endothelial leukocyte adhesion molecule 1. Proc. Nat. Acad. Sci, USA. 88: 7430.

35. Weller, A., S. Isenmann and D. Vestweber. 1992. Cloning of the mouse endothelial selecting. Expression of both E- and P-selectin is inducible by tumor necrosis factor α. J. Biol. Chem. 267: 15176.

36. Pober, J. S. and R. S. Cotran. 1991. Immunologic interactions of T lymphocytes with vascular endothelium. Adv Immunol. 50: 261.

REFERENCES FOR FIRST SERIES OF EXPERIMENTS

1. Pauli, S., Ehlin-Henriksson, B., Mellstedt, H., Koho, H., Ben-Aissa, H. Perlmann, P. (1985) A p50 surface antigen restricted to human urinary bladder carcinomas and B lymphocytes. Cancer Immunol. Immunother. 20, 23–28.

2. Clark, E. A. Ledbetter, J. A. (1986) Activation of human B cells mediated through two distinct cell surface differentiation antigens, Bp35 and Bp50. Proc. Natl. Acad. Sci. USA. 83, 4494–4498.

3. Lederman, S., Yellin, M. J., Krichevsky, A., Belko, J., Lee, J. J. Chess, L. (1992) Identification of a novel surface protein on activated CD4$^+$ T cells that induces contact-dependent B cell differentiation (help). J Exp Med. 175, 1091–1101.

4. Lane, P., Traunecker, A., Hubele, S., Inui, S., Lanzavecchia, A. Gray, D. (1992) Activated human T cells express a ligand for the B cell-associated antigen CD40 which participates in T cell-dependent activation of B lymphocytes. Eur J Immunol. 22, 2573–2578.

5. Armitage, R. J., Fanslow, W. C., Strockbine, L., Sato, T. A., Clifford, K. N., Macduff, B. M., Anderson, D. M., Gimpel, S. D., Davis, S. T., Maliszewski, C. R. et, a.l. (1992) Molecular and biological characterization of a murine ligand for CD40. Nature. 357, 80–82.

6. Graf, D., Korthauer, U., Mages, H. W., Senger, G. Kroczek, R. A. (1992) Cloning of TRAP, a ligand for CD40 on human T cells. Eur J Immunol. 22, 3191–3194.

7. Hollenbaugh, D., Grosmaire, L. S., Kullas, C. D., Chalupny, N. J., Braesch-Andersen, S., Noelle, R. J., Stamenkovic, I., Ledbetter, J. A. Aruffo, A. (1992) The human T cell antigen gp39, a member of the TNF gene family, is a ligand for the CD40 receptor: experssion of a soluble form of gp39 with B cell co-stimulatory activity. EMBO J. 11, 4313–4321.

8. Noelle, R. J., Roy, M., Shepherd, D. M., Stamenkovic, I., Ledbetter, J. A. Aruffo, A. (1992) A 39-kDa protein on activated helper T cells binds CD40 and transduces the signal for cognate activation of B cells. Proc Natl Acad Sci USA. 89, 6550–6554.

9. Lederman, S., Yellin, M. J., Cleary, A. M., Fortune, S. M. Chess, L. (1994) The understanding of contact-dependent T-cell helper function in molecular, cellular and physiological detail. Res Immunol. 145, 215–220.

10. Noelle, R. J., Ledbetter, J. A. Aruffo, A. (1992) CD40 and its ligand, an essential ligand-receptor pair for thymus-dependent B-cell activation. Immunol Today. 13, 431–433.

11. Banchereau, J., Bazan, F., Blanchard, D., Briere, F., Galizzi, J. P., van Kooten, C., Liu, Y. J., Rousset, F. Saeland, S. (1994) The CD40 antigen and its ligand. Annu. Rev. Immunol. 12, 881–922.

12. Alderson, M. R., Armitage, R. J., Tough, T. W., Strockbine, L., Fanslow, W. C. Spriggs, M. K. (1993) CD40 expression by human monocytes: regulation by cytokines and activation of monocytes by the ligand for CD40. J Exp Med. 178, 669–674.

13. Freudenthal, P. S. Steinman, R. M. (1990) The distinct surface of human blood dendritic cells, as observed after an improved isolation method. Proc. Natl. Acad. Sci. USA. 87, 7698–7702.

14. Young, L. S., Dawson, C. W., Brown, K. W. Rickinson, A. B. (1989) Identification of a human epithelial cell surface protein sharing an epitope with the C3d/Epstein-Barr virus receptor of B lymphocytes. Int. J. Cancer. 43, 786–794.

15. Galy, A. H. Spits, H. (1992) CD40 is functionally expressed on human thymic epithelial cells. J Immunol. 149, 775–782.

16. Valent, P., Majdic, O., Maurer, D., Bodger, M., Muhm, M. Bettelheim, P. (1990) Further characterization of surface membrane structures expressed on human basophils and mast cells. Int Arch Allergy Appl Immunol. 91, 198–203.

17. O'Grady, J. T., Stewart, S., Lowrey, J., Howie, S. E. M. Krajewski, A. S. (1994) CD40 expression in hodgkin's disease. Am. J. Path. 144, 21–26.

18. Potocnik, A. J., Kinne, R., Menninger, H., Zacher, J., Emmrich, F. Kroczek, R. A. (1990) Expression of activation antigens on T cells in rheumatoid arthritis patients. Scand. J. Immunol. 31, 213–224.

19. Arnett, F. C., Edworthy, S. M., Bloch, D. A., McShane, D. J., Fries, J. F., Cooper, N. S., Healey, L. A., Kapkan, S. R., Liang, M. H., Luthra, H. S., Medsger, T. A. J., Mitchell, D. M., Neustadt, D. H., Pinals, R. S., Schaller, J. G., Sharp, J. T., Wilder, R. L. Hunder, G. G. (1988) The American Rheumatism Association 1987 revised criteria for the classification of rheumatoid arthritis. Arthritis. Rheum. 31, 315–324.

20. Yellin, M. J., Sinning, J., Covey, L. R., Sherman, W., Lee, J. J., Glickman, N. E., Sippel, K. C., Rogers, J., Cleary, A. M., Parker, M. et, a.l. (1994) T lymphocyte T cell-B cell-activating molecule/CD40-L molecules induce normal B cells or chronic lymphocytic leukemia B cells to express CD80 (B7/BB-1) and enhance their costimulatory activity. J Immunol. 153, 666–674.

21. Yellin, M. J., Lee, J. J., Chess, L. Lederman, S. (1991) A human CD4– T cell leukemia subclone with contact-dependent helper function. J Immunol. 147, 3389–3395.

22. Aarden, L. A., De Groot, E. R., Schaap, O. L. Lansdorp, P. M. (1987) Production of hybridoma growth factor by human monocytes. Eur. J. Immunol. 17, 1411–1416.

23. Stamenkovic, I., Clark, E. A. Seed, B. (1989) A B-lymphocyte activation molecule related to the nerve growth factor receptor and induced by cytokines in carcinomas. EMBO J. 8, 1403–1410.

24. Springer, T. A. (1990) Adhesion receptors of the immune system. Nature. 346, 425–434.

25. Valle, A., Zuber, C. E., Defrance, T., Djossou, O., De Rie, M. Banchereau, J. (1989) Activation of human B lymphocytes through CD40 and interleukin 4. Eur. J. Immunol. 19, 1463–1467.

26. Ranheim, E. A. Kipps, T. J. (1993) Activated T cells induce expression of B7/BB1 on normal or leukemic B cells through a CD40-dependent signal. J Exp Med. 177, 925–935.

27. Raynaud, F., Bauvois, B., Gerbaud, P. Evain, B. D. (1992) Characterization of specific proteases associated with the surface of human skin fibroblasts, and their modulation in pathology. J Cell Physiol. 151, 378–385.

28. Clark, E. A. Shu, G. (1990) Association between IL-6 and CD40 signalling: IL-6 induces phosphorylation of CD40 receptors. J Immunol. 145, 1400–1406.

29. Firestein, G. S., Alvaro, G. J. M., Maki, R. Alvaro, G. J. M. (1990) Quantitative analysis of cytokine gene expression in rheumatoid arthritis. J Immunol. 144, 3347–3353.

30. Arend, W. P. Dayer, J. M. (1990) Cytokines and cytokine inhibitors or antagonists in rheumatoid arthritis. Arthritis Rheum. 33, 305–315.

31. Bucala, R., Ritchlin, C., Winchester, R. Cerami, A. (1991) Constitutive production of inflammatory and mitogenic cytokines by rheumatoid synovial fibroblasts. J Exp Med. 173, 569–574.

32. Butler, D. M., Piccoli, D. S., Hart, P. H. Hamilton, J. A. (1988) Stimulation of human synovial fibroblast DNA synthesis by recombinant human cytokines. J Rheumatol. 15, 1463–1470.

33. Fleischmajer, R., Perlish, J. S. Reeves, J. R. T. (1977) Cellular Infiltrates in scleroderma skin. Arthritis Rheum. 20, 975–983.

34. Furst, D. E., Clements, P. J., Granze, P., Gale, R. Roberts, N. (1979) A syndrome resembling progressive systemic sclerosis after bone marrow transplantation. A model for scleroderma? Arthritis Rheum. 22, 904–910.

35. Ferrara, J. L. M. Deeg, H. J. (1991) Mechanisms of disease. Graft-versus-host disease. N. Engl. J. Med. 324, 667–674.

36. Fishel, R., Barbul, A., Wasserkrug, H. L., Penberthy, L. T., Rettura, G. Efron, G. (1983) Cyclosporine A impairs wound healing in rats. J. Surg. Res. 34, 572–575.

37. Peterson, J. M., Barbul, A., Breslin, R. J., Wasserkrug, H. L. Efron, G. (1987) Significance of T-lymphocytes in wound healing. Surgery. 102, 300–304.

38. Schrier, D. J., Phan, S. H. McGarry, B. M. (1983) The effects of the nude (nu/nu) mutation on bleomycin-induced pulmonary fibrosis. Am. Rev. Respir. Dis. 127, 614–617.

39. Allen, J. B., Malone, D. G., Wahl, S. M., Calandra, G. B. Wilder, R. L. (1985) Role of the thymus in streptococcal cell wall-induced arthritis and hepatic granuloma formation. Comparative studies of pathology and cell wall distribution in athymic and euthymic rats. J. Clin. Invest. 76, 1042–1056.

40. Wahl, S. M., Hunt, D. A., Allen, J. B., Wilder, R. L., Paglia, L. Hand, A. R. (1986) Bacterial cell wall-induced hepatic granulomas. An in vivo model of T cell-dependent fibrosis. J. Exp. Med. 163, 884–902.

41. Dayer, J. M., Breard, J., Chess, L. Krane, S. M. (1979) Participation of monocyte-macrophages and lymphocytes in the production of a factor that stimulates collagenase and prostaglandin release by rheumatoid synovial cells. J. Clin. Invest. 64, 1386–1392.

42. Dayer, J. M., Beutler, B. Ceram, A. (1985) Cachectin/tumor necrosis factor stimulates collagenase and prostaglandin E2 production by human synovial cells and dermal fibroblasts. J. Exp. Med. 162, 2163–2168.

43. Dayer, J. M., de Rochemonteix, B., Burrus, B., Cemczuk, S. Dinarello, C. A. (1986) Human recombinant inteleukin 1 stimulates collagenase and prostaglandin E2 production by human synovial cells. J Clin Invest. 77, 645–648.

44. Ishikawa, H. Ziff, M. (1976) Electron microscopic observations of immunoreactive cells in the rheumatoid synovial membrane. Arthritis Rheum. 19, 1–14.

45. Golay, J., Cusmano, G. Introna, M. (1992) Independent regulation of m-myc, B-myb, and c-myb gene expression by inducers and inhibitors of proliferation in human B lymphocytes. J Immunol. 149, 300–308.

46. Qu, Z., Hernandez Garcia, C., O'Rourke, L. M., Planck, S. R., Kohli, M. Rosenbaum, J. T. (1994) Local proliferation of fibroblast-like synoviocytes contributes to synovial hyperplasia: results of proliferating cell nuclear antigen/cyclin, c-myc, and nucleolar organizer staining. Arthritis Rheum. 2, 212–220.

47. Van Seventer, G. A., Newman, W., Shimizu, Y., Nutman, T. B., Tanaka, Y., Horgan, K. J., Gopal, T. V., Ennis, E., O'Sullivan, D., Grey, H. Shaw, S. (1991) Analysis of T cell stimulation by superantigen plus major histocompatibility complex class II molecules or by CD3 monoclonal antibody: costimulation by purified adhesion ligands VCAM-1, ICAM-1, but not ELAM-1. J Exp Med. 174, 901–913.

48. Hale, L. P., Martin, M. E., McCollum, D. E., Nunley, J. A., Springer, T. A., Singer, K. H. Haynes, B. F. (1989) Immunohistologic analysis of the distribution of cell adhesion molecules within the inflammatory synovial microenvironment. Arthritis Rheum. 32, 22–30.

49. Morales, D. J., Wayner, E., Elices, M. J., Alvaro, G. J. M., Zvaifler, N. J. Firestein, G. S. (1992) Alpha 4/beta 1 integrin (VLA-4) ligands in arthritis. Vascular cell adhesion molecule-i expression in synovium and on fibroblast-like synoviocytes. J Immunol. 149, 1424–1431.

50. Kriegsmann, J., Keyszer, G. M., Geiler, T., Brauer, R., Gay, R. E. Gay, S. (1995) Expression of vascular cell adhesion molecule-l mRNA and protein in rheumatoid synovium demonstrated by in situ hybridization and immunohistochemistry. Lab Invest. 72, 208–214.

51. Marlor, C. W., Webb, D. L., Bombara, M. P., Greve, J. M. Blue, M. L. (1992) Expression of vascular cell adhesion molecule-1 in fibroblastlike synoviocytes after stimulation with tumor necrosis factor. Am J Pathol. 140, 1055–1060.

52. Chin, J. E., Winterrowd, G. E., Krzesicki, R. F. Sanders, M. E. (1990) Role of cytokines in inflammatory synovitis. The coordinate regulation of intercellular adhesion molecule 1 and HLA class I and class II antigens in rheumatoid synovial fibroblasts. Arthritis Rheum. 33, 1776–1786.

53. Krzesicki, R. F., Fleming, W. E., Winterrowd, G. E., Hatfield, C. A., Sanders, M. E. Chin, J. E. (1991) T lymphocyte adhesion to human synovial fibroblasts. Role of cytokines and the interaction between intercellular adhesion molecule 1 and CD a/CD18. Arthritis Rheum. 34, 1245–1253.

54. Durie, F. H., Fava, R. A., Foy, T. M., Aruffo, A., Ledbetter, J. A. Noelle, R. J. (1993) Prevention of collagen-induced arthritis with an antibody to gp39, the ligand for CD40. Science. 261, 1328–1330.

REFERENCES FOR SECOND SERIES OF EXPERIMENTS

1. Bevilacqua, M. P. 1993. Endothelial-leukocyte adhesion molecules. Ann. Rev. Immunol. 11: 767.

2. Springer, T. A. 1994. Traffic signals for lymphocyte recirculation and leukocyte emigration: the multistep paradigm. Cell. 76: 301.

3. Bevilacqua, M. P., S. Stengelin, M. A. Gimbrone Jr. and B. Seed. 1989. Endothelial leukocyte adhesion molecule 1: an inducible receptor for neutrophils related to complement regulatory proteins and lectins. Science. 44: 1160.

4. Graber, N., T. Venkat Gopal, D. Wilson, L. Dawson Beall, T. Polte and W. Newman. 1990. T cells bind to cytokine-activated endothelial cells via a novel, inducible sialoglycoprotein and endothelial leukocyte adhesion molecule-1. J. Immunol. 145: 819.

5. Elices, M. J., L. Osborn, Y. Takada, C. Crouse, S. Luhowsky, M. E. Hemler and R. R. Lobb. 1990. VCAM-1 on activated endothelium interacts with the leukocyte integrin VLA-4 at a site distinct from the VLA-4/fibronectin binding site. Cell. 60: 577.

6. Picker, L. J., T. K. Kishimoto, C. Wayne Smith, R. Aaron Warnock and E. C. Butcher. 1991. ELAM-1 is an adhesion molecule for skin-homing T cells. Nature. 349: 796.

7. Shimizu, Y., S. Shaw, N. Graber, T. Venkat Gopal, K. J. Horgan, G. A. Van Seventer and W. Newman. 1991. Activation-independent binding of human memory T cells to adhesion molecule ELAM-1. Nature. 349: 799.

8. Weller, P. F., T. H. Rand, S. E. Goelz, G. Chi-Rosso and R. R. Lobb. 1991. Human eosinophil adherence to vascular endothelium mediated by binding to vascular cell adhesion molecule 1 and endothelial leukocyte adhesion molecule 1. Proc. Nat. Acad. Sci, USA. 88: 7430.

9. Weller, A., S. Isenmann and D. Vestweber. 1992. Cloning of the mouse endothelial selecting. Expression of both E- and P-selectin is inducible by tumor necrosis factor a. J. Biol. Chem. 267: 15176.

10. Pober, J. S. and R. S. Cotran. 1991. Immunologic interactions of T lymphocytes with vascular endothelium. Adv Immunol. 50: 261.

11. Potocnik, A. J., R. Kinne, H. Menninger, J. Zacher, F. Emmrich and R. A. Kroczek. 1990. Expression of activation antigens on T cells in rheumatoid arthritis patients. Scand. J. Immunol. 31: 213.

12. Pauli, S., B. Ehlin-Henriksson, H. Mellstedt, H. Koho, H. Ben-Aissa and P. Perlmann. 1985. A p50 surface antigen restricted to human urinary bladder carcinomas and B lymphocytes. Cancer Immunol. Immunother. 20: 23.

13. Clark, E. A. and J. A. Ledbetter. 1986. Activation of human B cells mediated through two distinct cell surface differentiation antigens, Bp35 and Bp5O. Proc. Natl. Acad. Sci. USA. 83: 4494.

14. Alderson, M. R., R. J. Armitage, T. W. Tough, L. Strockbine, W. C. Fanslow and M. K. Spriggs. 1993. CD40 expression by human monocytes: regulation by cytokines and activation of monocytes by the ligand for CD40. J Exp Ned. 178: 669.

15. Freudenthal, P. S. and R. M. Steinman. 1990. The distinct surface of human blood dendritic cells, as observed after an improved isolation method. Proc. Natl. Acad. Sci. USA. 87: 7698.

16. Valent, P., O. Majdic, D. Maurer, M. Bodger, M. Muhm and P. Bettelheim. 1990. Further characterization of surface membrane structures expressed on human basophils and mast cells. Int Arch Allergy Appl Immunol. 91: 198.

17. Young, L. S., C. W. Dawson, K. W. Brown and A. B. Rickinson. 1989. Identification of a human epithelial cell surface protein sharing an epitope with the C3d/Epstein-Barr virus receptor of B lymphocytes. Int. J. Cancer. 43: 786.

18. Galy, A. H. and H. Spits. 1992. CD40 is functionally expressed on human thymic epithelial cells. J Immunol. 149: 775.

20. Lederman, S., M. J. Yellin, A. Krichevsky, J. Belko, J. J. Lee and L. Chess. 1992. Identification of a novel surface protein on activated CD4$^+$ T cells that induces contact-dependent B cell differentiation (help). J Exp Ned. 175: 1091.

21. Lane, P., A. Traunecker, S. Hubele, S. Inui, A. Lanzavecchia and D. Gray. 1992. Activated human T cells express a ligand for the B cell-associated antigen CD40 which participates in T cell-dependent activation of B lymphocytes. Eur J Immunol. 22: 2573.

22. Armitage, R. J., W. C. Fanslow, L. Strockbine, T. A. Sato, K. N. Clifford, B. M. Macduff, D. M. Anderson, S. D. Gimpel, S. T. Davis, C. R. Maliszewski and a. 1. et. 1992. Molecular and biological characterization of a murine ligand for CD40. Nature. 357: 80.

23. Graf, D., U. Korthauer, H. W. Mages, G. Senger and R. A. Kroczek. 1992. Cloning of TRAP, a ligand for CD40 on human T cells. Eur J Immunol. 22: 3191.

24. Hollenbaugh, D., L. S. Grosmaire, C. D. Kullas, N. J. Chalupny, S. Braesch-Andersen, R. J. Noelle, I. Stamenkovic, J. A. Ledbetter and A. Aruffo. 1992. The human T cell antigen gp39, a member of the TNF gene family, is a ligand for the CD40 receptor: experssion of a soluble form of gp39 with B cell co-stimulatory activity. EMBO J. 11: 4313.

25. Noelle, R. J., M. Roy, D. M. Shepherd, I. Stamenkovic, J. A. Ledbetter and A. Aruffo. 1992. A 39-kDa protein on activated helper T cells binds CD40 and transduces the signal for cognate activation of B cells. Proc Natl Acad Sci USA. 89: 6550.

26. Lederman, S., M. J. Yellin, A. M. Cleary, S. M. Fortune and L. Chess. 1994. The understanding of contact-dependent T-cell helper function in molecular, cellular and physiological detail. Res Immunol. 145: 215.

27. Noelle, R. J., J. A. Ledbetter and A. Aruffo. 1992. CD40 and its ligand, an essential ligand-receptor pair for thymus-dependent B-cell activation. Immunol Today. 13: 431.

28. Banchereau, J., F. Bazan, D. Blanchard, F. Briere, J. P. Galizzi, C. van Kooten, Y. J. Liu, F. Rousset and S. Saeland. 1994. The CD40 antigen and its ligand. Annu. Rev. Immunol. 12: 881.

29. Korthauer, U., D. Graf, H. W. Mages, F. Briere, M. Padayachee, S. Malcolm, A. G. Ugazio, L. D. Notarangelo, R. L. Levinsky and R. A. Kroczek. 1993. Defective expression of T-cell CD40 ligand causes X-linked Immunodeficiency with hyper-IgM. Nature. 361: 539.

30. DiSanto, J. P., J. Y. Bonnefoy, J. F. Gauchat, A. Fischer and G. de Saint Basile. 1993. CD40 ligand mutations in X-linked immunodeficiency with hyper-IgM. Nature. 361: 541.

31. Allen, R. C., R. J. Armitage, M. E. Conley, H. Rosenblatt, N. A. Jenkins, N. G. Copeland, M. A. Bedell, S. Edelhoff, C. M. Disteche, D. K. Simoneaux and a. 1. et. 1993. CD40 ligand gene defects responsible for X-linked hyper-IgM syndrome. Science. 259: 990.

32. Aruffo, A., M. Farrington, D. Hollenbaugh, X. Li, A. Milatovich, S. Nonoyama, J. Bajorath, L. S. Grosmaire, R. Stenkamp, M. Neubauer and a. 1. et. 1993. The CD40 ligand, gp39, is defective in activated T cells from patients with X-linked hyper-IgM syndrome. Cell. 72: 291.

33. Ramesh, N., R. Fuleihan, V. Ramesh, S. Lederman, M. J. Yellin, S. Sharma, L. Chess, F. S. Rosen and R. S. Geha. 1993. Deletions in the ligand for CD40 in X-linked immunoglobulin deficiency with normal or elevated IgM (HIGMX-1). Int Immunol. 5: 769.

34. Kawabe, T., T. Naka, K. Yoshida, T. Tanaka, H. Fujiwara, S. Suematsu, N. Yoshida, T. Kishimoto and H. Kikutani. 1994. The immune response in CD40-deficient mice: impaired immunoglobulin class switching and germinal center formation. Immunity. 1: 167.

35. Xu, J., T. M. Foy, J. D. Laman, E. A. Elliot, J. J. Dunn, T. J. Waldschmidt, J. Elsemore, R. J. Noelle and R. A. Flavell. 1994. Mice deficient for the CD40 ligand. Immunity. 1: 423.

36. Caux, C., C. Massacrier, B. Banbervliet, B. Dubois, C. Van Kooten, I. Durand and J. Banchereau. 1994. Activation of human dendritic cells through CD40 ross-linking. J. Exp. Ned. 180: 1263.

37. Yellin, M. J., J. Sinning, L. R. Covey, W. Sherman, J. J. Lee, N. E. Glickman, K. C. Sippel, J. Rogers, A. M. Cleary, M. Parker and a. 1. et. 1994. T lymphocyte T cell-B cell-activating molecule/CD40-L molecules induce normal B cells or chronic lymphocytic leukemia B cells to express CD80 (B7/BB-1) and enhance their costimulatory activity. J Immunol. 153: 666.

38. Lederman, S., M. J. Yellin, G. Inghirami, J. J. Lee, D. M. Knowles and L. Chess. 1992. Molecular interactions mediating T-B lymphocyte collaboration in human lymphoid follicles. Roles of T cell-B-cell-activating molecule (5c8 antigen) and CD40 in contact-dependent help. J Immunol. 149: 3817.

39. Lederman, S., M. J. Yellin, A. M. Cleary, A. Pernis, G. Inghirami, L. E. Cohn, L. R. Covey, J. J. Lee, P. Rothman and L. Chess. 1994. T-BAM/CD40-L on helper T lymphocytes augments lymphokine-induced B cell Ig isotype switch recombination and rescues B cells from programmed cell death. J Immunol. 152: 2163.

40. Jaffe, E., R. Nachman, C. Becker and R. Minick. 1973. Culture of human endothelial cells derived from umbilical veins. Identification by morphologic and immunologic criteria. J. Clin. Invest. 52: 2745.

41. Thornton, S., S. Mueller and E. Levine. 1983. Human endothelial cells: use of heparin in long term cloning and serial cultivation. Science. 222: 623.

42. Yellin, M. J., J. J. Lee, L. Chess and S. Lederman. 1991. A human CD4⁻ T cell leukemia subclone with contact-dependent helper function. J Immunol. 147: 3389.

43. Holthofer, H., I. Virtanen, A. L. Kariniemi, M. Hormia, E. Linder and A. Miettinen. 1982. Ulex europaeus I lectin as a marker for vascular endothelium in human tissue. Lab. Invest. 47: 60.

44. Fina, L., H. V. Molgaard, D. Robertson, N. J. Bradley, P. Monaghan, D. Delia, R. D. Sutherland, M. A. Baker and M. F. Greaves. 1990. Expression of the CD34 gene in vascular endothelial cells. Blood. 75: 2417.

45. Stamenkovic, I., E. A. Clark and B. Seed. 1989. A B-lymphocyte activation molecule related to the nerve growth factor receptor and induced by cytokines in carcinomas. EMBO J. 8: 1403.

46. Ranheim, E. A. and T. J. Kipps. 1993. Activated T cells induce expression of B7/BB1 on normal or leukemic B cells through a CD40-dependent signal. J Exp Med. 177: 925.

47. Hughes, C. C., C. O. Savage and J. S. Pober. 1990. The endothelial cell as a regulator of T-cell function. Immunol Rev. 117: 85.

48. Hughes, C. C. W., C. O. S. Savage and J. S. Prober. 1990. Endothelial cells augment T cell interleukin 2 production by a contact-dependent mechanism involving CD2/LFA-3 interactions. J. Exp. Med. 171: 1453.

49. Guinan, E. C., B. R. Smith, J. T. Doukas, R. A. Miller and J. S. Pober. 1989. Vascular endothelial cells enhance T cell responses by markedly augmenting IL-2 concentrations. Cell. Immunol. 118: 166.

50. Azuma, M., D. Ito, H. Yagita, K. Okumura, J. H. Phillips, L. L. Lanier and C. Somoza. 1993. B70 antigen is a second ligand for CTLA-4 and CD28. Nature. 366: 76.

51. Kennedy, M. K., K. M. Mohler, K. D. Shanebeck, P. R. Baum, K. S. Picha, C. A. Otten-Evans, C. A. Janeway and K. H. Grabstein. 1994. Induction of B cell costimulatory function by recombinant murine CD40 ligand. Eur. J. Immunol. 24: 116.

52. Maliszewski, C. R., K. Grabstein, W. C. Fanslow, R. Armitage, M. K. Spriggs and T. A. Sato. 1993. Recombinant CD40 ligand stimulation of murine B cell growth and differentiation: cooperative effects of cytokines. Eur J Immunol. 23: 1044.

53. Spriggs, M. K., R. J. Armitage, L. Strockbine, K. N. Clifford, B. M. Macduff, T. A. Sato, C. R. Maliszewski and W. C. Fanslow. 1992. Recombinant human CD40 ligand stimulates B cell proliferation and immunoglobulin E secretion. J Exp Med. 176: 1543.

54. Yellin, M. J., K. Sippel, G. Inghirami, L. R. Covey, J. J. Lee, J. Sinning, E. A. Clark, L. Chess and S. Lederman. 1994. CD40 molecules induce down-modulation and endocytosis of T cell surface T cell-B cell activating molecule/CD40-L. Potential role in regulating helper effector function. J Immunol. 152: 598.

55. Barrett, T. B., G. Shu and E. A. Clark. 1991. CD40 signalling activates CD11a/CD18 (LFA-1)-mediated adhesion in B cells. J. Immunol. 146: 1722.

56. Flores-Romo, L., D. Estoppey and K. B. Bacon. 1993. Anti-CD40 antibody stimulates the VLA-4-dependent adhesion of normal and LFA-1-deficient B cells to endothelium. Immunology. 79: 445.

57. Collins, T., A. J. Korman, C. T. Wake, J. M. Boss, D. J. Kappes, W. Fiers, K. A. Ault, M. A. Gimbrone Jr., J. L. Strominger and J. S. Prober. 1984. Immune interferon activates multiple class II major histocompatibility complex genes and the associated invariant chain gene in human endothelial cells and dermal fibroblasts. Proc. Natl. Acad. Sci, USA. 81: 4917.

58. Barkley, D., S. Allard, M. Feldmann and R. N. Maini. 1989. Increased expression of HLA-DQ antigens by interstitial cells and endothelium in the synovial membrane of rheumatoid arthritis patients compared with reactive arthritis patients. Arthrit. Rheum. 32: 955.

59. Gruschwitz, M., N. Sepp, H. Kofler and G. Wick. 1991. Expression of class II-MHC antigens in the dermis of patients with progressive systemic sclerosis. Immunobiology. 182: 234.

60. Salomon, R. N., C. C. W. Huges, F. J. Schoen, D. D. Payne, J. S. Pober and P. Libby. 1991. Human coronary transplantation-associated arteriosclerosis. Evidence for a chronic immune reaction to activated graft endothelial cells. Am. J. Path. 138: 791.

61. Murray, A. G., M. M. Khodadoust, J. S. Pober and A. L. M. Bothwell. 1994. Porcine aortic endothelial cells activate human T cells: direct presentation of MHC antigens and costimulation by ligands for human CD2 and CD28. Immunity. 1: 57.

62. Koch, A. E., J. C. Burrows, G. K. Haines, T. M. Carlos, J. M. Harlan and S. Joseph Leibovich. 1991. Immunolocalization of endothelial and leukocyte adhesion molecules in human rheumatoid arthritis and osteoarthritis synovial tissues. Lab. Invest. 64: 313.

63. Gruschwitz, M. S., O. P. Hornstein and P. von den Driesch. 1995. Correlation of soluble adhesion molecules in the peripheral blood of scleroderma patients with their in situ expression and with disease activity. Arthrit. Rheum. 38: 184.

64. Brockmeyer, C., M. Ulbrecht, D. J. Schendel, E. H. Weiss, G. Hillebrand, K. Burkhardt, W. Land, M. J. Gokel, G. Riethmuller and H. E. Feucht. 1993. Distribution of cell adhesion molecules (ICAM-1, VCAM-1 and ELAM-1) in renal tissue during allograft rejection. Transplantation. 55: 610.

65. Wick, G., G. Schett, A. Amberger, R. Kleindienst and Q. Xu. 1995. Is atherosclerosis an immunologically mediated disease. Immunol. Today. 16: 27.

66. Durie, F. H., R. A. Fava, T. M. Foy, A. Aruffo, J. A. Ledbetter and R. J. Noelle. 1993. Prevention of collagen-induced arthritis with an antibody to gp39, the ligand for CD40. Science. 261: 1328.

67. Durie, F. H., T. M. Foy and R. J. Noelle. 1994. The role of CD40 and its ligand (gp39) in peripheral and central tolerance and its contribution to autoimmune disease. Res. Immunol. 145: 200.

What is claimed is:

1. A method for treating reperfusion injury in a subject other than a graft recipient, by inhibiting activation of cells bearing CD40 on their surface, other than B cells, comprising the step of administering to said subject an antibody, Fab, F(ab')2 or a single chain antibody, which binds specifically to an antigen specifically bound by monoclonal antibody 5c8, produced by the hybridoma having ATCC Accession No. HB 10916, wherein said antibody, Fab, F(ab')2 or single chain antibody, inhibits binding between CD40 ligand and CD40 on the surface of said cells, wherein said antibody, Fab, F(ab')2 or single chain antibody, is effective to inhibit transmigration of inflammatory cells across the barrier of endothelial cells in said subject .

2. The method according to claim 1, wherein said CD40-bearing cells are selected from the group consisting of: fibroblasts, endothelial cells, epithelial calls, T cells, basophils, macrophages, Reed-Steinberg cells, keratinocytes, dendritic cells, plasma cells and myeloma cells.

3. The method according to claim 1, wherein said antibody is a monoclonal antibody or a polyclonal antibody.

4. The method according to claim 1, wherein said antibody is selected from the group consisting of: a chimeric antibody, a humanized antibody and an antibody which includes a CDR region from a first human antibody and an antibody scaffold from a second human antibody.

5. The method according to claim 1, wherein said antibody is a primatized antibody.

6. The method according to claim 1, wherein said antibody is monoclonal antibody 5c8, produced by the hybridoma having ATCC Accession No. HB 10916.

7. The method according to claim 1, wherein said antibody is a humanized monoclonal antibody 5c8.

8. The method according to claim 1, wherein said antibody is a primatized monoclonal antibody 5c8.

9. The method according to claim 1, wherein said Fab has a complementarity determining region of a light chain or a heavy chain.

10. The method according to claim 1, wherein said Fab has a variable region of a light chain or a heavy chain.

11. The method according to claim 1, wherein said antibody, Fab, F(ab')2 or single chain antibody, is selected by a screening method, comprising the steps of:

(a) isolating a sample of cells comprising CD40-bearing fibroblasts, endothelial cells, epithelial cells, T cells, basophils, macrophages, Reed-Steinberg cells, keratinocytes, dendritic cells, plasma cells or myeloma tells;

(b) culturing said sample under conditions permitting activation of CD40-bearing fibroblasts, endothelial cells, epithelial cells, T cells, basophils, macrophages, Reed-Steinberg cells, keratinocytes, dendritic cells, plasma cells or myeloma cells;

(c) contacting said sample with:
 (i) cells expressing a protein which is specifically recognized by monoclonal antibody 5c8, produced by the hybridoma having ATCC Accession No. HB 10916, or
 (ii) a protein which is specifically recognized by monoclonal antibody 5c8, produced by the hybridoma having ATCC Accession No. 10916,
under conditions which permit activation of said CD40-bearing fibroblasts, endothelial cells, epithelial cells, T cells, basophils, macrophages, Reed-Steinberg cells, keratinocytes, dendritic cells, plasma cells or myeloma cells;

(d) contacting said sample with an antibody, Fab, F(ab')2 or single chain antibody, under conditions which permit said antibody, Fab, F(ab')2 or single chain antibody, to inhibit activation of said CD40-bearing fibroblasts, endothelial cells, epithelial cells, T cells, basophils, macrophages, Reed-Steinberg cells, keratinocytes, dendritic cells, plasma cells or myeloma cells; and (e) determining whether said antibody, Fab, F(ab')2 or single chain antibody, is capable of inhibiting activation of said CD40-bearing fibroblasts, endothelial cells, epithelial cells, T cells, basophils, macrophages, Reed-Steinberg cells, keratinocytes, dendritic cells, plasma cells or myeloma cells.

12. The method according to claim 11, wherein the sample of cells is isolated from a tissue.

13. The method according to claim 11, wherein the sample of cells is selected from the group consisting of: a cell line in culture, cells isolated from an animal and cells isolated from a body fluid.

14. The method according to claim 1, wherein said subject is a mammal.

15. The method according to claim 14, wherein said mammal is a human or a non-human primate.

16. The method according to claim 1, wherein said antibody, Fab, F(ab')2 or single chain antibody, is administered to said subject by a parenteral route.

17. The method according to claim 1, wherein said antibody, Fab, F(ab')2 or single chain antibody, is administered to said subject at intervals ranging from each month to every other month.

18. The method according to claim 1, wherein said antibody, Fab, F(ab')2 or single chain antibody, is administered to said subject dally for the first three days of treatment, after which the antibody, Fab, F(ab')2 or single chain antibody, is administered once every three weeks.

19. The method according to claim 1, wherein said antibody, Fab, F(ab')2 or single chain antibody, is administered to said subject daily intravenously for the first three days of treatment, after which the antibody, Fab, F(ab')2 or single chain antibody, is administered subcutaneously or intramuscularly once every week.

20. The method according to claim 1, wherein said antibody, Fab, F(ab')2 or single chain antibody, is administered to said subject parenterally, daily followed by administration of the antibody, Fab, F(ab')2 or single chain antibody, subcutaneously or intramuscularly once every week.

21. The method according to claim 1, wherein said antibody, Fab, F(ab')2 or single chain antibody, is administered to said subject at a dosage range of between about 0.01 and 200 mg/kg body weight of said subject.

22. The method according to claim 1, wherein said antibody, Fab, F(ab')2 or single chain antibody, is administered to said subject at a dosage range of between 0.01 and 50 mg/kg body weight of said subject.

23. The method according to claim 1, wherein said antibody, Fab, F(ab')2 or single chain antibody, is administered to said subject at a dosage range of between about 1 and 30 mg/kg body weight of said subject.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
        (A) LENGTH: 146 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:1:

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Gly Leu Tyr Tyr Ile Tyr Ala Gln Val Thr Phe Cys Ser
50                  55                  60

Asn Arg Glu Ala Ser Ser Gln Ala Pro Phe Ile Ala Ser Leu Cys Leu
65                  70                  75                  80

Lys Ser Pro Gly Arg Phe Glu Arg Ile Leu Leu Arg Ala Ala Asn Thr
            85                  90                  95

His Ser Ser Ala Lys Pro Cys Gly Gln Gln Ser Ile His Leu Gly Gly
        100                 105                 110

Val Phe Glu Leu Gln Pro Gly Ala Ser Val Phe Val Asn Val Thr Asp
        115                 120                 125

Pro Ser Gln Val Ser His Gly Thr Gly Phe Thr Ser Phe Gly Leu Leu
    130                 135                 140

Lys Leu
145